US006410224B1

(12) United States Patent
Stinchcomb et al.

(10) Patent No.: US 6,410,224 B1
(45) Date of Patent: *Jun. 25, 2002

(54) RIBOZYME TREATMENT OF DISEASES OR CONDITIONS RELATED TO LEVELS OF NF-κB

(75) Inventors: Dan T. Stinchcomb; Kenneth G. Draper; James McSwiggen, all of Boulder, CO (US)

(73) Assignee: Ribozyme Pharmaceuticals, Inc., Boulder, CO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/777,916

(22) Filed: Dec. 23, 1996

Related U.S. Application Data

(63) Continuation of application No. 08/291,932, filed on Aug. 15, 1994, now Pat. No. 5,658,780, which is a continuation-in-part of application No. 08/245,466, filed on May 18, 1994, now abandoned, which is a continuation-in-part of application No. 07/987,132, filed on Dec. 7, 1992, now abandoned.

(51) Int. Cl.[7] .............................. C07H 21/04; C12Q 1/68
(52) U.S. Cl. ..................... 435/6; 435/91.31; 435/325; 435/366; 435/375; 536/245
(58) Field of Search ................... 435/6, 91.31, 172.3, 435/320.1, 325, 366; 536/23.1, 24.5, 23.2; 514/44

(56) References Cited

U.S. PATENT DOCUMENTS

| 4,987,071 A | | 1/1991 | Cech |
| 5,168,053 A | | 12/1992 | Altman |
| 5,213,580 A | | 5/1993 | Slepian et al. |
| 5,328,470 A | | 7/1994 | Nabel et al. |
| 5,496,698 A | * | 3/1996 | Draper et al. ............... 435/6 |
| 5,525,468 A | * | 6/1996 | ReSwigger ............... 435/6 |

FOREIGN PATENT DOCUMENTS

| EP | 9211298 | 12/1992 |
| WO | 9103162 | 3/1991 |
| WO | 9115580 | 10/1991 |
| WO | 9118624 | 12/1991 |
| WO | 9118625 | 12/1991 |
| WO | 9118913 | 12/1991 |
| WO | 9200080 | 1/1992 |
| WO | 9207065 | 4/1992 |
| WO | 9220348 | 11/1992 |
| WO | 9302654 | 2/1993 |
| WO | 9308845 | 5/1993 |
| WO | 9309789 | 5/1993 |
| WO | 9315187 | 8/1993 |
| WO | 9323569 | 11/1993 |
| WO | 9402595 | 2/1994 |

OTHER PUBLICATIONS

Zaia et al., Status of ribozyme and antisense–based developmental approaches for anti–HIV–1 therapy, Annals N.Y. Acad. Sci., vol. 660, pp. 95–106, Jan. 1992.*
Geisler et al. Cell 71:613–621, Nov. 13, 1992.*
Thanos et al. Cell 71:777–789, Nov. 27, 1992.*
Laurence et al. J. Virology 65:213–219, Jan. 1991.*
Bours et al Molecular and Cellular Biology 12:685–695, Feb. 1992.*
Schmid et al. Nature 352:773–736, 1991.*
Ghosh et al. Cell 62:1019–1029, 1980.*
Kitajima et al. Science 258:1792–1795, Dec. 1992.*
Stull. Pharm. Res. 12:465–483 (1995).*
Rojanasakul, Adv. Drug Delivery 18 (1996) 115–131.*
Gewirtz et al. PNAS 93:3161–3163 (1996).*
Akhtar and Juliano, "Cellular Uptake and Intracellular Fate of Antisense Oligonucleotides," *Trends Cell Biol.* 2:139–144 (1992).
Alitalo et al., "Aberrant Expression of An Amplified c–myb oncogene in two cell lines from a colon carcinoma," *Proc. Natl. Acad. Sci. USA* 81:4534–4538 (1984).
Anfossi et al., "An oligomer complementary to c–myb–encoded mRNA inhibits proliferation of human myeloid leukemia cell lines," *Proc. Natl. Acad. Sci. USA* 86:3379–3383 (1989).
Austin et al., "Intimal Proliferation of Smooth Muscle Cells as an Explanation for Recurrent Coronary Artery Stenosis After Percutaneous Transluminal Coronary Angioplasty," *J. Am. Coll. Cardiol.* 6:369–375 (1985).
Ballantyne et al., "Nucleotide sequence of the cDNA for murine intracellular adhesion molecule–1 (ICAM–1)," *Nucleic Acids Research* 17:5853 (1989).
Banskota et al., "Insulin, Insulin–Like Growth Factor I and Platelet–Derived Growth Factor Interact Additively in the Induction of the Protooncogene c–myc and Cellular Proliferation in Cultured Bovine Aortic Smooth Muscle Cells," *Molec. Endocrinol.*, 3:1183–1190 (1989).
Barinaga, "Ribozymes: Killing the Messenger," *Science* 262:1512–1514 (1993).
Belknap et al., "Transcriptional Regulation in Vascular Cells; Genetically Modified Animals," *J. Cell. Biochem.* S18A:277 (1994).
Bennett et al., "Cationic Lipids Enhance Cellular Uptake and Activity of Phosphorothioate Antisense Oligonucleotides," *Mol. Pharmacology* 41:1023–1033 (1992).
Biotech Abstracts Act. #91–00050 EP 388758 (Sep. 26, 1990).

(List continued on next page.)

Primary Examiner—Andrew Wang
(74) Attorney, Agent, or Firm—McDonnell, Boehnen Hulbert & Berghoff

(57) ABSTRACT

Enzymatic RNA molecules which cleave rel A mRNA.

4 Claims, 6 Drawing Sheets

OTHER PUBLICATIONS

Biro et al., "Inhibitory Effects of Antisense Oligodeoxynucleotides targeting c–myc mRNA on smooth muscle cell proliferation and migration," *Proc. Natl. Acad. Sci. U S A,* 90:654–658 (1993).

Blam et al., "Addition of Growth Hormone Secretion Signal to Basic Fibroblast Growth Factors Results in Cell Transformation and Secretion of Aberrant Forms of the Protein," *Oncogene* 3:129–136 (1988).

Brown et al.,"Expression of the c–myb Proto–oncogene in Bovine Vascular Smooth Muscle Cells," *J. Biol. Chem.* 267:4625–4630 (1992).

Bywater et al., "Expression of Recombinant Platelet–Derived Growth Factor A–Chain and B–Chain Homodimers in Rat Cells and Human Fibroblastic Reveals Differences in Protein Processing and Autocrine Effects," *Mol. Cell. Biol.* 8:2753–2762 (1988).

Calabretta et al., "Normal and Leukemic Hematopoietic Cells Manifest Differential Sensitivity to Inhibitory Effects of c–myb Antisense Oligodeoxynucleotides: An in vitro study relevant to bone marrow purging," *Proc. Natl. Acad. Sci. USA,* 88:2351–2355 (1991).

Califf et al., "Restenosis: The Clinical Issues," in *Textbook of Interventional Cardiology,* E.J. Topol, eds., W. B. Saunders, Philadelphia, pp. 363–394 (1990).

Cameron and Jennings, "Specific Gene Suppression by Engineered Ribozymes in Monkey Cells." *Proc. Natl. Acad. Sci. USA* 86:9139 (1989).

Chen, "Multitarget–Ribozyme Directed to Cleave up to Nine Highly Conserved HIV–1 env RNA Regions Inhibits HIV–1 Replication–Potential Effectiveness Against Most Presently Sequenced HIV–1 Isolates," *Nucleic Acids Res.* 20:4581–4589 (1992).

Chowrira and Burke, "Extensive Phosphorothioate Substitution Yields Highly Active and Nuclease–Resistant Hairpin Ribozymes," *Nucleic Acids Res.* 20:2835–2840 (1992).

Chuat and Galibert, "Can Ribozymes be Used to Regulate Procaryote Gene Expression?" *Biochem. and Biophys. Res. Commun.* 162:1025 (1989).

Cleary et al., "Cloning and Structural Analysis of cDNAs for bcl–2 and A Hybrid bcl–2/Immunoglobulin Transcript Resulting From the t(14;18) Translocation," *Cell* 47:199–28 (1986).

Clowes et al., "Kinetics of Cellular Proliferation After Arterial Injury," *Lab Invest.* 49:327–333 (1983).

Collins and Olive, "Reaction Conditions and Kinetics of Self–Cleavage of a Ribozyme Derived From *Neurospora* VS RNA," *Biochemistry* 32:2795–2799 (1993).

Cotten et al., "High Efficiency Receptor–Mediated Delivery of Small and Large (48 Kilobase Gene Constructs Using the Endosome–Disruption Activity of Defective or Chemically Inactivated Adenovirus Particles," *Proc. Natl. Acad. Sci. USA* 89:6094–6098 (1992).

Cotten et al., "Transferrin–Polycation–Mediated Introduction of DNA into Human Leukemic Cells: Stimulation by Agents that Affect the Survival of Transfected DNA or Modulate Transferrin Receptor Levels" (Abstract), *Proc. Natl. Acad. Sci. USA* 87:4033–4037 (1990).

Cotten et al., "Chicken Adenovirus (CELO Virus) Particles Augment Receptor–Mediated DNA Delivery to Mammalian Cells and Yield Exceptional Levels of Stable Transformants," *J. Virol.* 67:3777–3785 (1993).

Cristiano et al., "Hepatic Gene Therapy: Adenovirus Enhancement of Receptor–Mediated Gene Delivery and Expression in Primary Hepatocytes," *Proc. Natl. Acad. Sci. USA* 90:2122–2126 (1993).

Curiel et al., "Adenovirus Enhancement of Transferrin–Polylysine–Mediated Gene Delivery," *Proc. Nat. Acad. Sci. USA,* 88:8850–8854 (1991).

Dropulic et al., "Functional Characterization of a U5 Ribozyme: Intracellular Suppression of Human Immunodeficiency Virus Type I Expression," *J. Virol.* 66:1432–1441 (1992).

Eck et al., "Inhibition of Phorbol Ester–Induced Cellular Adhesion by Competitive Binding of $NF-_\kappa B$ In Vivo," *Mol. Cell. Biol.* 13:6530–6536 (1993).

Edgington, "Ribozymes: Stop Making Sense," *Biotechnology* 10:256–262 (1992).

Elroy–Stein and Moss, "Cytoplasmic Expression Based on Constitutive Synthesis of Bacteriophage T7 RNA Polymerase in Mammalian Cells," *Proc. Natl. Acad. Sci. USA* 87:6743–7 1990).

Ferguson et al., "Compensation for Treating Wounds to Inhibit Scar Tissue—Contains Agent Esp. Antibody, Which Selectively Neutralises Fibrotic Growth Factors," WPI Acc#92–3659974/44.

Ferns et al., "Inhibition of Neointimal Smooth Muscle Accumulation After Angioplasty by an Antibody to PDGF," *Science* 253:1129–1132 (1991).

Gao and Huang, "Cytoplasmic Expression of a Reporter Gene by Co–Delivery of T7 RNA Polymerase and T7 Promoter Sequence with Cationic Liposomes," *Nucleic Acids Res.* 21:2867–72 (1993).

Garratt et al.,"Differential Histopathology of Primary Atherosclerotic and Restenotic Lesions in Coronary Arteries and Saphenous Vein Bypass Grafts: Analysis of Tissue Obtained From 73 Patients by Directional Atherectomy," *J. Am. Coll. Cardio.* 17:442–428 (1991).

Goldberg et al., "Vascular Smooth Muscle Cell Kinetics: A New Assay for Studying Patterns of Cellular Proliferation in vivo," *Science,* 205:920–922 (1979).

Griffin and Baylin, "Expression of the c–myb Oncogene in Human Small Cell Lung Carcinoma," *Cancer Res.* 45:272–275 (1985).

Grotendorst et al., "Attachment of Smooth Muscle Cells to Collagen and Their Migration Toward Platelet–Derived Growth Factor," *Proc. Natl. Acad. Sci. USA* 78:3669–3672 (982).

Guerrier–Takada et al., "The RNA Moiety of Ribonuclease P Is the Catalytic Subunit of the Enzyme," *Cell* 35:849 (1983).

Hajjar et al., "Tumor Necrosis Factor–Mediated Release of Platelet–Derived Growth Factor From Cultured Endothelial Cells," *J. Exp. Med.* 166:235–245 (1987).

Hampel et al., "'Hairpin' Catalytic RNA Model: Evidence for Helices and Sequence Requirement for Substrate RNA", *Nucleic Acids Research* 18:299–304 (1990).

Harris et al., "Receptor–Mediated Gene Transfer to Airway Epithelial Cells in Primary Culture," *Am. J. Respir. Cell Mol. Biol.,* 9:441–447 (1993).

Haseloff and Gerlach, "Simple RNA Enzymes with New and Highly Specific Endoribonuclease Activities," *Nature* 334:585–591 (1988).

Herschlag, "Implications of Ribozyme Kinetics for Targeting the Cleavage of Specific RNA Molecules in vivo: More Isn't Always Better," *Proc. Natl. Acad. Sci. USA* 88:6921–5 (1991).

Hertel et al., "Numbering System for the Hammerhead," *Nucleic Acids Res.* 20:3252 (1992).

Higashiyama et al., "A Heparin–Binding Growth Factor Secreted by Macrophage–Like Cells That is Related to EFG," *Science* 251:936–939 (1991).

Jaeger et al., "Improved Predictions of Secondary Structures for RNA," *Proc. Natl. Acad. Sci. USA* 86:7706–7710 (1989).

Jeffries and Symons, "A Catalytic 13–mer Ribozyme," *Nucleic Acids Research* 17:1371 (1989).

Kashani–Sabet et al., "Reversal of the Malignant Phenotype by an Anti–ras Ribozyme," *Antisense Research & Development* 1:3–15 (1992).

Kaye et al., "Structure and Expression of the Human L–myc Gene Reveal a Complex Pattern Of Alternative mRNA Processing," *Mol. Cell. Biol.* 8:186–195 (1988).

Kindy and Sonenshein, "Regulation of Oncogene Expression in Cultured Aortic Smooth Muscle Cells," *J. Biol. Chem.* 261:12865–12868 (1986).

Kita et al., "Sequence and expression of rat ICAM–1," *Biochem. Biophys. Acta* 1131:108–110 91992).

Kitajima et al., "Ablation of Transplanted HTLV–I Tax–Transformed Tumors in Mice by Antisense Inhibition of NF–$_\kappa$B," *Science* 258:1792–1795 (1992).

Klagsbrun and Edelman, "Biological and Biochemical Properties of Fibroblast Growth Factors," *Arteriosclerosis* 9:269–278 (1989).

Koizumi et al., "Ribozymes Designed to Inhibit Transformation of NIH3T3 Cells by the Activated c–Ha–ras Gene," *Gene* 117:179 (1992).

Komuro et al., "Endothelin stimulates c–fos and c–myc expression and proliferation of vascular smooth muscle cells," *FEBS Letters* 238:249–252 (1988).

Kunapuli et al., "Molecular Cloning of Human Angiotensinogen cDNA and Evidence for the Presence of Its mRNA in Rat Heart—DNA Sequence," *Cir. Res.* 60:786–790 (1987).

Kunsch and Rosen, "NF–$_\kappa$B and Subunit–Specific Regulation of the Interleukin–8 Promoter," *Mol. Cell. Biol.* 13:6137–6146 (1993).

La Rosa et al., "Differential Regulation of the c–myc Oncogene Promoter by the NF–$_\kappa$B Rel Family of Transcription Factors," *Mol. Cell. Biol.* 14:1039–1044 (1994).

Lenardo and Baltimore, "NF–$_\kappa$B: A Pleiotropic Mediator of Inducible and Tissue Specific Gene Control," *Cell* 58:227–229 (1989).

Lieber et al., "Stable High–Level Gene Expression in Mammalian Cells by T7 Phage $NA Polymerase," *Methods Enzymol.* 217:47–66 (1993).

L'Huillier et al., "Cytoplasmic Delivery of Ribozymes Leads to Efficient Reduction in α–Lactalbumin mRNA Levels in C1271 Mouse," *Embo J.* 11:4411–4418 (1992).

Lindner and Reidy, "Proliferation of Smooth Muscle Cells After Vascular Injury Is Inhibited by an Antibody Against Basic Fibroblast Growth Factor," *Proc. Natl. Acad. Sci. USA* 88:3739–3743 (1991).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

Liu et al., "Specific NF–$_\kappa$B Subunits Act in Concert with Tat To Stimulate Human Immunodeficiency Virus Type I Transcription," *J. Virology* 66:3883–3887 (1992).

Majello et al., "Human c–myb Protooncogene: Nucleotide Sequence of cDNA and Organization of the Genomic Locus," *Proc. Natl. Acad. Sci. USA*, 83:9636–9640 (1986).

Mamone et al., "Design of Hammerhead Ribozymes Targeted to Sequences in HIV, HSV and the RAT ANF Gene," Abstract of Keystone, CO (May 27, 1992).

McGrath et al., "Structure and Organization of the Human Ki–ras Protooncogene And a Related Processed Pseudogene," 304:501–506 (1983).

Melani et al., "Inhibition of Proliferation by c–myb Antisense Oligodeoxynucleotide in Colon Adenocarcinoma Cell Lines that Express c–myb," *Cancer Res.* 51:2897–2901 (1991).

Minvielle et al., "A Novel Calcitonin Carboxyl–Terminal Peptide Produced in Medullary Thyroid Carcinoma by Alternative RNA Processing of the Calcitonin–Calcitonin Gene–Related Peptide Gene," *J. Biol. Chem.* 266:24627–24631 (1991).

Nabel et al., "Site–Specific Gene Expression in Vivo by Direct Gene Transfer Into the Arterial Wall," *Science* 249:1285–1288 (1990).

Nabel et al., "Recombinant Platelet–Derived Growth Factor B Gene Expression in Porcine Arteries Induces Intimal Hyperplasia In Vivo," *J. Clin. Invest.* 91:1822–1829 1993).

Narayanan et al., "Evidence for Differential Functions of the p50 and p65 Subunits of NF–$_\kappa$B with a Cell Adhesion Model," *Mol. Cell. Biol.* 13:3802–3810 (1993).

O'Brien et al., "Vascular Cell Adhesion Molecule–1 is Expressed in Human Coronary Atherosclerotic Plaques," *J. Clin. Invest.* 92:945–951 (1993).

Ohno et al., "Gene Therapy for Vascular Smooth Muscle Cell Proliferation After Arterial Injury," *Science* 265:781–784 (1994).

Ohkawa et al., *Nucleic Acids Symp. Ser.* 27:15–6 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Pavco et al., "Regulation of Self–Splicing Reactions by Antisense RNA," Abstract of Keystone, CO (May 27, 1992).

Perkins et al., "Distinct combinations of NF–$_\kappa$B subunits determine the specificity of transcriptional activation," *Proc. Natl. Acad. Sci. USA* 89:1529–1533 (1992).

Perreault et al., "Mixed Deoxyribo– and Ribo–Oligonucleotides with Catalytic Activity," *Nature* 344:565–568 (1990).

Perrotta and Been, "Cleavage of Oligoribonucleotides by a Ribozyme Derived from the Hepatitis δ Virus RNA Sequence," *Biochemistry* 31:16 (1992).

Pieken et al., "Kinetic Characterization of Ribonuclease–Resistant 2'–Modified Hammerhead Ribozymes," *Science* 253:314–317 (1991).

Popoma et al., "Clinical Trials of Restenosis After Coronary Angioplasty," *Circulation* 84:1426–1436 (1991).

Raines et al., "Interleukin–1 Mitogenic Activity for Fibroblasts and Smooth Muscle Cells Is Due to PDGF–AA," *Science* 243:393–396 (1989).

Raschella et al., "Inhibition of Proliferation by c–myb Antisense RNA and Oligodeoxynucleotides in Transformed Neuroectodermal Cell Lines," *Cancer Res.* 52:4221–4226 (1992).

Ratajczak et al., "In Vivo Treatment of Human Leukemia in a scid Mouse Model With c–myb Antisense Oligodeoxynucleotides," *Proc. Natl. Acad. Sci. USA* 89:11823–11827 (1992).

Ray and Prefontaine, "Physical association and functional antagonism between the p65 subunit of transcription factor NF–$_\kappa$B and the glucocorticoid receptor," *Proc. Natl. Acad. Sci. USA* 91:752–756 (1994).

Read et al., "NF–$_\kappa$B and I$_\kappa$B$\alpha$: An Inducible Regulatory System in Endothelial Activation," *J. Exp. Med.* 179:503–512 (1994).

Riessen et al., "Arterial Gene Transfer Using Pure DNa Applied Directly to a Hydrogel–Coated Angioplasty Balloon,"*Human Gene Therapy* 4:749–758 (1993).

Ross et al., "A Platelet–Dependent Serum Factor That Stimulates the Proliferation of Arterial Smooth Muscle Cells In Vitro," *Proc. Natl. Acad. Sci. USA* 71:1207–1210 (1974).

Roessler et al., "Adenovirus–mediated Gene Transfer to Rabbit Synovium In Vivo," *J. Clin. Invest.* 92;1085–1092 (1993).

Rossi et al., *J. Cell Biochem.* Suppl 14A:D428 (1990).

Rossi et al., "Ribozymes as Anti–HIV–1 Therapeutic Agents: Principles, Applications, and Problems," *Aids Research and Human Retroviruses* 8:183 (1992).

Ruben et al., "Isolation of a rel–related human cDNA that potentially encodes the 65–kD subunit of NF, kappba B," *Science* 251:5000 (1991).

Ruben et al., "Isolation of a rel–related human cDNA that potentially encodes the 65–kD subunit of NF, kappba B," *Science* 254:5028 (1991).

Ruben et al., *Genes & Development* 6:745–760 (1992).

Sarver et al., "Ribozymes as Potential Anti–HIV–1 Therapeutic Agents," *Science* 247:1222–1225 (1990).

Sarver et al., "Catalytic RNAs (Ribozymes): A New Frontier in Biomedical Applications," *AIDS Res. Revs.* 2:259 (1992).

Saville and Collins, "A Site–Specific Self–Cleavage Reaction Performed by a Novel RNA In *Neurospora Mitochondria,*" *Cell* 61:685–696 (1990).

Saville and Collins, "RNA–Mediated Ligation of Self–Cleavage Products of a Neurospora Mitochondrial Plasmid Transcript," *Proc. Natl. Acad. Sci. USA* 88:8826–8830 (1991).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Semba, "A v–erbB–Related Protooncogene, C–erB–2, Is Distinct From the c–erbB–1/Epidermal Growth Factor–Receptor Gene and Is Amplified in A Human Salivary Gland Adenocarcinoma," *Proc. Natl. Acad. Sci. USA* 82:6497–6501 (1985).

Seth et al., "Mechanism of Enhancement of DNA Expression Consequent to Cointernalization of a Replication–Deficient Adenovirus and Unmodified Plasmid dDNA," *J. Virol.,* 68:933–940 (1994).

Sessa et al., "Molecular Cloning and Expression of a cDNA Encoding Endothelial Cell Nitric Oxide Synthase," *J. Biol. Chem.* 267:15274–15276 (1992).

Shi et al., "Downregulation of c–myc Expression by Antisense Oligonucleotides Inhibits Proliferation of Human Smooth Muscle Cell," *Circulation* 88:1190–1195 (1993).

Shu et al., "Differential Regulation of Vascular Cell Adhesion Molecule 1 Gene Expression by Specific NF–$_\kappa$B Subunits in Endothelial and Epithelial Cells," *Mol. Cell. Biol.* 13:6283–6289 (1993).

Simons et al., "Antisense c–myb Oligonucleotides Inhibit Intimal Arterial Smooth Muscle Cell Accumulation in vivo," *Nature* 359:67–70 (1992).

Simons et al., "Relation Between Activated Smooth Muscle Cells in Coronary–Artery Lesions and Restenosis After Atherectomy," *New Engl. J. Med.* 328:608–613 (1993).

Simmons et al., "ICAM, an adhesion ligand of LFA–1 is homologous to the neural cell adhesion molecule NCAM," *Nature* 331:624–627 (1988).

Sioud and Drulica, "Prevention of Human Immunodeficiency Virus Type 1 Integrase Expression in *Escherichia coli* by a Ribozyme," *Proc. Natl. Acad. Sci. USA* 88:7303 (1991).

Sjolund et al., "Arterial Smooth Muscle Cells Express Platelet–Derived Growth Factor (PDGF) A Chain mRNA, Secrete a PDGF–Like Mitogen, and Bind Exogenous PDGF in a Phenotype– and Growth State–Dependent Manner," *J. Cell. Biol.* 106:403–413 (1988).

Slamon et al., "Studies of the Human c–myb Gene and its Products in Human Acute Leukemias," *Science* 233:3467–351 (1986).

Slamon et al., "Expression of Cellular Oncogenes in Human Malignancies," *Science* 224:256–262 (1984).

Stull and Szoka, "Antigene, Ribozyme and Aptamer Nucleic Acid Drugs: Progress and Prospects," *Pharmaceutical Research* 12:465–483 (1995).

Taira et al., "Construction of a novel RNA–transcript–trimming plasmid which can be used both in vitro and in place of run–off and (G)–free transcriptions and in vivo as multi–sequences transcription vectors," *Nucleic Acids Research* 19:5125–30 (1991).

Ten Dijke et al., "Recombinant Transforming Growth Factor Type Beta–3 Biological Activities and Receptor–Binding Properties in Isolated Bone Cells," *Mol. Cell Biol.* 10:4473–4479 (1990).

Tessler et al, "Basic Fibroblast Growth Factor Accumulates in the Nuclei of Vairous BFGF–Producing Cell Types," *J. Cell. Physiol.* 145:310–317 (1990).

Thiele et al., "Regulation of c–myb Expression in Human Neuroblastoma Cells During Retinoic Acid–Induced Differentiation," *Mol. Cell. Biol.* 8:1677–1683 (1988).

Torelli et al., "Expression of c–myb Protooncogene and Other Cell Cycle–Related Genes in Normal and Neoplastic Human Colonic Mucosa," *Cancer Res.* 47:5266–5269 (1987).

Uhlenbeck, "A Small Catalytic Oligoribonucleotide," *Nature* 327:596–600 (1987).

Usman and Cedergren, "Exploiting the chemical synthesis of RNA," *Trends in Biochem. Sci.* 17:334–339 (1992).

Usman et al.,"Automated Chemical Synthesis of Long Oligoribonucleotides Using 2'–O–Silylated Ribonucleoside 3'–O–Phosphoramidtes on a Controlled–Pore Glass Support: Synthesis of a 43–Nucleoside Sequence Similar to the 3'–Half Molecule of an *Escherichia coli* Formylmethoionine tRNA," *J. Am. Chem. Soc.* 109:7845–7854 (1987).

van de Stolpe et al., "12–O–Tetradecanoylphorbol–13–acetate– and Tumor Necrosis Factor α–meidated Induction of Intercellular Adhesion Molecule–1 Is Inhibited by Dexamethasone," *J. Biol. Chem.* 269:6185–6192 (1994).

Ventura et al., "Activation of HIV–Specific Ribozyme Activity by Self–Cleavage," *Nucleic Acids Res.* 21:3249–55 (1993).

Weerasinghe et al., "Resistance to Human Immunodeficiency Virus Type 1 (HIV–1) Infection in Human $CD4^+$ Lymphocyte–Derived Cell Lines Conferred by Using Retroviral Vectors Expressing and HIV–1 RNA–Specific Ribozyme," *Journal of Virology* 65:5531–4 (1994).

Weiser et al., "The Growth–Related Transcription Factor OCT–1 is Expressed as a Function of Vascular Smooth Muscle Cell Modulation," *J. Cell. Biochem.* S18A:282 (1994).

Westin et al., "Alternative Splicing of the Human c–myb Gene," *Oncogene* 5:1117–1124 (1990).

Willard et al., *Circulation* 86:I–473 (1992).

Woolf et al., "Specificity of Antisense Oligonucleotides in vivo," *Proc. Natl. Acad. Sci. USA* 89:7305–7309 (1992).

Yu et al., "A Hairpin Ribozyme Inhibits Expression of Diverse Strains of Human Immunodeficiency Virus Type 1," *Proc. Natl. Acad. Sci. U S A* 90:6340–6344 (1993).

Zenke et al., "Receptor–mediated Endocytosis of Transferrin–Polycation Conjugates: An Efficient Way to Introduce DNA into Hematopoietic Cells" (Abstract), *Proc. Natl. Acad. Sci. USA* 87:3655–3659 (1990).

Zhou et al., "Synthesis of Function mRNA in Mammalian ells by Bacteriophage T3 RNA Polymerse," *Mol. Cell. Biol.* 10:4529–4537 (1990).

* cited by examiner

*Figure 1: Hammerhead Ribozyme*

Figure 2. Hammerhead Ribozyme Substrate Motifs

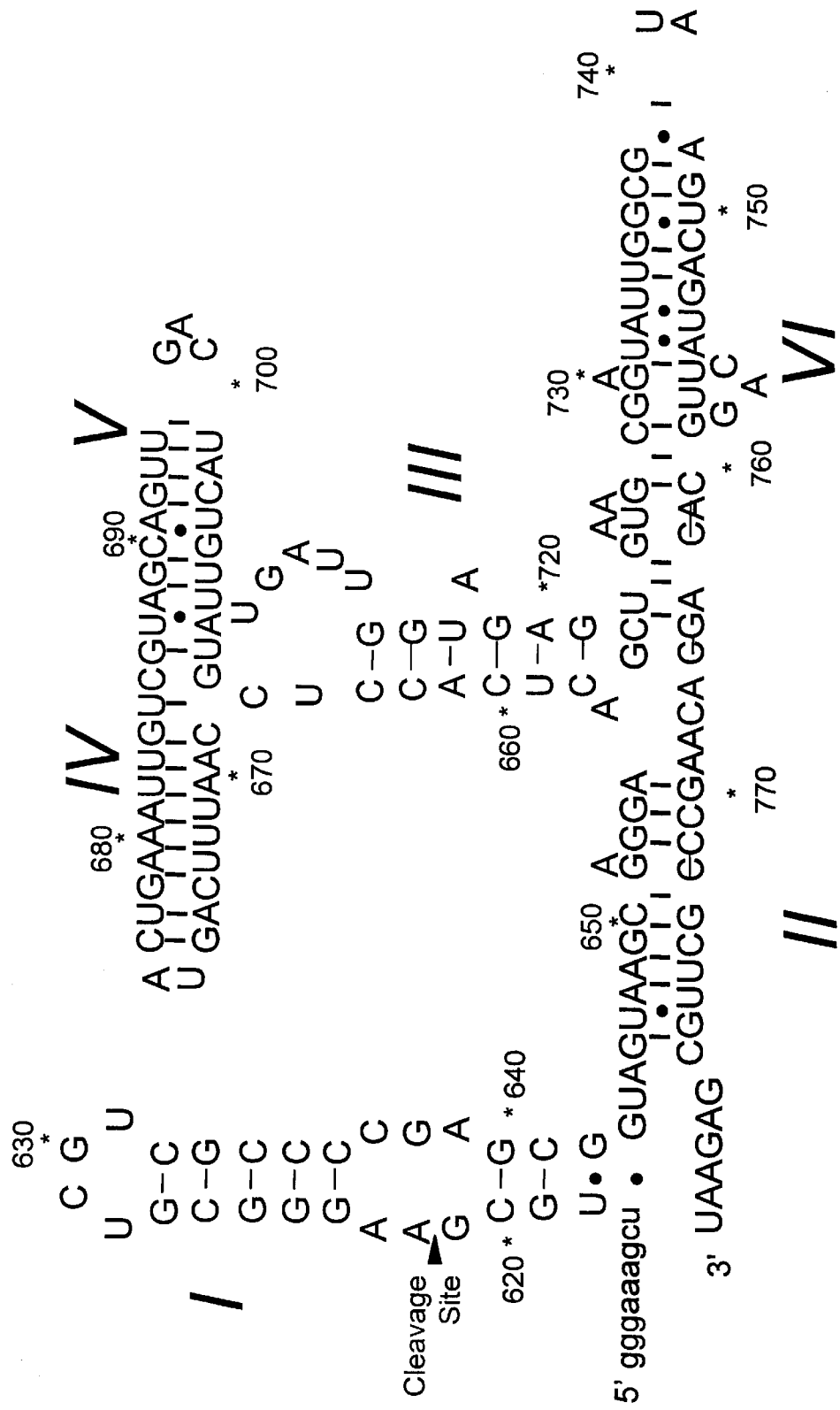
Figure 5. Neurospora vs Ribozyme

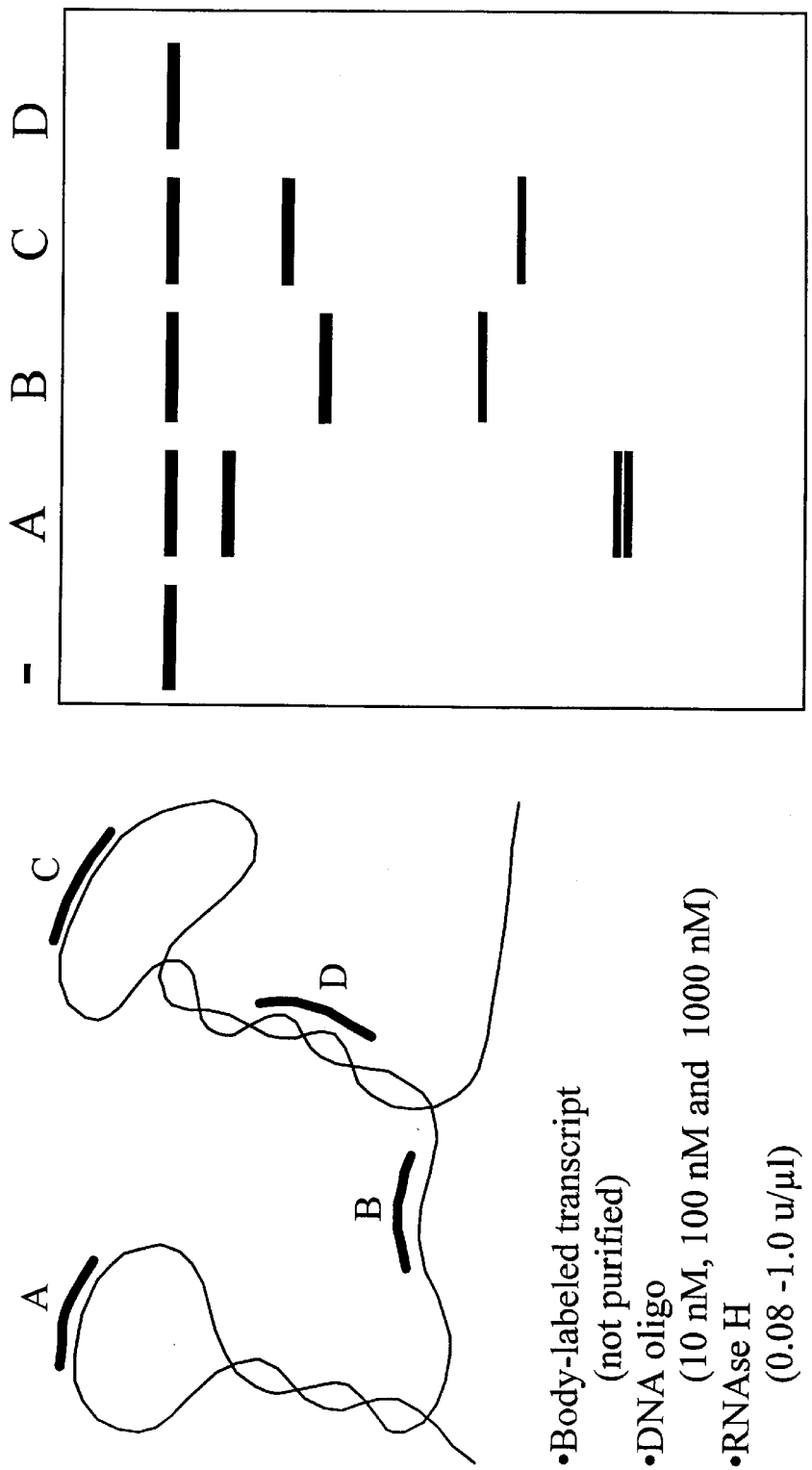

US 6,410,224 B1

RIBOZYME TREATMENT OF DISEASES OR CONDITIONS RELATED TO LEVELS OF NF-κB

RELATED APPLICATIONS

This is continuation of application Ser. No. 08/291,932 filed Aug. 15, 1994, now U.S. Pat. No. 5,658,780, hereby incorporated by reference in its totality (including drawings), which is a continuation-in-part of Stinchcomb et al., "Method and Composition for Treatment of Restenosis and Cancer Using Ribozymes," filed May 18, 1994, U.S. Ser. No. 08/245,466, now abandoned, which is a continuation-in-part of Draper, "Method and Reagent for Treatment of a Stenotic Condition", filed Dec. 7, 1992, U.S. Ser. No. 07/987,132, now abandoned both hereby incorporated by reference herein.

FIELD OF THE INVENTION

The present invention relates to therapeutic compositions and methods for the treatment or diagnosis of diseases or conditions related to NF-κB levels, such as restenosis, rheumatoid arthritis, asthma, inflammatory or autoimmune disorders and transplant rejection.

BACKGROUND OF THE INVENTION

The following is a brief description of the physiological role of NF-κB. The discussion is not meant to be complete and is provided only for understanding of the invention that follows. This summary is not an admission that any of the work described below is prior art to the claimed invention.

The nuclear DNA-binding activity, NF-κB, was first identified as a factor that binds and activates the immunoglobulin κ light chain enhancer in B cells. NF-κB now is known to activate transcription of a variety of other cellular genes (e.g., cytokines, adhesion proteins, oncogenes and viral proteins) in response to a variety of stimuli (e.g., phorbol esters, mitogens, cytokines and oxidative stress). In addition, molecular and biochemical characterization of NF-κB has shown that the activity is due to a homodimer or heterodimer of a family of DNA binding subunits. Each subunit bears a stretch of 300 amino acids that is homologous to the oncogene, v-rel. The activity first described as NF-κB is a heterodimer of p49 or p50 with p65. The p49 and p50 subunits of NF-κB (encoded by the nf-κB2 or nf-κB1 genes, respectively) are generated from the precursors NF-κB1 (p105) or NF-κB2 (p100). The p65 subunit of NF-κB (now termed Rel A) is encoded by the rel A locus.

The roles of each specific transcription-activating complex now are being elucidated in cells (N. D. Perkins, et al., 1992 Proc. Natl Acad. Sci USA 89, 1529–1533). For instance, the heterodimer of NF-κB1 and Rel A (p50/p65) activates transcription of the promoter for the adhesion molecule, VCAM-1, while NF-κB2/RelA heterodimers (p49/p65) actually inhibit transcription (H. B. Shu, et al., Mol. Cell. Biol. 13, 6283–6289 (1993)). Conversely, heterodimers of NF-κB2/RelA (p49/p65) act with Tat-I to activate transcription of the HIV genome, while NF-κB1/ RelA (p50/p65) heterodimers have little effect (J. Liu, N. D. Perkins, R. M. Schmid, G. J. Nabel, J. Virol. 1992 66, 3883–3887). Similarly, blocking rel A gene expression with antisense oligonucleotides specifically blocks embryonic stem cell adhesion; blocking NF-κB1 gene expression with antisense oligonucleotides had no effect on cellular adhesion (Narayanan et al., 1993 Mol. Cell. Biol. 13, 3802–3810). Thus, the promiscuous role initially assigned to NF-κB in transcriptional activation (M. J. Lenardo, D. Baltimore, 1989 Cell 58, 227–229) represents the sum of the activities of the rel family of DNA-binding proteins. This conclusion is supported by recent transgenic "knock-out" mice of individual members of the rel family. Such "knock-outs" show few developmental defects, suggesting that essential transcriptional activation functions can be performed by more than one member of the rel family.

A number of specific inhibitors of NF-κB function in cells exist, including treatment with phosphorothioate antisense oliogonucleotide, treatment with double-stranded NF-κB binding sites, and over expression of the natural inhibitor MAD-3 (an IκB family member). These agents have been used to show that NF-κB is required for induction of a number of molecules involved in inflammation, as described below.

NF-κB is required for phorbol ester-mediated induction of IL-6 (I. Kitajima, et al., Science 258, 1792–5 (1992)) and IL-8 (Kunsch and Rosen, 1993 Mol. Cell. Biol. 13, 6137–46).

NF-κB is required for induction of the adhesion molecules ICAM-1 (Eck, et al., 1993 Mol. Cell. Biol. 13, 6530–6536), VCAM-1 (Shu et al., supra), and E-selectin (Read, et al., 1994 J. Exp. Med. 179, 503–512) on endothelial cells.

NF-κB is involved in the induction of the integrin subunit, CD18, and other adhesive properties of leukocytes (Eck et al., 1993 supra).

The above studies suggest that NF-κB is integrally involved in the induction of cytokines and adhesion molecules by inflammatory mediators. Two recent papers point to another connection between NF-κB and inflammation: glucocorticoids may exert their anti-inflammatory effects by inhibiting NF-κB. The glucocorticoid receptor and p65 both act at NF-κB binding sites in the ICAM-1 promoter (van de Stolpe, et al., 1994 J. Biol. Chem. 269, 6185–6192). Glucocorticoid receptor inhibits NF-κB-mediated induction of IL-6 (Ray and Prefontaine, 1994 Proc. Natl Acad. Sci USA 91, 752–756). Conversely, overexpression of p65 inhibits glucocorticoid induction of the mouse mammary tumor virus promoter. Finally, protein cross-linking and co-immunoprecipitation experiments demonstrated direct physical interaction between p65 and the glucocorticoid receptor (Id.).

SUMMARY OF THE INVENTION

This invention relates to ribozymes, or enzymatic RNA molecules, directed to cleave mRNA species encoding Rel A protein (p65). In particular, applicant describes the selection and function of ribozymes capable of cleaving this RNA and their use to reduce activity of NF-κB in various tissues to treat the diseases discussed herein. Such ribozymes are also useful for diagnostic applications.

Ribozymes that cleave rel A mRNA represent a novel therapeutic approach to inflammatory or autoimmune disorders. Antisense DNA molecules have been described that block NF-κB activity. See Narayanan et al., supra. However, ribozymes may show greater perdurance or lower effective doses than antisense molecules due to their catalytic properties and their inherent secondary and tertiary structures. Such ribozymes, with their catalytic activity and increased site specificity (as described below), represent more potent and safe, therapeutic molecules than antisense oligonucleotides.

Applicant indicates that these ribozymes are able to inhibit the activity of NF-κB and that the catalytic activity of the ribozymes is required for their inhibitory effect. Those of ordinary skill in the art, will find that it is clear from the examples described that other ribozymes that cleave rel A encoding mRNAs may be readily designed and are within the invention.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf, T. M., et al., 1992, *Proc. Natl. Acad. Sci. USA*, 89, 7305–7309). Thus, the specificity of action of a ribozyme is greater than that of an antisense oligonucleotide binding the same RNA site.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence) or Neurospora VS RNA. Examples of such hammerhead motifs are described by Rossi et al., 1992, *Aids Research and Human Retroviruses*, 8, 183, of hairpin motifs by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, 1989, *Biochemistry*, 28, 4929, and Hampel et al., 1990, *Nucleic Acids Res.earch*, 18,299, and an example of the hepatitis delta virus motif is described by Perrotta and Been, 1992, *Biochemistry*, 31, 16, of the RNaseP motif by Guerrier-Takada et al., 1983,*Cell*, 35, 849, Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799) and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

The invention provides a method for producing a class of enzymatic cleaving agents which exhibit a high degree of specificity for the RNA of a desired target. The enzymatic nucleic acid molecule is preferably targeted to a highly conserved sequence region of a target Rel A encoding mRNA such that specific treatment of a disease or condition can be provided with either one or several enzymatic nucleic acids. Such enzymatic nucleic acid molecules can be delivered exogenously to specific cells as required. Alternatively, the ribozymes can be expressed from DNA vectors that are delivered to specific cells.

Synthesis of nucleic acids greater than 100 nucleotides in length is difficult using automated methods, and the therapeutic cost of such molecules is prohibitive. In this invention, small enzymatic nucleic acid motifs (e.g., of the hammerhead or the hairpin structure) are used for exogenous delivery. The simple structure of these molecules increases the ability of the enzymatic nucleic acid to invade targeted regions of the mRNA structure. However, these catalytic RNA molecules can also be expressed within cells from eukaryotic promoters (e.g., Scanlon, K. J., et al., 1991,*Proc. Natl. Acad. Sci. USA*, 88, 10591–5; Kashani-Sabet, M., et al., 1992, *Antisense Res. Dev.*, 2, 3–15; Dropulic, B., et al., 1992, *J Virol*, 66, 1432–41; Weerasinghe, M., et al., 1991, *J Virol*, 65, 5531–4; Ojwang, J. O., et al., 1992, *Proc. Natl. Acad. Sci. USA*, 89, 10802–6; Chen, C. J., et al., 1992, *Nucleic Acids Res.*, 20, 4581–9; Sarver, H., et al., 1990, *Science*, 247, 1222–1225)). Those skilled in the art realize that any ribozyme can be expressed in eukaryotic cells from the appropriate DNA vector. The activity of such ribozymes can be augmented by their release from the primary transcript by a second ribozyme (Draper et al., PCT WO93/23569, and Sullivan et al., PCT WO94/02595, both hereby incorporated in their totality by reference herein; Ohkawa, J., et al., 1992, *Nucleic Acids Symp. Ser.*, 27, 15–6; Taira, K., et al., 1991, *Nucleic Acids Res.*, 19, 5125–30; Ventura, M., et al., 1993, *Nucleic Acids Res.*, 21, 3249–55) .

Inflammatory mediators such as lipopolysaccharide (LPS), interleukin-1 (IL-1) or tumor necrosis factor-a (TNF-α) act on cells by inducing transcription of a number of secondary mediators, including other cytokines and adhesion molecules. In many cases, this gene activation is known to be mediated by the transcriptional regulator, NF-κB. One subunit of NF-κB, the relA gene product (termed RelA or p65) is implicated specifically in the induction of inflammatory responses. Ribozyme therapy, due to its exquisite specificity, is particularly well-suited to target intracellular factors that contribute to disease pathology. Thus, ribozymes that cleave mRNA encoded by rel A may represent novel therapeutics for the treatment of inflammatory and autoimmune disorders.

Thus, in a first aspect, the invention features ribozymes that inhibit RelA production. These chemically or enzymatically synthesized RNA molecules contain substrate binding domains that bind to accessible regions of their target mRNAs. The RNA molecules also contain domains that catalyze the cleavage of RNA. The RNA molecules are preferably ribozymes of the hammerhead or hairpin motif. Upon binding, the ribozymes cleave the target RelA encoding mRNAs, preventing translation and p65 protein accumulation. In the absence of the expression of the target gene, a therapeutic effect may be observed.

By "inhibit" is meant that the activity or level of RelA encoding mRNA is reduced below that observed in the absense of the ribozyme, and preferably is below that level observed in the presence of an inactive RNA molecule able to bind to the same site on the mRNA, but unable to cleave that RNA.

Such ribozymes are useful for the prevention of the diseases and conditions discussed above, and any other diseases or conditions that are related to the level of NF-κB activity in a cell or tissue. By "related" is meant that the inhibition of relA mRNA and thus reduction in the level of NF-κB activity will relieve to some extent the symptoms of the disease or condition.

Ribozymes are added directly, or can be complexed with cationic lipids, packaged within liposomes, or otherwise delivered to target cells. The RNA or RNA complexes can be locally administered to relevant tissues ex vivo, or in vivo through injection or the use of a catheter, infusion pump or stent, with or without their incorporation in biopolymers. In preferred embodiments, the ribozymes have binding arms which are complementary to the sequences in Tables II, III, VI–VII. Examples of such ribozymes are shown in Tables IV–VII. Examples of such ribozymes consist essentially of sequences defined in these Tables. By "consists essentially of" is meant that the active ribozyme contains an enzymatic center equivalent to those in the examples, and binding arms able to bind mRNA such that cleavage at the target site occurs. Other sequences may be present which do not interfere with such cleavage.

In another aspect of the invention, ribozymes that cleave target molecules and inhibit NF-κB activity are expressed from transcription units inserted into DNA, RNA, or viral vectors. Preferably, the recombinant vectors capable of expressing the ribozymes are locally delivered as described above, and transiently persist in target cells. Once expressed, the ribozymes cleave the target mRNA. The recombinant vectors are preferably DNA plasmids or adenovirus vectors. However, other mammalian cell vectors that direct the expression of RNA may be used for this purpose.

Other features and advantages of the invention will be apparent from the following description of the preferred embodiments thereof, and from the claims.

DESCRIPTION OF THE PREFERRED EMBODIMENTS

The drawings will first briefly be described.

Drawings:

FIG. 1 is a diagrammatic representation of the hammerhead ribozyme domain (SEQ ID No:2) known in the art.

FIG. 2a is a diagrammatic representation of the hammerhead ribozyme domain known in the art; FIG. 2b is a diagrammatic representation of the hammerhead ribozyme as divided by Uhlenbeck (1987, *Nature*, 327, 596–600) into a substrate and enzyme portion; FIG. 2c is a similar diagram showing the hammerhead divided by Haseloff and Gerlach (1988, *Nature*, 334, 585–591) into two portions; and FIG. 2d is a similar diagram showing the hammerhead divided by Jeffries and Symons (1989, *Nucl. Acids. Res.*, 17, 1371–1371) into two portions.

FIG. 5 is a representation of the general. structure of the VS RNA ribozyme domain (SEQ ID NO:6) known in the art.

Figure 1:
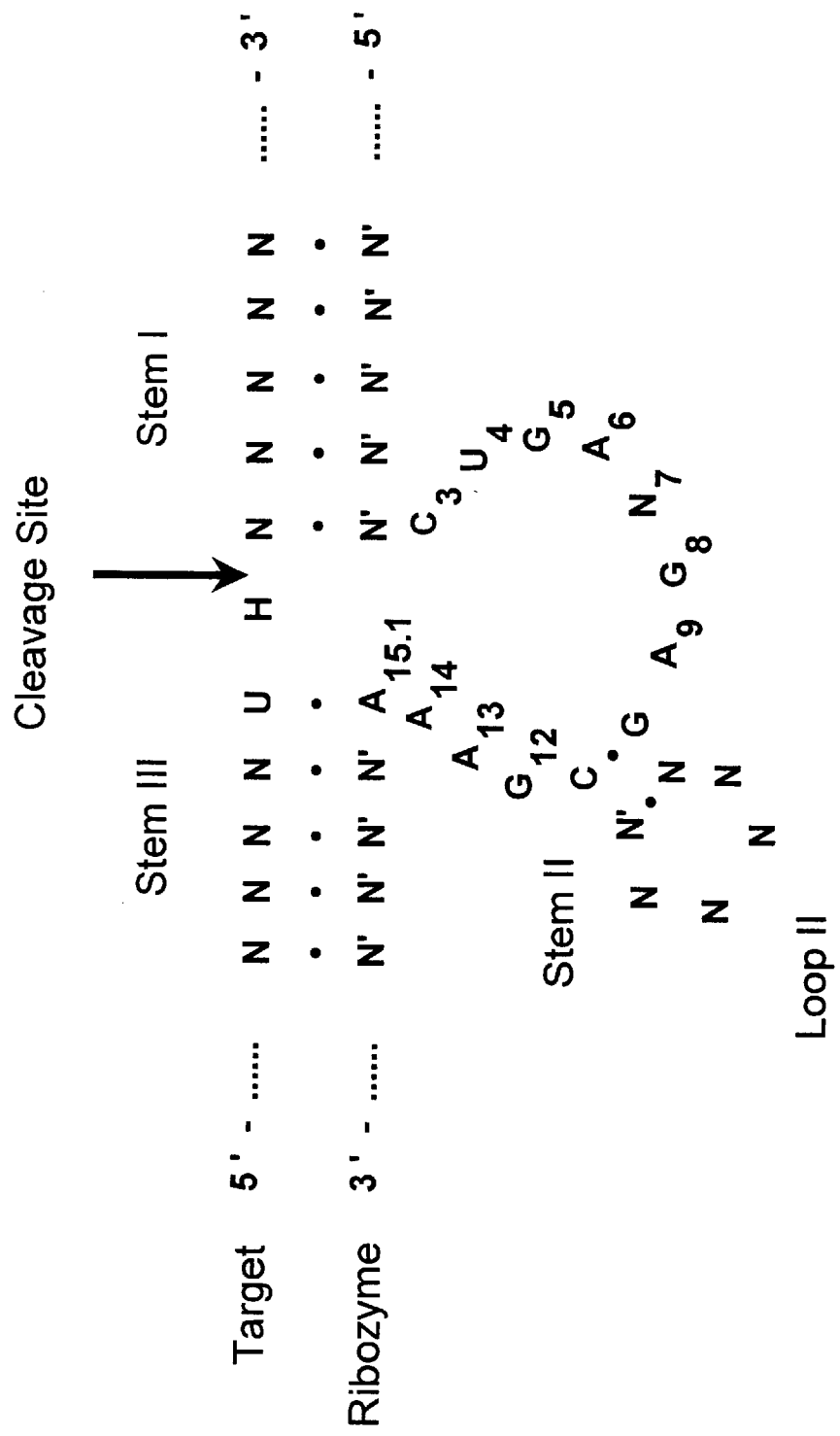

FIG. 6 is a schematic representation of an RNAseH accessibility assay. Specifically, the left side of FIG. 6 is a diagram of complementary DNA oligonucleotides bound to accessible sites on the target RNA. Complementary DNA oligonucleotides are represented by broad lines labeled A, B, and C. Target RNA is represented by the thin, twisted line. The right side of FIG. 6 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.

Ribozymes

Ribozymes of this invention block to some extent NF-κB expression and can be used to treat disease or diagnose such disease. Ribozymes will be delivered to cells in culture and to cells or tissues in animal models of restenosis, transplant rejection and rheumatoid arthritis. Ribozyme cleavage of relA mRNA in these systems may prevent inflammatory cell function and alleviate disease symptoms.

Target Sites

Targets for useful ribozymes can be determined as disclosed in Draper et al supra. Sullivan et al., supra, as well as by Draper et al., "Method and reagent for treatment of arthritic conditions U.S. Ser. No. 08/152,487, filed Nov. 12, 1993, and hereby incorporated by reference herein in totality. Rather than repeat the guidance provided in those documents here, below are provided specific examples of such methods, not limiting to those in the art. Ribozymes to such targets are designed as described in those applications and synthesized to be tested in vitro and in vivo, as also described. Such ribozymes can also be optimized and delivered as described therein. While specific examples to mouse and human RNA are provided, those in the art will recognize that the equivalent human RNA targets described can be used as described below. Thus, the same target may be used, but binding arms suitable for targeting human RNA sequences are present in the ribozyme. Such targets may also be selected as described below.

The sequence of human and mouse relA mRNA can be screened for accessible sites using a computer folding algorithm. Potential hammerhead or hairpin ribozyme cleavage sites were identified. These sites are shown in Tables II, III, and VI–VII. (All sequences are 5' to 3' in the tables.) While mouse and human sequences can be screened and ribozymes thereafter designed, the human targetted sequences are of most utility. However, as discussed in Stinchcomb et al. supra, mouse targetted ribozmes are useful to test efficacy of action of the ribozyme prior to testing in humans. The nucleotide base position is noted in the Tables as that site to be cleaved by the designated type of ribozyme. (In Table II, lower case letters indicate positions that are not conserved between the Human and the Mouse rel A sequences.)

Hammerhead ribozymes are designed that could bind and are individually analyzed by computer folding (Jaeger, J. A., et al., 1989, *Proc. Natl. Acad. Sci. USA*, 86, 7706–7710) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 bases on each arm are able to bind to, or otherwise interact with, the target RNA.

Referring to FIG. 6, mRNA is screened for accessible cleavage sites by the method described generally in Draper et al., WO/US93/04020 hereby incorporated by reference herein. Briefly, DNA oligonucleotides representing potential hammerhead ribozyme cleavage sites are synthesized. A polymerase chain reaction is used to generate a substrate for T7 RNA polymerase transcription from human or murine rel A cDNA clones. Labeled RNA transcripts are synthesized in vitro from the two templates. The oligonucleotides and the labeled transcripts are annealed, RNAseH is added and the mixtures are incubated for the designated times at 37° C. Reactions are stopped and RNA separated on sequencing polyacrylamide gels. The percentage of the substrate cleaved is determined by autoradiographic quantitation using a phosphor imaging system. From these data, hammerhead ribozyme sites are chosen as the most accessible.

Ribozymes of the hammerhead motif are designed to anneal to various sites in the mRNA message. The binding arms are complementary to the target site sequences described above. The ribozymes are chemically synthesized. The method of synthesis used follows the procedure for normal RNA synthesis as described in Usman, N.; Ogilvie, K. K.; Jiang, M.-Y.; Cedergren, R. J. 1987, *J. Am. Chem. Soc.*, 109, 7845–7854 and in Scaringe, S. A.; Franklyn, C.; Usman, N., 1990, *Nucleic Acids Res.*, 18, 5433–5441 and makes use of common nucleic acid protecting and coupling groups, such as dimethoxytrityl at the 5'-end, and phosphoramidites at the 3'-end. The average stepwise coupling yields were >98%. Inactive ribozymes were synthesized by substituting a U for $G_5$ and a U for $A_{14}$ (numbering from (Hertel, K. J., et al., 1992, *Nucleic Acids Res.*, 20, 3252)). Hairpin ribozymes are synthesized in two parts and annealed to reconstruct the active ribozyme (Chowrira, B. M. and Burke, J. M., 1992, *Nucleic Acids Res.*, 20, 2835–2840). All ribozymes are modified to enhance stability by modification of five ribonucleotides at both the 5' and 3' ends with 2'-O-methyl groups. Ribozymes are purified by gel electrophoresis using general methods or are purified by high pressure liquid chromatography (HPLC; See Usman et al., Synthesis, deprotection, analysis and purification of RNA and ribozymes, filed May, 18, 1994, U.S. Ser. No. 08/245,736 the totality of which is hereby incorporated herein by reference.) and are resuspended in water.

The sequences of the chemically synthesized ribozymes useful in this study are shown in Tables IV–VII. Those in the art will recognize that these sequences are representative only of many more such sequences where the enzymatic portion of the ribozyme (all but the binding arms) is altered to affect activity and may be formed of ribonucleotides or other nucleotides or non-nucleotides. Such ribozymes are equivalent to the ribozymes described specifically in the Tables.

Optimizing Ribozyme Activity

Figure 2:
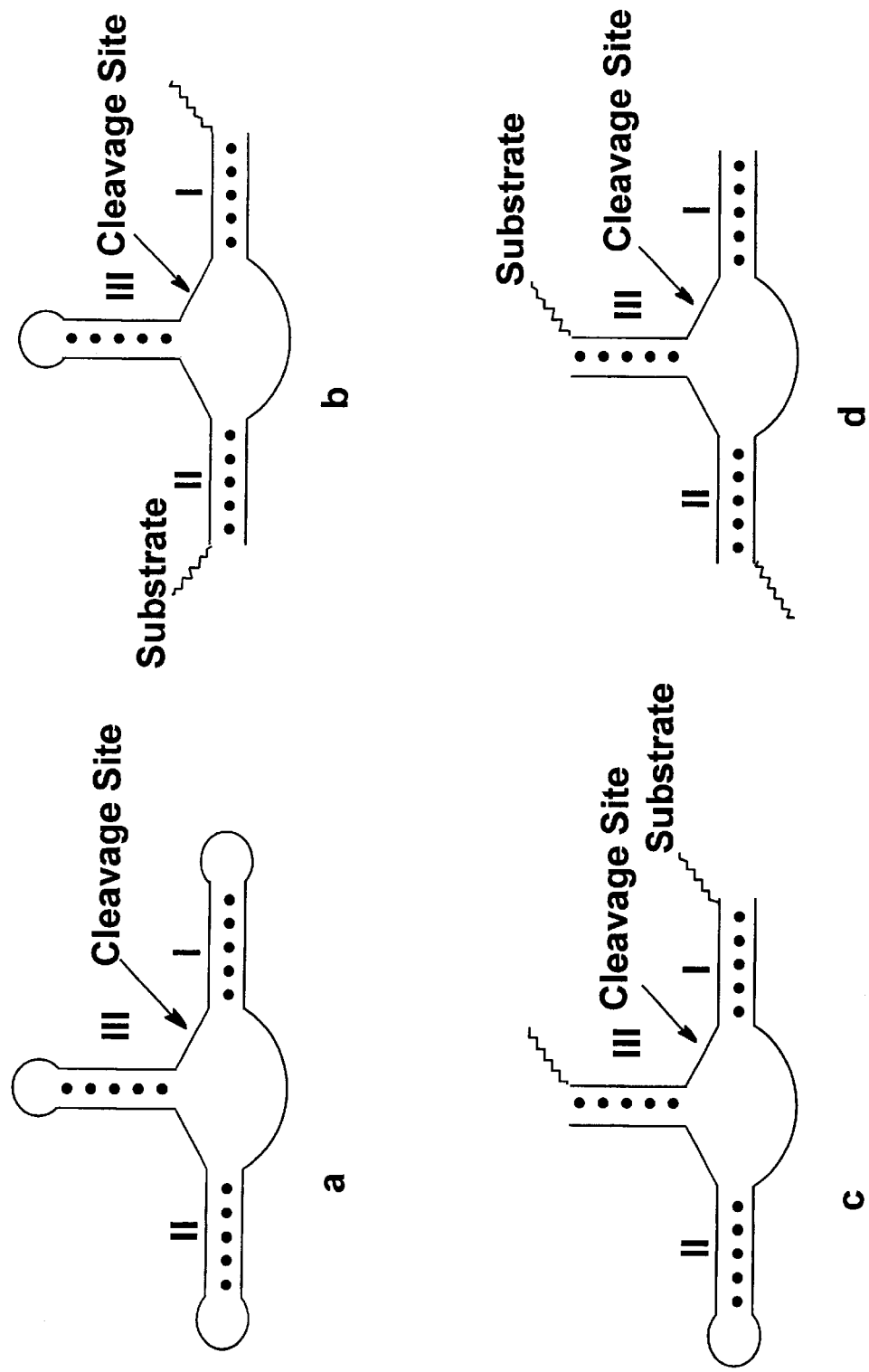
Figure 3:
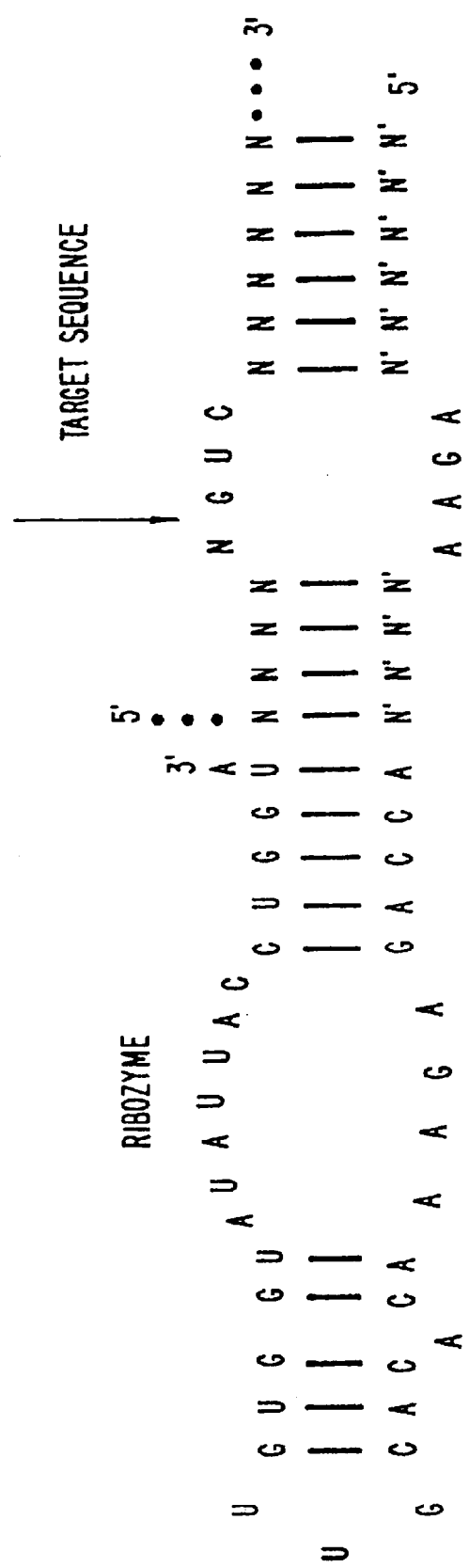
FIG. 3 is a representation of the general structure of the hairpin ribozyme domain (SEQ ID NO:4) known in the art.
Figure 4:
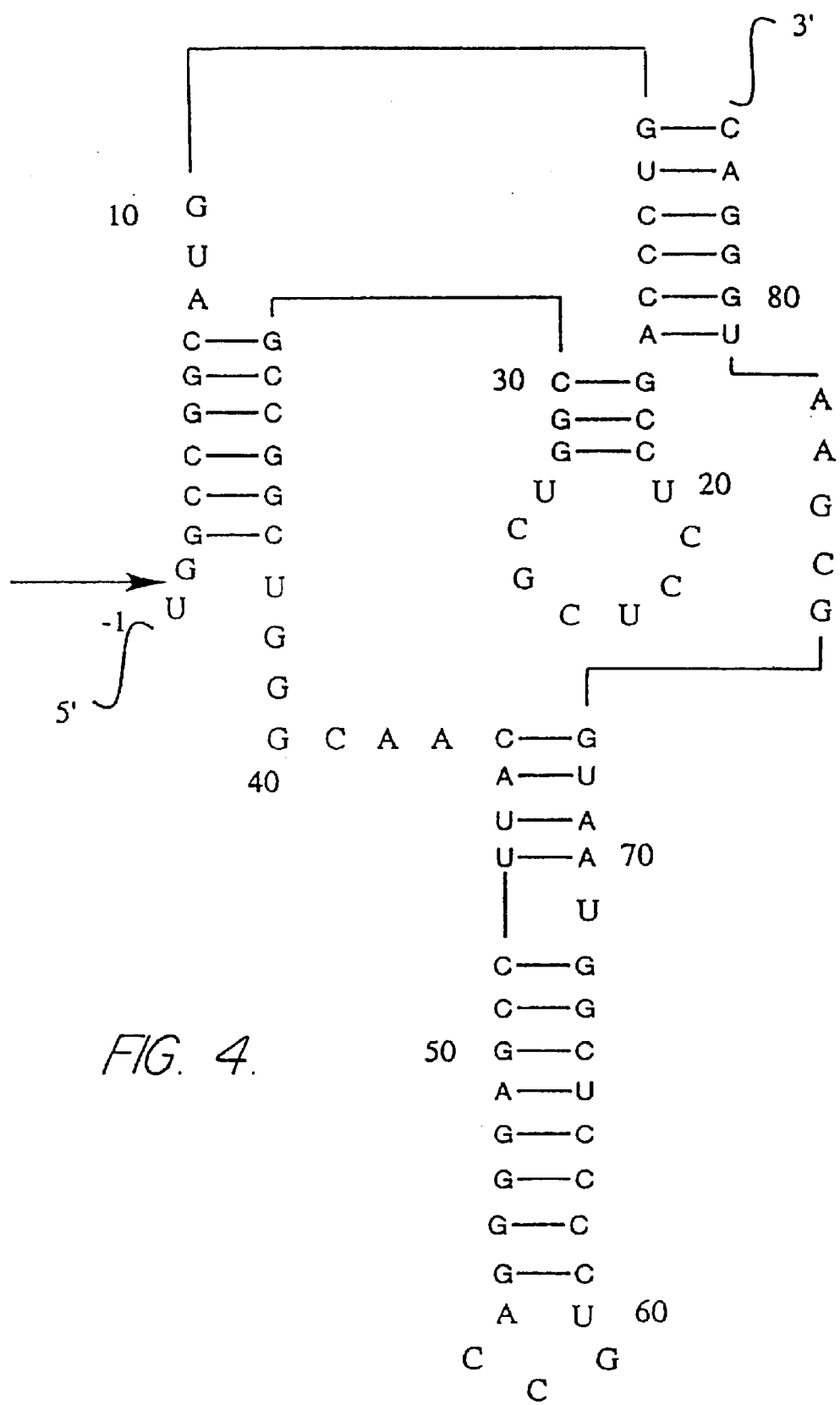
FIG. 4 is a representation of the general structure of the hepatitis delta virus ribozyme domain (SEQ ID NO:5) known in the art.

Ribozyme activity can be optimized as described by Stinchcomb et al., supra. The details will not be repeated here, but include altering the length of the ribozyme binding arms (stems I and III, see FIG. 2c), or chemically synthesizing ribozymes with modifications that prevent their degradation by serum ribonucleases (see e.g., Eckstein et al., International Publication No. WO 92/07065; Perrault et al., Nature 1990, 344:565; Pieken et al., Science 1991, 253:314; Usman and Cedergren, *Trends in Biochem. Sci.* 1992, 17:334; Usman et al., International Publication No. WO 93/15187; and Rossi et al., International Publication No. WO 91/03162, as well as Usman, N. et al. U.S. patent application Ser. No. 07/829,729, and Sproat, B. European Patent Application 92110298.4 which describe various chemical modifications that can be made to the sugar moieties of enzymatic RNA molecules. All these publications are hereby incorporated by reference herein.), modifications which enhance their efficacy in cells, and removal of stem II bases to shorten RNA synthesis times and reduce chemical requirements.

Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intrvascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan, et al., supra and Draper, et al., supra which have been incorporated by reference herein.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein, O. and Moss, B., 1990, *Proc. Natl. Acad. Sci. U S A,* 87, 6743–7; Gao, X. and Huang, L., 1993, *Nucleic Acids Res.,* 21, 2867–72; Lieber, A., et al., 1993, *Methods Enzymol.,* 217, 47–66; Zhou, Y., et al., 1990, *Mol. Cell. Biol.,* 10, 4529–37). Several investigators have demonstrated that ribozymes expressed from such promoters can function in mammalian cells (e.g. (Kashani-Sabet, M., et al., 1992, *Antisense Res. Dev.,* 2, 3–15; Ojwang, J. O., et al., 1992, *Proc. Natl. Acad. Sci. U S A,* 89, 10802–6; Chen, C. J., et al., 1992, *Nucleic Acids Res.,* 20, 4581–9; Yu, M., et al., 1993, *Proc. Natl. Acad. Sci. U S A,* 90, 6340–4; L'Huillier, P. J., et al., 1992, *Embo J.,* 11, 4411–8; Lisziewicz, J., et al., 1993, *Proc. Natl. Acad. Sci. U. S. A.,* 90, 8000–4)). The above ribozyme transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral vectors).

In a preferred embodiment of the invention, a transcription unit expressing a ribozyme that cleaves relA RNA is inserted into a plasmid DNA vector or an adenovirus DNA viral vector. Both vectors have been used to transfer genes to the intact vasculature or to joints of live animals (Willard, J. E., et al., 1992, *Circulation,* 86, I-473.; Nabel, E. G., et al., 1990, *Science,* 249, 1285–1288.) and both vectors lead to transient gene expression. The adenovirus vector is delivered as recombinant adenoviral particles. DNA may be delivered alone or complexed with vehicles (as described for RNA above). The DNA, DNA/vehicle complexes, or the recombinant adenovirus particles are locally administered to the site of treatment, e.g., through the use of an injection catheter, stent or infusion pump or are directly added to cells or tissues ex vivo.

EXAMPLE 1

NF-κB Hammerhead Ribozymes

By engineering ribozyme motifs we have designed several ribozymes directed against rel A mRNA sequences. These ribozymes are synthesized with modifications that improve their nuclease resistance. The ability of ribozymes to cleave relA target sequences in vitro is evaluated.

The ribozymes will be tested for function in vivo by analyzing cytokine-induced VCAM-1, ICAM-1, IL-6 and IL-8 expression levels. Ribozymes will be delivered to cells by incorporation into liposomes, by complexing with cationic lipids, by microinjection, or by expression from DNA vectors. Cytokine-induced VCAM-1, ICAM-1, IL-6 and IL-8 expression will be monitored by ELISA, by indirect immunofluoresence, and/or by FACS analysis. Rel A mRNA levels will be assessed by Northern analysis, RNAse protection or primer extension analysis or quantitative RT-PCR. Activity of NF-κB will be monitored by gel-retardation assays. Ribozymes that block the induction of NF-κB activity and/or rel A mRNA by more than 50% will be identified.

RNA ribozymes and/or genes encoding them will be locally delivered to transplant tissue ex vivo in animal models. Expression of the ribozyme will be monitored by its ability to block ex vivo induction of VCAM-1, ICAM-1, IL-6 and IL-8 mRNA and protein. The effect of the anti-rel A ribozymes on graft rejection will then be assessed. Similarly, ribozymes will be introduced into joints of mice with collagen-induced arthritis or rabbits with Streptococcal cell wall-induced arthritis. Liposome delivery, cationic lipid delivery, or adeno-associated virus vector delivery can be used. One dose (or a few infrequent doses) of a stable anti-relA ribozyme or a gene construct that constitutively expresses the ribozyme may abrogate inflammatory and immune responses in these diseases.

Uses

A therapeutic agent that inhibits cytokine gene expression, inhibits adhesion molecule expression, and mimics the anti-inflammatory effects of glucocorticoids (without inducing steroid-responsive genes) is ideal for the treatment of inflammatory and autoimmune disorders. Disease targets for such a drug are numerous. Target indications and the delivery options each entails are summarized below. In all cases, because of the potential immunosuppressive properties of a ribozyme that cleaves rel A mRNA, uses are limited to local delivery, acute indications, or ex vivo treatment.

Rheumatoid arthritis (RA).

Due to the chronic nature of RA, a gene therapy approach is logical. Delivery of a ribozyme to inflamed joints is mediated by adenovirus, retrovirus, or adeno-associated virus vectors. For instance, the appropriate adenovirus vector can be administered by direct injection into the synovium: high efficiency of gene transfer and expression for several months would be expected (B. J. Roessler, E. D. Allen, J. M. Wilson, J. W. Hartman, B. L. Davidson, J. Clin. Invest. 92, 1085–1092 (1993)). It is unlikely that the course of the disease could be reversed by the transient, local administration of an anti-inflammatory agent. Multiple administrations may be necessary. Retrovirus and adeno-associated virus vectors would lead to permanent gene transfer and expression in the joint. However, permanent expression of a potent anti-inflammatory agent may lead to local immune deficiency.

Restenosis.

Expression of NF-κB in the vessel wall of pigs causes a narrowing of the luminal space due to excessive deposition of extracellular matrix components. This phenotype is similar to matrix deposition that occurs subsequent to coronary angioplasty. In addition, NF-κB is required for the expression of the oncogene c-myb (F. A. La Rosa, J. W. Pierce, G. E. Soneneshein, Mol. Cell. Biol. 14, 1039–44 (1994)). Thus NF-κB induces smooth muscle proliferation and the expression of excess matrix components: both processes are thought to contribute to reocclusion of vessels after coronary angioplasty.

Transplantation.

NF-κB is required for the induction of adhesion molecules (Eck et al., supra, K. O'Brien, et al., J. Clin. Invest. 92, 945–951 (1993)) that function in immune recognition and inflammatory responses. At least two potential modes of treatment are possible. In the first, transplanted organs are treated ex vivo with ribozymes or ribozyme expression vectors. Transient inhibition of NF-κB in the transplanted endothelium may be sufficient to prevent transplant-associated vasculitis and may significantly modulate graft rejection. In the second, donor B cells are treated ex vivo with ribozymes or ribozyme expression vectors. Recipients would receive the treatment prior to transplant. Treatment of a recipient with B cells that do not express T cell co-stimulatory molecules (such as ICAM-1, VCAM-1, and/or B7 an B7-2) can induce antigen-specific anergy. Tolerance to the donor's histocompatibility antigens could result; potentially, any donor could be used for any transplantation procedure.

Asthma.

Granulocyte macrophage colony stimulating factor (GM-CSF) is thought to play a major role in recruitment of eosinophils and other inflammatory cells during the late phase reaction to asthmatic trauma. Again, blocking the local induction of GM-CSF and other inflammatory mediators is likely to reduce the persistent inflammation observed in chronic asthmatics. Aerosol delivery of ribozymes or adenovirus ribozyme expression vectors is a feasible treatment.

Gene Therapy.

Immune responses limit the efficacy of many gene transfer techniques. Cells transfected with retrovirus vectors have short lifetimes in immune competent individuals. The length of expression of adenovirus vectors in terminally differentiated cells is longer in neonatal or immune-compromised animals. Insertion of a small ribozyme expression cassette that modulates inflammatory and immune responses into existing adenovirus or retrovirus constructs will greatly enhance their potential.

Thus, ribozymes of the present invention that cleave rel A mRNA and thereby NF-κB activity have many potential therapeutic uses, and there are reasonable modes of delivering the ribozymes in a number of the possible indications. Development of an effective ribozyme that inhibits NF-κB function is described above; available cellular and activity assays are number, reproducible, and accurate. Animal models for NF-κB function (Kitajima, et al., supra) and for each of the suggested disease targets exist and can be used to optimize activity.

Diagnostic Uses

Ribozymes of this invention may be used as diagnostic tools to examine genetic drift and mutations within diseased cells. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNA associated with an NF-κB related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., NF-κB) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Other embodiments are within the following claims.

TABLE II

Mouse rel A HH Target sequence

| nt. Pos. | HH Target Sequence | Seq. ID No. |
|---|---|---|
| 19 | AAUGGCU a caCaGgA | 7 |
| 22 | aGCUCcU a cGUgGUG | 8 |
| 26 | CcUCcaU u GcGgACa | 9 |
| 93 | GAUCUGU U uCCCCUC | 10 |
| 94 | uAUCUGUU u CCCCUCA | 11 |
| 100 | UuCCCCU C AUCUUuC | 12 |
| 103 | CCCUCAU C UuuCCcu | 13 |
| 105 | CUCAUCU U uCCcuCA | 14 |
| 106 | UCACUU u CccuCAG | 15 |
| 129 | CAGGCuU C UGGgCCU | 16 |
| 138 | GGgCCuU A UGUGGAG | 17 |
| 148 | UGGAGAU C AucGAaC | 18 |
| 151 | AGAUCAU c GaaCAGC | 19 |
| 180 | AUGGaU U CCGCUAu | 20 |
| 181 | UGCGaUU C CGCUAuA | 21 |
| 186 | UUCCGCU A uAAaUGC | 22 |
| 204 | GGGCGCU C aGCGGGC | 23 |
| 217 | GCAGuAU u CcuGGCG | 24 |
| 239 | CACAGAU A CCACCAA | 25 |

TABLE II-continued

Mouse rel A HH Target sequence

| nt. Pos. | HH Target Sequence | Seq. ID No. |
|---|---|---|
| 262 | CCACCAU C AAGAUCA | 26 |
| 268 | CGaAUCU C AAUGGCU | 27 |
| 276 | AAUGGCU A CACAGGA | 28 |
| 301 | UuCGaAU C UCCCUGG | 29 |
| 303 | CGUCU C CCUGGUC | 30 |
| 310 | CCCUGGU C ACCAAGG | 31 |
| 323 | GGcCCCU C CUCcuga | 32 |
| 326 | uCCaCCU C ACCGGCC | 33 |
| 335 | CCGGCCU C AuCCaCA | 34 |
| 349 | AuGAaCU U GugGGgA | 35 |
| 352 | AGaUcaU c GaACAGc | 36 |
| 375 | GAUGGCU a CUAUGAG | 37 |
| 376 | AUGGucU C UccGgaG | 38 |
| 378 | GGCUaCU A UGAGGCU | 39 |
| 391 | CUGAcCU C UGCCCaG | 40 |
| 409 | GCaGuAU C CauAGcU | 41 |
| 416 | CCgCAGU a UCCAuAg | 42 |
| 417 | CAuAGcU U CCAGAAC | 43 |
| 418 | AuAGcUU C CAGAACC | 44 |
| 433 | UGGGgAU C CAGUGUG | 45 |
| 795 | GGCUCCU U UUCuCAA | 46 |
| 796 | GCUCCUU U UcuCAAG | 47 |
| 797 | CUCCUUU U CuCAAGC | 48 |
| 798 | UCCUUUU C uCAAGCU | 49 |
| 829 | UGGCCAU U GUGUUCC | 50 |
| 834 | AUUGUGU U CCGGACu | 51 |
| 835 | UUGUGUU C CGGACuC | 52 |
| 845 | GACuCCU C CgUACGC | 53 |
| 849 | CCUCCgU A CGCcGAC | 54 |
| 872 | cCAGGCU C CUGUuCG | 55 |
| 883 | UuCGaGU C UCCAUGC | 56 |
| 885 | CGaGUCU C CAUGCAG | 57 |
| 905 | GCGGCCU U CUGAUCG | 58 |
| 906 | CGGCCUU C uGAuCGc | 59 |
| 919 | GcGAGCU C AGUGAGC | 60 |
| 936 | AUGGAgU U CCAGUAC | 61 |
| 937 | UGGAgUU C CAGUACu | 62 |
| 942 | UUCCAGU A CuUGCCA | 63 |
| 953 | GCCuCAU c CaCAuGA | 64 |
| 962 | AGAuGAU C GcCACCG | 65 |
| 965 | CagUacU u gCCaGAc | 66 |
| 973 | ACCGGAU U GaaGAGA | 67 |
| 986 | GAgACcU u CAAGagu | 68 |
| 996 | AGGACcU A UGAGACC | 69 |
| 1005 | GAGACCU U CAAGAGu | 70 |
| 1006 | AGACCUU C AACAGUA | 71 |
| 1015 | AGAGuAU C AUGAAGA | 72 |
| 1028 | GAAGAGU C CUUUCAa | 73 |
| 1031 | GAGUCCU U UCAauGG | 74 |
| 1032 | AGUCCUU U CaauGGA | 75 |
| 1033 | GUCCUUU C AauGGAC | 76 |
| 1058 | CCGGCCU C CaaCcCG | 77 |
| 1064 | UaCACCU u GaucCAa | 78 |
| 1072 | GgCGUAU U GCUGUGC | 79 |
| 1082 | UGUGCCU a CCCGaAa | 80 |
| 1083 | aaGCCUU C CCGGaAGu | 81 |
| 1092 | CCaAaCU C AaCUUCU | 82 |
| 1097 | CUCAaCU U CUGUCCC | 83 |
| 1098 | UCAaCUU C UGUCCCC | 84 |
| 1102 | CUUCUGU C CCCAAGC | 85 |
| 1125 | CAGCCCU A caCCUUc | 86 |
| 1127 | GCCaUAU a gCcUUAC | 87 |
| 1131 | cAUCCCU c agCacCA | 88 |
| 1132 | AcaCCUU c cCagCAU | 89 |
| 1133 | UCCaUcU c CagCuUC | 90 |
| 1137 | UUUACuU u AgCgCgc | 91 |
| 1140 | cCagCAU C CCUCAGC | 92 |
| 1153 | CCACCAU C AACUuUG | 93 |
| 1158 | AUCAACU u UGAUGAG | 94 |
| 1680 | GAAGACU U CUCCUCC | 95 |
| 1681 | AAGACUU C UCCUCCA | 96 |
| 1683 | GACUUCU C CUCCAUU | 97 |
| 1686 | UUCUCCU C CAUUGCG | 98 |
| 1690 | CCUCCAU U GCGGACA | 99 |

TABLE II-continued

Mouse rel A HH Target sequence

| nt. Pos. | HH Target Sequence | Seq. ID No. |
|---|---|---|
| 1704 | AUGGACU U CUCuGCu | 100 |
| 1705 | UCGACUU C UCuGCuC | 101 |
| 1707 | GACUUCU C uGCuCUu | 102 |
| 1721 | uuUGAGU C AGAUCAG | 103 |
| 1726 | GUCAGAU C AGCUCCU | 104 |
| 1731 | AUCAGCU C CUAAGGu | 105 |
| 1734 | ACCUCCU A AGGuGcU | 106 |
| 1754 | CaGugCU C CCaAGAG | 107 |
| 467 | cCAGGCU c cuguUCg | 108 |
| 469 | AaGCCAU u AGcCAGC | 109 |
| 473 | UuUgAGU C AGauCAg | 110 |
| 481 | AGCaAGU C CAGACCA | 111 |
| 501 | AACCCCU U UCAcGUU | 112 |
| 502 | ACCCCUU u CAcGUUC | 113 |
| 508 | UuCAcGU U CCUAUAG | 114 |
| 509 | uCAcGUU C CUAUAGA | 115 |
| 512 | cGUUCCU A UAGAgGA | 116 |
| 514 | UUCCUAU C GAgGAGC | 117 |
| 534 | GGGGACU A uGACuUG | 118 |
| 556 | UGCGcCU C UGCUUCC | 119 |
| 561 | CUCUGCU U CCAGGUG | 120 |
| 562 | UCUGCUU C CAGGUGA | 121 |
| 585 | aAgCCAU u AGcCAGc | 122 |
| 598 | GGCCCCU C CUCCUGa | 123 |
| 613 | CcCCUGU C CUcuCaC | 124 |
| 616 | CUGUCCU c uCaCAUC | 125 |
| 617 | gucCCUU C CUCAgCC | 126 |
| 620 | CCUUCCU C AgCCaug | 127 |
| 623 | UCCUgcU u CCAUCUc | 128 |
| 628 | AUCCgAU u UUUGAuA | 129 |
| 630 | CCgAUuU U UGAuAAc | 130 |
| 631 | CgAUuUU U GAuAAcC | 131 |
| 638 | UGgCcAU u GUGuuCC | 132 |
| 661 | CCGAGCU C AAGAUCU | 133 |
| 667 | UCAAGAU C UGCCGAG | 134 |
| 687 | CGgAACU C UGGgAGC | 135 |
| 700 | GCUGCCU C GGUGGGG | 136 |
| 715 | AUGAGAU C UUCuUgC | 137 |
| 717 | GAGAUCU U CuUgCUG | 138 |
| 718 | AGAUCUU C uUgCUGU | 139 |
| 721 | UucUCCU c CauUGcG | 140 |
| 751 | AaGACAU U GAGGUGU | 141 |
| 759 | GAGGUGU A UUUCACG | 142 |
| 761 | GGUGUAU U UCACGGG | 143 |
| 762 | GUGUAUU U CACGGGA | 144 |
| 763 | UGUAUUU C ACGGGAC | 145 |
| 792 | CGAGGCU C CUUUUCu | 146 |
| 1167 | GAUGAGU U UuCCcCC | 147 |
| 1168 | AUGAGUU U uCCcCCA | 148 |
| 1169 | UGAGUUU u CCcCCAU | 149 |
| 1182 | AUGcUGU U aCCaUCa | 150 |
| 1183 | UgCUGUU a CCaUCaG | 151 |
| 1184 | GGccccU C CUcCUGa | 152 |
| 1187 | GUccCuU c CUcaGCc | 153 |
| 1188 | UUaCCaU C aGGGCAG | 154 |
| 1198 | GGgAGuU u AGuCuGa | 155 |
| 1209 | CAGCCCU a caCCUUc | 156 |
| 1215 | cuGGCCU U aGCaCCG | 157 |
| 1229 | GGuCCCU u CCucAGc | 158 |
| 1237 | CCCAgCU C CUGCCCC | 159 |
| 1250 | CCAGcCU C CAGgCuC | 160 |
| 1268 | CCCaCCU C CuGCCcc | 161 |
| 1279 | CCAUGGU c cCuuCcu | 162 |
| 1281 | gUGGgcU C ACCUgcG | 163 |
| 1286 | AUgAGuU u UccCCCA | 164 |
| 1309 | CuCCUGU u CgAGUCu | 165 |
| 1315 | cCCCAGU u CUAaCCC | 166 |
| 1318 | CAGUuCU A aCCCCgG | 167 |
| 1331 | gGGuCCU C CcCAGuC | 168 |
| 1334 | CuuUuCU C AaGCUGa | 169 |
| 1389 | ACGCUGU C gGAaGCC | 170 |
| 1413 | CUGCAGU U UCAUGcU | 171 |
| 1414 | UCCAGUU U GAUGcUG | 172 |
| 1437 | GGGGCCU U GCUUGGC | 173 |
| 1441 | CCUUGCU U GCCAACA | 174 |
| 1467 | GgaGUGU U CACACAC | 175 |
| 1468 | gaCUGUU C ACAGACC | 176 |
| 1482 | CUCGCAU C uGUgGAC | 177 |
| 1486 | CUUCgGU a GggAACU | 178 |
| 1494 | GACAACU C aGAGUUU | 179 |
| 1500 | UCaGAGU U UCAGCAC | 180 |
| 1501 | CaGAGUU U CAGCAGC | 181 |
| 1502 | aCAGUUU C ACCAGCU | 182 |
| 1525 | gGUGCAU c CCUGUGu | 183 |
| 1566 | AUGGAGU A CCCUGAa | 184 |
| 1577 | UGAaGCU A UAACUCG | 185 |
| 1579 | AaGCUAU A ACUCGCC | 186 |
| 1583 | UAUAACU C GCCUgGU | 187 |
| 1588 | CUCuCCU A GaGAggG | 188 |
| 1622 | CCCAGCU C CUGCcCC | 189 |
| 1628 | UCCUCCU u CggUaGG | 190 |
| 1648 | CGGGGCU u CCCAAUG | 191 |
| 1660 | cUGaCCU C ugccCAG | 192 |
| 1663 | cuCUgCU U cCAGGUG | 193 |
| 1664 | uCUgCUU c CAGGuGA | 194 |
| 1665 | CUCgcUU u cGGAGgU | 195 |

TABLE III

Human rel A HH Target Sequences

| nt. Pos. | HH Target Sequence | Seq. ID No. |
|---|---|---|
| 19 | AAUGGCU C GUCUGUA | 196 |
| 22 | GGCUCGU C UGUAGUG | 197 |
| 26 | CGUCUGU A GUGCACG | 198 |
| 93 | GAACUGU U CCCCCUC | 199 |
| 94 | AACUGUU C CCCCUCA | 200 |
| 100 | UCCCCCU C AUCUUCC | 201 |
| 103 | CCCUCAU C UUCCUGA | 202 |
| 105 | CUCAUCU U CCCGGCA | 203 |
| 106 | UCAUCUU C CCGGCAG | 204 |
| 129 | CAGGCCU C UGGCCCC | 205 |
| 138 | GGCCCCU A UGGGAAC | 206 |
| 148 | UGGAGAU C AUUGAGC | 207 |
| 151 | AGAUCAU U GAGCAGC | 208 |
| 180 | AUGCGCU U CCGCUAC | 209 |
| 181 | UGCGCUU C CGCUACA | 210 |
| 186 | UUCCGCU A CAAGUGC | 211 |
| 204 | GGGCGCU C CGCGGGC | 212 |
| 217 | GCAGCAU C CCAGGCG | 213 |
| 239 | CACAGAU A CCACCAA | 214 |
| 262 | CCACCAU C AAGAUCA | 215 |
| 268 | UCAAGAU C AAUGGCU | 216 |
| 276 | AAUGGCU A CACAGGA | 217 |
| 301 | UGCGCAU C UCCCUGG | 218 |
| 303 | CGCAUCU C CCUGGUC | 219 |
| 310 | CCCUGGU C ACCAAGG | 220 |
| 323 | GGACCCU C CUCACCG | 221 |
| 326 | CCCUCCU C ACCGGCC | 222 |
| 335 | CCGGCCU C ACCCCCA | 223 |
| 349 | ACGAGCU U GUAGGAA | 224 |
| 352 | AGCUUGU A GGAAAGG | 225 |
| 375 | GAUGGCU U CUAUGAG | 226 |
| 376 | AUGGCUU C UAUGAGG | 227 |
| 378 | GGCUUCU A UGAGGCU | 228 |
| 391 | CUGAGCU C UGCCCGG | 229 |
| 409 | GCUGCAU C CACAGUU | 230 |
| 416 | CCACAGU U UCCAGAA | 231 |
| 417 | CACAGUU U CCAGAAC | 232 |
| 418 | ACAGUUU C CAGAACC | 233 |
| 433 | UGGGAAU C CAGUGUG | 234 |
| 795 | GGCUCCU U UUCGCAA | 235 |
| 796 | GCUCCUU U UCGCAAG | 236 |
| 797 | CUCCUUU U CGCAAGC | 237 |

TABLE III-continued

Human rel A HH Target Sequences

| nt. Pos. | HH Target Sequence | Seq. ID No. |
|---|---|---|
| 798 | UCCUUUU C GCAAGCU | 238 |
| 829 | UGGCCAU U GUGUUCC | 239 |
| 834 | AUUGUGU U CCGGACC | 240 |
| 835 | UUGUGUU C CGGACCC | 241 |
| 845 | GACCCCU C CCUACGC | 242 |
| 849 | CCUCCCU A CGCAGAC | 243 |
| 872 | GCAGGCU C CUGUGCG | 244 |
| 883 | UGCGUGU C UCCAUGC | 245 |
| 885 | CGUGUCU C CAUGCAG | 246 |
| 905 | GCGGCCU U CCGACCG | 247 |
| 906 | CGGCCUU C CGACCGG | 248 |
| 919 | GGGAGCU C AGUGAGC | 249 |
| 936 | AUGGAAU U CCAGUAC | 250 |
| 937 | UGGAAUU C CAGUACC | 251 |
| 942 | UUCCAGU A CCUGCCA | 252 |
| 953 | GCCAGAU A CAGACGA | 253 |
| 962 | AGACGAU C GUCACCG | 254 |
| 965 | CGAUCGU C ACCGGAU | 255 |
| 973 | ACCGGAU U GAGGAGA | 256 |
| 986 | GAAACGU A AAAGGAC | 257 |
| 996 | AGGACAU A UGAGACC | 258 |
| 1005 | GAGACCU U CAAGAGC | 259 |
| 1006 | AGACCUU C AAGAGCA | 260 |
| 1015 | AGAGCAU C AUGAAGA | 261 |
| 1028 | GAAGAGU C CUUUCAG | 262 |
| 1031 | GAGUCCU U UCAGCGG | 263 |
| 1032 | AGUCCUU U CAGCGGA | 264 |
| 1033 | GUCCUUU C AGCGGAC | 265 |
| 1058 | CCGGCCU C CACCUCG | 266 |
| 1064 | UCCACCU C GACGCAU | 267 |
| 1072 | GACGCAU U GCUGUGC | 268 |
| 1082 | UGUGCCU U CCCGCAG | 269 |
| 1083 | GUGCCUU C CCGCAGC | 270 |
| 1092 | CGCAGCU C AGCUUCU | 271 |
| 1097 | CUCAGCU U CUGUCCC | 272 |
| 1098 | UCAGCUU C UGUCCCC | 273 |
| 1102 | CUUCUGU C CCCAAGC | 274 |
| 1125 | CAGCCCU A UCCCUUU | 275 |
| 1127 | GCCCUAU C CCUUUAC | 276 |
| 1131 | UAUCCCU U UACGUCA | 277 |
| 1132 | AUCCCUU U ACGUCAU | 278 |
| 1133 | UCCCUUU A CGUCAUC | 279 |
| 1137 | UUUACGU C AUCCCUG | 280 |
| 1140 | ACGUCAU C CCUGAGC | 281 |
| 1153 | GCACCAU C AACUAUG | 282 |
| 1158 | AUCAACU A UGAUGAG | 283 |
| 1680 | GAAGACU U CUCCUCC | 284 |
| 1681 | AAGACUU C UCCUCCA | 285 |
| 1683 | GACUUCU C CUCCAUU | 286 |
| 1686 | UUCUCCU C CAUUGCG | 287 |
| 1690 | CCUCCAU U GCGGACA | 288 |
| 1704 | AUGGACU U CUCAGCC | 289 |
| 1705 | UGGACUU C UCAGCCC | 290 |
| 1707 | GACUUCU C AGCCCUG | 291 |
| 1721 | GCUGAGU C AGAUCAG | 292 |
| 1726 | GUCAGAU C AGCUCCU | 293 |
| 1731 | AUCAGCU C CUAAGGG | 294 |
| 1734 | AGCUCCU A AGGGGGU | 295 |
| 1754 | CUGCCCU C CCCAGAG | 296 |
| 467 | GCAGGCA U CAGUCA | 297 |
| 469 | AGGCUAU C AGUCAGC | 298 |
| 473 | UAUCAGU C AGCGCAU | 299 |
| 481 | AGCGCAU C CAGACCA | 300 |
| 501 | AACCCCU U CCAAGUU | 301 |
| 502 | ACCCCUU C CAAGUUC | 302 |
| 508 | UCCAAGU U CCUAUAG | 303 |
| 509 | CCAAGUU C CUAUAGA | 304 |
| 512 | AGUUCCU A UAGAAGA | 305 |
| 514 | UUCCUAU A GAAGAGC | 306 |
| 534 | GGGGACU A CGACCUG | 307 |
| 556 | UGCGGCU U UGCUUCC | 308 |
| 561 | CUCUGCU U CCAGGUG | 309 |
| 562 | UCUGCUU C CAGGUGA | 310 |
| 585 | GACCCAU C AGGCAGG | 311 |

TABLE III-continued

Human rel A HH Target Sequences

| nt. Pos. | HH Target Sequence | Seq. ID No. |
|---|---|---|
| 598 | GGCCCCU C CGCCUGC | 312 |
| 613 | CGCCUGU C CUUCCUC | 313 |
| 616 | CUGUCCU U CCUCAUC | 314 |
| 617 | UGUCCUU C CUCAUCC | 315 |
| 620 | CCUUCCU C AUCCCAU | 316 |
| 623 | UCCUCAU & CCAUCUU | 317 |
| 628 | AUCCCAU C UUUGACA | 318 |
| 630 | CCCAUCU U UGACAAU | 319 |
| 631 | CCAUCUU U GACAAUC | 320 |
| 638 | UGACAAU C GUGCCCC | 321 |
| 661 | CCGAGCU C AAGAUCU | 322 |
| 667 | UCAAGAU C UGCCGAG | 323 |
| 687 | CGAAACU C UGGCAGC | 324 |
| 700 | GCUGCCU C GGUGGGG | 325 |
| 715 | AUGAGAU C UUCCUAC | 326 |
| 717 | GAGAUCU U CCUACUG | 327 |
| 718 | AGAUCUU C CUACUGU | 328 |
| 721 | UCUUCCU A CUGUGUG | 329 |
| 751 | AGGACAU U GAGGUGU | 330 |
| 759 | GAGGUGU A UUUCACG | 331 |
| 761 | GGUGUAU U UCACGGG | 332 |
| 762 | GUGUAUU U CACGGGA | 333 |
| 763 | UGUAUUU C ACGGGAC | 334 |
| 792 | CGAGGCU C CUUUUCG | 335 |
| 1167 | GAUGAGU U UCCCACC | 336 |
| 1168 | AUGAGUU U CCCACCA | 337 |
| 1169 | UGAGUUU C CCACCAU | 338 |
| 1182 | AUGGUGU U UCCUUCU | 339 |
| 1183 | UGGUGUU U CCUUCUG | 340 |
| 1184 | GGUGUUU C CUUCUGG | 341 |
| 1187 | GUUUCCU U CUGGGCA | 342 |
| 1188 | UUUCCUU C UGGGCAG | 343 |
| 1198 | GGCAGAU C AGCCAGG | 344 |
| 1209 | CAGGCCU C GGCCUUG | 345 |
| 1215 | UCGGCCU U GGCCCCG | 346 |
| 1229 | GGCCCCU C CCCAAGU | 347 |
| 1237 | CCCAAGU C CUGCCCC | 348 |
| 1250 | CCAGGCU C CAGCCCC | 349 |
| 1268 | CCCUGCU C CAGCCAU | 350 |
| 1279 | CCAUGGU A UCAGCUC | 351 |
| 1281 | AUGGUAU C AGCUCUG | 352 |
| 1286 | AUCAGCU C UGGCCCA | 353 |
| 1309 | CCCCUGU C CCAGUCC | 354 |
| 1315 | UCCCAGU C CUAGCCC | 355 |
| 1318 | CAGUCCU A GCCCCAG | 356 |
| 1331 | AGGCCCU C CUCAGGC | 357 |
| 1334 | CCCUCCU C AGGCUGU | 358 |
| 1389 | ACGCUGU C AGAGGCC | 359 |
| 1413 | CUGCAGU U UGAUGAU | 360 |
| 1414 | UGCAGUU U GAUGAUG | 361 |
| 1437 | GGGGCCU U GCUUGGC | 362 |
| 1441 | CCUUGCU U GGCAACA | 363 |
| 1467 | GCUGUGU U CACAGAC | 364 |
| 1468 | CUGUGUU C ACAGACC | 365 |
| 1482 | CUGGCAU C CGUCGAC | 366 |
| 1486 | CAUCCGU C GACAACU | 367 |
| 1494 | GACAACU C CGAGUUU | 368 |
| 1500 | UCCGAGU U UCAGCAG | 369 |
| 1501 | CCGAGUU U CAGCAGC | 370 |
| 1502 | CGAGUUU C AGCAGCU | 371 |
| 1525 | AGGGCAU A CCUGUGG | 372 |
| 1566 | AUGGAGU A CCCUGAG | 373 |
| 1577 | UGAGGCU A UAACUCG | 374 |
| 1579 | AGGCUAU A ACUCGCC | 375 |
| 1583 | UAUAACU C GCCUAGU | 376 |
| 1588 | CUCGCCU A GUGACAG | 377 |
| 1622 | CCCAGCU C CUGCUCC | 378 |
| 1628 | UCCUGCU C CACUGGG | 379 |
| 1648 | CGGGGCU U CCCAAUG | 380 |
| 1660 | AUGGCCU C CUUUCAG | 381 |
| 1663 | GCCUCCU U UCAGGAG | 382 |
| 1664 | CCUCCUU U CAGGAGA | 383 |
| 1665 | CUCCUUU C AGGAGAU | 384 |

TABLE IV

Mouse rel A HH Ribozyme Sequences

| nt. Sequence | HH Ribozyme Sequence | Seq. ID No. |
|---|---|---|
| 19 | UCCUGUG CUGAUGAGGCCGAAAGGCCGAA AGCCAUU | 385 |
| 22 | CACCACG CUGAUGAGGCCGAAAGGCCGAA AGGAGCU | 386 |
| 26 | UGUCCGC CUGAUGAGGCCGAAAGGCCGAA AUGGAGG | 387 |
| 93 | GAGGGGA CUGAUGAGGCCGAAAGGCCGAA ACAGAUC | 388 |
| 94 | UGAGGGG CUGAUGAGGCCGAAAGGCCGAA AACAGAU | 389 |
| 100 | GAAAGAU CUGAUGAGGCCGAAAGGCCGAA AGGGGAA | 390 |
| 103 | AGGGAAA CUGAUGAGGCCGAAAGGCCGAA AUGAGGG | 391 |
| 105 | UGAGGGA CUGAUGAGGCCGAAAGGCCGAA AGAUGAG | 392 |
| 106 | CUGAGGG CUGAUGAGGCCGAAAGGCCGAA AAGAUGA | 393 |
| 129 | AGGCCCA CUGAUGAGGCCGAAAGGCCGAA AAGCCUG | 394 |
| 138 | CUCCACA CUGAUGAGGCCGAAAGGCCGAA AAGGCCC | 395 |
| 148 | GUUCGAU CUGAUGAGGCCGAAAGGCCGAA AUCUCCA | 396 |
| 151 | GCUGUUC CUGAUGAGGCCGAAAGGCCGAA AUGAUCU | 397 |
| 180 | AUAGCGG CUGAUGAGGCCGAAAGGCCGAA AUCGCAU | 398 |
| 181 | UAUAGCG CUGAUGAGGCCGAAAGGCCGAA AAUCGCA | 399 |
| 186 | GCAUUUA CUGAUGAGGCCGAAAGGCCGAA AGCGGAA | 400 |
| 204 | GCCCGCU CUGAUGAGGCCGAAAGGCCGAA AGCGCCC | 401 |
| 217 | CGCCAGG CUGAUGAGGCCGAAAGGCCGAA AUACUGC | 402 |
| 239 | UUGGUGG CUGAUGAGGCCGAAAGGCCGAA AUCUGUG | 403 |
| 262 | UGAUCUU CUGAUGAGGCCGAAAGGCCGAA AUGGUGG | 404 |
| 268 | AGCCAUU CUGAUGAGGCCGAAAGGCCGAA AUCUUGA | 405 |
| 276 | UCCUGUG CUGAUGAGGCCGAAAGGCCGAA AGCCAUU | 406 |
| 301 | CCAGGGA CUGAUGAGGCCGAAAGGCCGAA AUUCGAA | 407 |
| 303 | GACCAGG CUGAUGAGGCCGAAAGGCCGAA AGAUUCG | 408 |
| 310 | CCUUGGU CUGAUGAGGCCGAAAGGCCGAA ACCAGGG | 409 |
| 323 | UCAGGAG CUGAUGAGGCCGAAAGGCCGAA AGGGGCC | 410 |
| 326 | GGCCGGU CUGAUGAGGCCGAAAGGCCGAA AGGUGGA | 411 |
| 335 | UGUGGAU CUGAUGAGGCCGAAAGGCCGAA AGGCCGG | 412 |
| 349 | UCCCCAC CUGAUGAGGCCGAAAGGCCGAA AGUUCAU | 413 |
| 352 | GCUGUUC CUGAUGAGGCCGAAAGGCCGAA AUGAUCU | 414 |
| 375 | CUCAUAG CUGAUGAGGCCGAAAGGCCGAA AGCCAUC | 415 |
| 376 | CUCCGGA CUGAUGAGGCCGAAAGGCCGAA AGACCAU | 416 |
| 378 | AGCCUCA CUGAUGAGGCCGAAAGGCCGAA AGUAGCC | 417 |
| 391 | CUGGGCA CUGAUGAGGCCGAAAGGCCGAA AGGUCAG | 418 |
| 409 | AGCUAUG CUGAUGAGGCCGAAAGGCCGAA AUACUGC | 419 |
| 416 | CUAUGGA CUGAUGAGGCCGAAAGGCCGAA ACUGCGG | 420 |
| 417 | GUUCUGG CUGAUGAGGCCGAAAGGCCGAA AGCUAUG | 421 |
| 418 | GGUUCUG CUGAUGAGGCCGAAAGGCCGAA AAGCUAU | 422 |
| 433 | CACACUG CUGAUGAGGCCGAAAGGCCGAA AUCCCCA | 423 |
| 467 | CGAACAG CUGAUGAGGCCGAAAGGCCGAA AGCCUGG | 424 |
| 469 | GCUGGCU CUGAUGAGGCCGAAAGGCCGAA AUGGCUU | 425 |
| 473 | CUGAUCU CUGAUGAGGCCGAAAGGCCGAA ACUCAAA | 426 |
| 481 | UGGUCUG CUGAUGAGGCCGAAAGGCCGAA AUUCGCU | 427 |
| 501 | AACGUGA CUGAUGAGGCCGAAAGGCCGAA AGGGGUU | 428 |
| 502 | GAACGUG CUGAUGAGGCCGAAAGGCCGAA AAGGGGU | 429 |
| 508 | CUAUAGG CUGAUGAGGCCGAAAGGCCGAA ACGUGAA | 430 |
| 509 | UCUAUAG CUGAUGAGGCCGAAAGGCCGAA AACGUGA | 431 |
| 512 | UCCUCUA CUGAUGAGGCCGAAAGGCCGAA AGGAACG | 432 |
| 514 | GCUCCUC CUGAUGAGGCCGAAAGGCCGAA AUAGGAA | 433 |
| 534 | CAAGUCA CUGAUGAGGCCGAAAGGCCGAA AGUCCCC | 434 |
| 556 | GGAAGCA CUGAUGAGGCCGAAAGGCCGAA AGGCGCA | 435 |
| 561 | CACCUGG CUGAUGAGGCCGAAAGGCCGAA AGCAGAG | 436 |
| 562 | UCACCUG CUGAUGAGGCCGAAAGGCCGAA AAGCAGA | 437 |
| 585 | GCUGGCU CUGAUGAGGCCGAAAGGCCGAA AUGGCUU | 438 |
| 598 | UCAGGAG CUGAUGAGGCCGAAAGGCCGAA AGGGGCC | 439 |
| 613 | GUGAGAG CUGAUGAGGCCGAAAGGCCGAA ACAGGGG | 440 |
| 616 | GAUGUGA CUGAUGAGGCCGAAAGGCCGAA AGGACAG | 441 |
| 617 | GGCUGAG CUGAUGAGGCCGAAAGGCCGAA AAGGGAC | 442 |
| 620 | CAUGGCU CUGAUGAGGCCGAAAGGCCGAA AGGAAGG | 443 |
| 623 | GAGAUGG CUGAUGAGGCCGAAAGGCCGAA AGCAGGA | 444 |
| 628 | UAUCAAA CUGAUGAGGCCGAAAGGCCGAA AUCGGAU | 445 |
| 630 | GUUAUCA CUGAUGAGGCCGAAAGGCCGAA AAAUCGG | 446 |
| 631 | GGUUAUC CUGAUGAGGCCGAAAGGCCGAA AAAAUCG | 447 |
| 638 | GGAACAC CUGAUGAGGCCGAAAGGCCGAA AUGGCCA | 448 |
| 661 | AGAUCUU CUGAUGAGGCCGAAAGGCCGAA AGCUCGG | 449 |
| 667 | CUCGGCA CUGAUGAGGCCGAAAGGCCGAA AUCUUGA | 450 |
| 687 | GCUCCCA CUGAUGAGGCCGAAAGGCCGAA AGUUCCG | 451 |
| 700 | CCCCACC CUGAUGAGGCCGAAAGGCCGAA AGGCAGC | 452 |
| 715 | GCAAGAA CUGAUGAGGCCGAAAGGCCGAA AUCUCAU | 453 |
| 717 | CAGCAAG CUGAUGAGGCCGAAAGGCCGAA AGAUCUC | 454 |
| 718 | ACAGCAA CUGAUGAGGCCGAAAGGCCGAA AAGAUCU | 455 |
| 721 | CGCAAUG CUGAUGAGGCCGAAAGGCCGAA AGGAGAA | 456 |
| 751 | ACACCUC CUGAUGAGGCCGAAAGGCCGAA AUGUCUU | 457 |
| 759 | CGUGAAA CUGAUGAGGCCGAAAGGCCGAA ACACCUC | 458 |
| 761 | CCCGUGA CUGAUGAGGCCGAAAGGCCGAA AUACACC | 459 |

TABLE IV-continued

Mouse rel A HH Ribozyme Sequences

| nt. Sequence | HH Ribozyme Sequence | Seq. ID No. |
| --- | --- | --- |
| 762 | UCCCGUG CUGAUGAGGCCGAAAGGCCGAA AAUACAC | 460 |
| 763 | GUCCCGU CUGAUGAGGCCGAAAGGCCGAA AAAUACA | 461 |
| 792 | AGAAAAG CUGAUGAGGCCGAAAGGCCGAA AGCCUCG | 462 |
| 795 | UUGAGAA CUGAUGAGGCCGAAAGGCCGAA AGGAGCC | 463 |
| 796 | CUUGAGA CUGAUGAGGCCGAAAGGCCGAA AAGGAGC | 464 |
| 797 | GCUUGAG CUGAUGAGGCCGAAAGGCCGAA AAAGGAG | 465 |
| 798 | AGCUUGA CUGAUGAGGCCGAAAGGCCGAA AAAAGGA | 466 |
| 829 | GGAACAC CUGAUGAGGCCGAAAGGCCGAA AUGGCCA | 467 |
| 834 | AGUCCGG CUGAUGAGGCCGAAAGGCCGAA ACACAAU | 468 |
| 835 | GAGUCCG CUGAUGAGGCCGAAAGGCCGAA AACACAA | 469 |
| 845 | GCGUACG CUGAUGAGGCCGAAAGGCCGAA AGGAGUC | 470 |
| 849 | GUCGGCG CUGAUGAGGCCGAAAGGCCGAA ACGGAGG | 471 |
| 872 | CGAACAG CUGAUGAGGCCGAAAGGCCGAA AGCCUGG | 472 |
| 883 | GCAUGGA CUGAUGAGGCCGAAAGGCCGAA ACUCGAA | 473 |
| 885 | CUGCAUG CUGAUGAGGCCGAAAGGCCGAA AGACUCG | 474 |
| 905 | CGAUCAG CUGAUGAGGCCGAAAGGCCGAA AGGCCGC | 475 |
| 906 | GCGAUCA CUGAUGAGGCCGAAAGGCCGAA AAGGCCG | 476 |
| 919 | GCUCACU CUGAUGAGGCCGAAAGGCCGAA AGCUCGC | 477 |
| 936 | GUACUGG CUGAUGAGGCCGAAAGGCCGAA ACUCCAU | 478 |
| 937 | AGUACUG CUGAUGAGGCCGAAAGGCCGAA AACUCCA | 479 |
| 942 | UGGCAAG CUGAUGAGGCCGAAAGGCCGAA ACUGGAA | 480 |
| 953 | UCAUGUG CUGAUGAGGCCGAAAGGCCGAA AUGAGGC | 481 |
| 962 | CGGUGGC CUGAUGAGGCCGAAAGGCCGAA AUCAUCU | 482 |
| 965 | GUCUGGC CUGAUGAGGCCGAAAGGCCGAA AGUACUG | 483 |
| 973 | UCUCUUC CUGAUGAGGCCGAAAGGCCGAA AUCCGGU | 484 |
| 986 | ACUCUUG CUGAUGAGGCCGAAAGGCCGAA AGGUCUC | 485 |
| 996 | GGUCUCA CUGAUGAGGCCGAAAGGCCGAA AGGUCCU | 486 |
| 1005 | ACUCUUG CUGAUGAGGCCGAAAGGCCGAA AGGUCUC | 487 |
| 1006 | UACUCUU CUGAUGAGGCCGAAAGGCCGAA AAGGUCU | 488 |
| 1015 | UCUUCAU CUGAUGAGGCCGAAAGGCCGAA AUACUCU | 489 |
| 1028 | UUGAAAG CUGAUGAGGCCGAAAGGCCGAA ACUCUUC | 490 |
| 1031 | CCAUUGA CUGAUGAGGCCGAAAGGCCGAA AGGACUC | 491 |
| 1032 | UCCAUUG CUGAUGAGGCCGAAAGGCCGAA AAGGACU | 492 |
| 1033 | GUCCAUU CUGAUGAGGCCGAAAGGCCGAA AAAGGAC | 493 |
| 1058 | CGGGUUG CUGAUGAGGCCGAAAGGCCGAA AGGCCGG | 494 |
| 1064 | UUGGAUC CUGAUGAGGCCGAAAGGCCGAA AGGUGUA | 495 |
| 1072 | GCACAGC CUGAUGAGGCCGAAAGGCCGAA AUACGCC | 496 |
| 1082 | UUUCGGG CUGAUGAGGCCGAAAGGCCGAA AGGCACA | 497 |
| 1083 | ACUUCGG CUGAUGAGGCCGAAAGGCCGAA AAGGCUU | 498 |
| 1092 | AGAAGUU CUGAUGAGGCCGAAAGGCCGAA AGUUUCG | 499 |
| 1097 | GGGACAG CUGAUGAGGCCGAAAGGCCGAA AGUUGAG | 500 |
| 1098 | GGGGACA CUGAUGAGGCCGAAAGGCCGAA AAGUUGA | 501 |
| 1102 | GCUUGGG CUGAUGAGGCCGAAAGGCCGAA ACAGAAG | 502 |
| 1125 | GAAGGUG CUGAUGAGGCCGAAAGGCCGAA AGGGCUG | 503 |
| 1127 | GUAAGGC CUGAUGAGGCCCOAAAGGCCGAA AUAUGGC | 504 |
| 1131 | UGGUGCU CUGAUGAGGCCGAAAGGCCGAA AGGGAUG | 505 |
| 1132 | AUGCUGG CUGAUGAGGCCGAAAGGCCGAA AAGGUGU | 506 |
| 1133 | GAAGCUG CUGAUGAGGCCGAAAGGCCGAA AGAUGGA | 507 |
| 1137 | GCGCGCU CUGAUGAGGCCGAAAGGCCGAA AAGUAAA | 508 |
| 1140 | GCUGAGG CUGAUGAGGCCGAAAGGCCGAA AUGCUGG | 509 |
| 1153 | CAAAGUU CUGAUGAGGCCGAAAGGCCGAA AUGGUGC | 510 |
| 1158 | CUCAUCA CUGAUGAGGCCGAAAGGCCGAA AGUUGAU | 511 |
| 1167 | GGGGGAA CUGAUGAGGCCGAAAGGCCGAA ACUCAUC | 512 |
| 1168 | UGGGGGA CUGAUGAGGCCGAAAGGCCGAA AACUCAU | 513 |
| 1169 | AUGGGGG CUGAUGAGGCCGAAAGGCCGAA AAACUCA | 514 |
| 1182 | UGAUGGU CUGAUGAGGCCGAAAGGCCGAA ACAGCAU | 515 |
| 1183 | CUGAUGG CUGAUGAGGCCGAAAGGCCGAA AACAGCA | 516 |
| 1184 | UCAGGAG CUGAUGAGGCCGAAAGGCCGAA AGGGGCC | 517 |
| 1187 | GGCUGAG CUGAUGAGGCCGAAAGGCCGAA AAGGGAC | 518 |
| 1188 | CUGCCCU CUGAUGAGGCCGAAAGGCCGAA AUGGUAA | 519 |
| 1198 | UCAGACU CUGAUGAGGCCGAAAGGCCGAA AACUCCC | 520 |
| 1209 | GAAGGUG CUGAUGAGGCCGAAAGGCCGAA AGGGCUG | 521 |
| 1215 | CGGUGCU CUGAUGAGGCCGAAAGGCCGAA AGGCCAG | 522 |
| 1229 | GCUGAGG CUGAUGAGGCCGAAAGGCCGAA AGGGACC | 523 |
| 1237 | GGGGCAG CUGAUGAGGCCGAAAGGCCGAA AGCUGGG | 524 |
| 1250 | GAGCCUG CUGAUGAGGCCGAAAGGCCGAA AGGCUGG | 525 |
| 1268 | GGGGCAG CUGAUGAGGCCGAAAGGCCGAA AGCUGGG | 526 |
| 1279 | AGGAAGG CUGAUGAGGCCGAAAGGCCGAA ACCAUGG | 527 |
| 1281 | CGCAGCU CUGAUGAGGCCGAAAGGCCGAA AGCCCAC | 528 |
| 1286 | UGGGGGA CUGAUGAGGCCGAAAGGCCGAA AACUCAU | 529 |
| 1309 | AGACUCG CUGAUGAGGCCGAAAGGCCGAA ACAGGAG | 530 |
| 1315 | GGGUUAG CUGAUGAGGCCGAAAGGCCGAA ACUGGGG | 531 |
| 1318 | CCGGGGU CUGAUGAGGCCGAAAGGCCGAA AGAACUG | 532 |
| 1331 | GACUGGG CUGAUGAGGCCGAAAGGCCGAA AGGACCC | 533 |
| 1334 | UCAGCUU CUGAUGAGGCCGAAAGGCCGAA AGAAAAG | 534 |

TABLE IV-continued

Mouse rel A HH Ribozyme Sequences

| nt. Sequence | HH Ribozyme Sequence | Seq. ID No. |
|---|---|---|
| 1389 | GGCUUCC CUGAUGAGGCCGAAAGGCCGAA ACAGCGU | 535 |
| 1413 | AGCAUCA CUGAUGAGGCCGAAAGGCCGAA ACUGCAG | 536 |
| 1414 | CAGCAUC CUGAUGAGGCCGAAAGGCCGAA AACUGCA | 537 |
| 1437 | GCCAAGC CUGAUGAGGCCGAAAGGCCGAA AGGCCCC | 538 |
| 1441 | UGUUGCC CUGAUGAGGCCGAAAGGCCGAA AGCAAGG | 539 |
| 1467 | GUCUGUG CUGAUGAGGCCGAAAGGCCGAA ACACUCC | 540 |
| 1468 | GGUCUGU CUGAUGAGGCCGAAAGGCCGAA AACACUC | 541 |
| 1482 | GUCCACA CUGAUGAGGCCGAAAGGCCGAA AUGCCAG | 542 |
| 1486 | AGUUCCC CUGAUGAGGCCGAAAGGCCGAA ACCGAAG | 543 |
| 1494 | AAACUCU CUGAUGAGGCCGAAAGGCCGAA AGUUGUC | 544 |
| 1500 | CUGCUGA CUGAUGAGGCCGAAAGGCCGAA ACUCUGA | 545 |
| 1501 | GCUGCUG CUGAUGAGGCCGAAAGGCCGAA AACUCUG | 546 |
| 1502 | AGCUGCU CUGAUGAGGCCGAAAGGCCGAA AAACUCU | 547 |
| 1525 | ACACAGG CUGAUGAGGCCGAAAGGCCGAA AUGCACC | 548 |
| 1566 | UUCAGGG CUGAUGAGGCCGAAAGGCCGAA ACUCCAU | 549 |
| 1577 | CGAGUUA CUGAUGAGGCCGAAAGGCCGAA AGCUUCA | 550 |
| 1579 | GGCGAGU CUGAUGAGGCCGAAAGGCCGAA AUAGCUU | 551 |
| 1583 | ACCAGGC CUGAUGAGGCCGAAAGGCCGAA AGUUAUA | 552 |
| 1588 | CCCUCUC CUGAUGAGGCCGAAAGGCCGAA AGGAGAG | 553 |
| 1622 | GGGGCAG CUGAUGAGGCCGAAAGGCCGAA AGCUGGG | 554 |
| 1628 | CCUACCG CUGAUGAGGCCGAAAGGCCGAA AGCAGGA | 555 |
| 1648 | CAUUGGG CUGAUGAGGCCGAAAGGCCGAA AGCCCCG | 556 |
| 1660 | CUGGGCA CUGAUGAGGCCGAAAGGCCGAA AGGUCAG | 557 |
| 1663 | CACCUGG CUGAUGAGGCCGAAAGGCCGAA AGCAGAG | 558 |
| 1664 | UCACCUG CUGAUGAGGCCGAAAGGCCGAA AAGCAGA | 559 |
| 1665 | ACCUCCG CUGAUGAGGCCGAAAGGCCGAA AAGCGAG | 560 |
| 1680 | GGAGGAG CUGAUGAGGCCGAAAGGCCGAA AGUCUUC | 561 |
| 1681 | UGGAGGA CUGAUGAGGCCGAAAGGCCGAA AAGUCUU | 562 |
| 1683 | AAUGGAG CUGAUGAGGCCGAAAGGCCGAA AGAAGUC | 563 |
| 1686 | CGCAAUG CUGAUGAGGCCGAAAGGCCGAA AGGAGAA | 564 |
| 1690 | UGUCCGC CUGAUGAGGCGGAAAGGCCGAA AUGGAGG | 565 |
| 1704 | AGCAGAG CUGAUGAGGCCGAAAGGCCGAA AGUCCAU | 566 |
| 1705 | GAGCAGA CUGAUGAGGCCGAAAGGCCGAA AAGUCCA | 567 |
| 1707 | AAGAGCA CUGAUGAGGCCGAAAGGCCGAA AGAAGUC | 568 |
| 1721 | CUGAUCU CUGAUGAGGCCGAAAGGCCGAA ACUCAAA | 569 |
| 1726 | AGGAGCU CUGAUGAGGCCGAAAGGCCGAA AUCUGAC | 570 |
| 1731 | ACCUUAG CUGAUGAGGCCGAAAGGCCGAA AGCUGAU | 571 |
| 1734 | AGGACCU CUGAUGAGGCCGAAAGGCCGAA AGGAGCU | 572 |
| 1754 | CUCUUGG CUGAUGAGGCCGAAAGGCCGAA AGCACUG | 573 |

TABLE V

Human rel A HH Ribozyme Sequences

| nt. Sequence | HH Ribozyme Sequence | SEQ ID NO. |
|---|---|---|
| 19 | UACAGAC CUGAUGAGGCCGAAAGGCCGAA AGCCAUU | 574 |
| 22 | CACUACA CUGAUGAGGCCGAAAGGCCGAA ACGAGCC | 575 |
| 26 | CGUGCAC CUGAUGAGGCCGAAAGGCCGAA ACACACG | 576 |
| 93 | GAGGGGG CUGAUGAGGCCGAAAGGCCGAA ACAGUUC | 577 |
| 94 | UGAGGGG CUGAUGAGGCCGAAAGGCCGAA AACAGUU | 578 |
| 100 | GGAAGAU CUGAUGAGGCCGAAAGGCCGAA AGGGGGA | 579 |
| 103 | CCGGGAA CUGAUGAGGCCGAAAGGCCGAA AUGAGGG | 580 |
| 105 | UGCCGGG CUGAUGAGGCCGAAAGGCCGAA AGAUGAG | 581 |
| 106 | CUGCCGG CUGAUGAGGCCGAAAGGCCGAA AAGAUGA | 582 |
| 129 | GGGGCCA CUGAUGAGGCCGAAAGGCCGAA AGGCCUG | 583 |
| 138 | CUCCACA CUGAUGAGGCCGAAAGGCCGAA AGGGGCC | 584 |
| 148 | GCUCAAU CUGAUGAGGCCGAAAGGCCGAA AUCUCCA | 585 |
| 151 | GCUGCUC CUGAUGAGGCCGAAAGGCCGAA AUGAUCU | 586 |
| 180 | GUAGCGG CUGAUGAGGCCGAAAGGCCGAA AGCGCAU | 587 |
| 181 | UGUAGCG CUGAUGAGGCCGAAAGGCCGAA AAGCGCA | 588 |
| 186 | GCACUUG CUGAUGAGGCCGAAAGGCCGAA AGCGGAA | 589 |
| 204 | GCCCGCG CUGAUGAGGCCGAAAGGCCGAA AGCGCCC | 590 |
| 217 | CGCCUGG CUGAUGAGGCCGAAAGGCCGAA AUGCUGC | 591 |
| 239 | UUGGUGG CUGAUGAGGCCGAAAGGCCGAA AUCUGUG | 592 |
| 262 | UGAUCUU CUGAUGAGGCCGAAAGGCCGAA AUGGUGG | 593 |
| 268 | AGCCAUU CUGAUGAGGCCGAAAGGCCGAA AUCUUGA | 594 |
| 276 | UCCUGUG CUGAUGAGGCCGAAAGGCCGAA AGCCAUU | 595 |
| 301 | CCAGGGA CUGAUGAGGCCGAAAGGCCGAA AUGCGCA | 596 |
| 303 | GACCAGG CUGAUGAGGCCGAAAGGCCGAA AGAUGCG | 597 |
| 310 | CCUUGGU CUGAUGAGGCCGAAAGGCCGAA ACCAGGG | 598 |
| 323 | CGGUGAG CUGAUGAGGCCGAAAGGCCGAA AGGGUCC | 599 |

TABLE V-continued

Human rel A HH Ribozyme Sequences

| nt. Sequence | HH Ribozyme Sequence | SEQ ID NO. |
|---|---|---|
| 326 | GGCCGGU CUGAUGAGGCCGAAAGGCCGAA AGGAGGG | 600 |
| 335 | UGGGGGU CUGAUGAGGCCGAAAGGCCGAA AGGCCGG | 601 |
| 349 | UUCCUAC CUGAUGAGGCCGAAAGGCCGAA AGCUCGU | 602 |
| 352 | CCUUUCC CUGAUGAGGCCGAAAGGCCGAA ACAAGCU | 603 |
| 375 | CUCAUAG CUGAUGAGGCCGAAAGGCCGAA AGCCAUC | 604 |
| 376 | CCUCAUA CUGAUGAGGCCGAAAGGCCGAA AAGCCAU | 605 |
| 378 | AGCCUCA CUGAUGAGGCCGAAAGGCCGAA AGAAGCC | 606 |
| 391 | CCGGGCA CUGAUGAGGCCGAAAGGCCGAA AGCUCAG | 607 |
| 409 | AACUGUG CUGAUGAGGCCGAAAGGCCGAA AUGCAGC | 608 |
| 416 | UUCUGGA CUGAUGAGGCCGAAAGGCCGAA ACUGUGG | 609 |
| 417 | GUUCUGG CUGAUGAGGCCGAAAGGCCGAA AACUGUG | 610 |
| 418 | GGUUCUG CUGAUGAGGCCGAAAGGCCGAA AAACUGU | 611 |
| 433 | CACACUG CUGAUGAGGCCGAAAGGCCGAA AUUCCCA | 612 |
| 467 | UGACUGA CUGAUGAGGCCGAAAGGCCGAA AGCCUGC | 613 |
| 469 | GCUGACU CUGAUGAGGCCGAAAGGCCGAA AUAGCCU | 614 |
| 473 | AUGCGCU CUGAUGAGGCCGAAAGGCCGAA ACUGAUA | 615 |
| 461 | UGGUCUG CUGAUGAGGCCGAAAGGCCGAA AUGCGCU | 616 |
| 501 | AACUUGG CUGAUGAGGCCGAAAGGCCGAA AGGGGUU | 617 |
| 502 | GAACUUG CUGAUGAGGCCGAAAGGCCGAA AAGGGGU | 618 |
| 508 | CUAUAGG CUGAUGAGGCCGAAAGGCCGAA ACUUGAA | 619 |
| 509 | UCUAUAG CUGAUGAGGCCGAAAGGCCGAA AACUUGG | 620 |
| 512 | UCUUCUA CUGAUGAGGCCGAAAGGCCGAA AGGAACU | 621 |
| 514 | GCUCUUC CUGAUGAGGCCGAAAGGCCGAA AUAGGAA | 622 |
| 534 | CAGGUCG CUGAUGAGGCCGAAAGGCCGAA AGUCCCC | 623 |
| 556 | GGAAGCA CUGAUGAGGCCGAAAGGCCGAA AGCCGCA | 624 |
| 561 | CACCUGG CUGAUGAGGCCGAAAGGCCGAA AGCAGAG | 625 |
| 562 | UCACCUG CUGAUGAGGGGGAAAGGCCGAA AAGCAGA | 626 |
| 585 | CCUGCCU CUGAUGAGGCCGAAAGGCCGAA AUGGGUC | 627 |
| 598 | GCAGGGG CUGAUGAGGCCGAAAGGCCGAA AGGGGCC | 628 |
| 613 | GAGGAAG CUGAUGAGGCCGAAAGGCCGAA ACAGGCG | 629 |
| 616 | GAUGAGG CUGAUGAGGCCGAAAGGCCGAA AGGACAG | 630 |
| 617 | GGAUGAG CUGAUGAGGCGGAAAGGCCGAA AAGGACA | 631 |
| 620 | AUGGGAU CUGAUGAGGCCGAAAGGGGGAA AGGAAGG | 632 |
| 623 | AAGAUGG CUGAUGAGGCCGAAAGGGCGAA AUGAGGA | 633 |
| 628 | UGUCAAA CUGAUGAGGCCGAAAGGCCGAA AUCGGAU | 634 |
| 630 | AUUGUCA CUGAUGAGGCCGAAAGGCCGAA AGAUGGG | 635 |
| 631 | GAUUGUC CUGAUGAGGCCGAAAGGCCGAA AAGAUGG | 636 |
| 638 | GGGGCAC CUGAUGAGGGCGAAAGGCCGAA AUUGUCA | 637 |
| 661 | AGAUCUU CUGAUGAGGCCGAAAGGGCGAA AGCUCGG | 638 |
| 667 | CUCGGCA CUGAUGAGGCCGAAAGGCCGAA AUCUUGA | 639 |
| 687 | GCUGCCA CUGAUGAGGCCGAAAGGCCGAA AGUUUGG | 640 |
| 700 | CCGCAGC CUGAUGAGGCCGAAAGGCCGAA AGGCAGG | 641 |
| 715 | GUAGGAA CUGAUGAGGGGGAAAGGCCGAA AUCUCAU | 642 |
| 717 | CAGUAAG CUGAUGAGGCCGAAAGGCCGAA AGAUCUC | 643 |
| 718 | ACAGUAG CUGAUGAGGCGGAAAGGCCGAA AAGAUCU | 644 |
| 721 | CACACAG CUGAUGAGGCCGAAAGGCCGAA AGGAAGA | 645 |
| 751 | ACACCUC CUGAUGAGGGGGAAAGGCCGAA AUGUCCU | 646 |
| 759 | CGUGAAA CUGAUGAGGCCGAAAGGCCGAA ACAGCUC | 647 |
| 761 | CCCGUGA CUGAUGAGGCCGAAAGGCCGAA AUACACC | 648 |
| 762 | UCCCGUG CUGAUGAGGCCGAAAGGCCGAA AAUACAC | 649 |
| 763 | GUGGCGU CUGAUGAGGGGGAAAGGCCGAA AAAUACA | 650 |
| 792 | CGAAAAG CUGAUGAGGGGGAAAGGCCGAA AGCCUCG | 651 |
| 795 | UUGCGAA CUGAUGAGGCCGAAAGGCGGAA AGGAGCC | 652 |
| 796 | CUUGCGA CUGAUGAGGCCGAAAGGCCGAA AAGGAGG | 653 |
| 797 | GCUUGCG CUGAUGAGGCCGAAAGGCCGAA AAAGGAG | 654 |
| 798 | AGCUUGC CUGAUGAGGCCGAAAGGCCGAA AAAAGGA | 655 |
| 829 | GGAACAC CUGAUGAGGCCGAAAGGCCGAA AUGGCCA | 656 |
| 834 | GGUCCGG CUGAUGAGGCCGAAAGGCCGAA ACACAAU | 657 |
| 835 | GGGUCCG CUGAUGAGGCCGAAAGGCCGAA AACACAA | 658 |
| 845 | GCGUAGG CUGAUGAGGCCGAAAGGCCGAA AGGGGUC | 659 |
| 849 | GUCUGCG CUGAUGAGGCCGAAAGGCCGAA AGGGAGG | 660 |
| 872 | CGCACAG CUGAUGAGGGCGAAAGGGCGAA AGCCUGC | 661 |
| 883 | GCAUGGA CUGAUGAGGGCGAAAGGGGGAA ACACGCA | 662 |
| 885 | CUGCAUG CUGAUGAGGCCGAAAGGCCGAA AGACACG | 662 |
| 905 | CGGUCGG CUGAUGAGGCCGAAAGGCCGAA AGGCCGC | 664 |
| 906 | CGGGUCG CUGAUGAGGCGGAAAGGCCGAA AAGGGGG | 665 |
| 919 | GCUCACU CUGAUGAGGCCGAAAGGCCGAA AGCUCCC | 666 |
| 936 | GUACUGG CUGAUGAGGCCGAAAGGCGGAA AUUCCAU | 667 |
| 937 | GGUACUG CUGAUGAGGCCGAAAGGGGGAA AAUUCCA | 668 |
| 942 | UGGCAGG CUGAUGAGGCCGAAAGGCCGAA ACUGGAA | 669 |
| 953 | UCGUCUG CUGAUGAGGCCGAAAGGCCGAA AUCUGGC | 670 |
| 962 | CGGUGAC CUGAUGAGGCCGAAAGGCCGAA AUGGUGU | 671 |
| 965 | AUCCGGU CUGAUGAGGCCGAAAGGCCGAA ACGAUCG | 672 |
| 973 | UCUCCUC CUGAUGAGGCCGAAAGGCCGAA AUCCGGU | 673 |
| 986 | GUCCUUU CUGAUGAGGCCGAAAGGGCGAA AGGUUUC | 674 |

TABLE V-continued

Human rel A HH Ribozyme Sequences

| nt. Sequence | HH Ribozyme Sequence | SEQ ID NO. |
|---|---|---|
| 996 | GGUCUCA CUGAUGAGGCCGAAAGGCCGAA AUGUCCU | 675 |
| 1005 | GCUCUUG CUGAUGAGGCCGAAAGGCCGAA AGGUCUC | 676 |
| 1006 | UGCUCUU CUGAUGAGGCCGAAAGGCCGAA AAGGUCU | 677 |
| 1015 | UCUUCAU CUGAUGAGGCCGAAAGGCCGAA AUGCUCU | 678 |
| 1028 | CUGAAAG CUGAUGAGGCCGAAAGGCCGAA ACUCUUC | 679 |
| 1031 | CCGCUGA CUGAUGAGGCCGAAAGGCCGAA AGGACUC | 680 |
| 1032 | UCCGCUG CUGAUGAGGCCGAAAGGCCGAA AAGGACU | 681 |
| 1033 | GUCCGCU CUGAUGAGGCCGAAAGGCCGAA AAAGGAC | 682 |
| 1058 | CGAGGUG CUGAUGAGGCCGAAAGGCCGAA AGGCCGG | 683 |
| 1064 | AUGCGUC CUGAUGAGGCCGAAAGGCCGAA AGGUGGA | 684 |
| 1072 | GCACAGC CUGAUGAGGCCGAAAGGCCGAA AUGCGUC | 685 |
| 1082 | CUGCGGG CUGAUGAGGCCGAAAGGCCGAA AGGCACA | 686 |
| 1083 | GCUGCGG CUGAUGAGGCCGAAAGGCCGAA AAGGCAC | 687 |
| 1092 | AGAAGCU CUGAUGAGGCCGAAAGGCCGAA AGCUGCG | 688 |
| 1097 | GGGACAG CUGAUGAGGCCGAAAGGCCGAA AGCUGAG | 689 |
| 1098 | GGGGACA CUGAUGAGGCCGAAAGGCCGAA AAGCUGA | 690 |
| 1102 | GCUUGGG CUGAUGAGGCCGAAAGGCCGAA ACAGAAG | 691 |
| 1125 | AAAGGGA CUGAUGAGGCCGAAAGGCCGAA AGGGCUG | 692 |
| 1127 | GUAAAGG CUGAUGAGGCCGAAAGGCCGAA AUAGGGC | 693 |
| 1131 | UGACGUA CUGAUGAGGCCGAAAGGCCGAA AGGGAUA | 694 |
| 1132 | AUGACGU CUGAUGAGGCCGAAAGGCCGAA AAGGGAU | 695 |
| 1133 | GAUGACG CUGAUGAGGCCGAAAGGCCGAA AAAGGGA | 696 |
| 1137 | CAGGGAU CUGAUGAGGCCGAAAGGCCGAA ACGUAAA | 697 |
| 1140 | GCUCAGG CUGAUGAGGCCGAAAGGCCGAA AUGACGU | 698 |
| 1153 | CAUAGUU CUGAUGAGGCCGAAAGGCCGAA AUGGUGC | 699 |
| 1158 | CUCAUCA CUGAUGAGGCCGAAAGGCCGAA AGUUGAU | 700 |
| 1167 | GGUGGGA CUGAUGAGGCCGAAAGGCCGAA ACUCAUC | 701 |
| 1168 | UGGUGGG CUGAUGAGGCCGAAAGGCCGAA AACUCAU | 702 |
| 1169 | AUGGUGG CUGAUGAGGCCGAAAGGCCGAA AAACUCA | 703 |
| 1182 | AGAAGGA CUGAUGAGGCCGAAAGGCCGAA ACACCAU | 704 |
| 1183 | CAGAAGG CUGAUGAGGCCGAAAGGCCGAA AACACCA | 705 |
| 1184 | CCAGAAG CUGAUGAGGCCGAAAGGCCGAA AAACACC | 706 |
| 1187 | UGCCCAG CUGAUGAGGCCGAAAGGCCGAA AAGAAAC | 707 |
| 1188 | CUGCCCA CUGAUGAGGCCGAAAGGCCGAA AAGGAAA | 708 |
| 1198 | CCUGGCU CUGAUGAGGCCGAAAGGCCGAA AUCUGCC | 709 |
| 1209 | GAAGGCC CUGAUGAGGCCGAAAGGCCGAA AGGCCUG | 710 |
| 1215 | CGGGGCC CUGAUGAGGCCGAAAGGCCGAA AGGCCGA | 711 |
| 1229 | ACUUGGG CUGAUGAGGCCGAAAGGCCGAA AGGGGCC | 712 |
| 1237 | GGGGCAG CUGAUGAGGCCGAAAGGCCGAA ACUUGGG | 713 |
| 1250 | GGGGCUG CUGAUGAGGCCGAAAGGCCGAA AGCCUGG | 714 |
| 1268 | AUGGCUG CUGAUGAGGCCGAAAGGCCGAA AGCAGGG | 715 |
| 1279 | GAGCUGA CUGAUGAGGCCGAAAGGCCGAA ACCAUGG | 716 |
| 1281 | CAGAGCU CUGAUGAGGCCGAAAGGCCGAA AUACCAU | 717 |
| 1286 | UGGGCCA CUGAUGAGGCCGAAAGGCCGAA AGCUGAU | 718 |
| 1309 | GGACUGG CUGAUGAGGCCGAAAGGCCGAA ACAGGGG | 719 |
| 1315 | GGGCUAG CUGAUGAGGCCGAAAGGCCGAA ACUGGGA | 720 |
| 1318 | CUGGGGC CUGAUGAGGCCGAAAGGCCGAA AGGACUG | 721 |
| 1331 | GCCUGAG CUGAUGAGGCCGAAAGGCCGAA AGGGCCU | 722 |
| 1334 | ACAGCCU CUGAGAGGCCGAAAGGCCGAA AGGAGGG | 723 |
| 1389 | GGCUCUU CUGAUGAGGCCGAAAGGCCGAA ACAGCGU | 724 |
| 1413 | AUCAUCA CUGAGAGGCCGAAAGGCCGAA ACUGCAG | 725 |
| 1414 | CAUCAUC CUGAUGAGGCCGAAAGGCCGAA AACUGCA | 726 |
| 1437 | GCCAAGC CUGAUGAGGCCGAAAGGCCGAA AGGCCCC | 727 |
| 1441 | UGUUGCC CUGAUGAGGCCGAAAGGCCGAA AGCAAGG | 728 |
| 1467 | GUCUGUG CUGAUGAGGCCGAAAGGCCGAA ACACAGC | 729 |
| 1468 | GGUCUGU CUGAUGAGGCCGAAAGGCCGAA AACACAG | 730 |
| 1482 | GUCGACG CUGAUGAGGCCGAAAGGCCGAA AUGCCAG | 731 |
| 1486 | AGUUGUC CUGAGAGGCCGAAAGGCCGAA ACGGAUG | 732 |
| 1494 | AAACUCG CUGAUGAGGCCGAAAGGCCGAA AGUUGUC | 733 |
| 1500 | CUGCUGA CUGAUGAGGCCGAAAGGCCGAA ACUCGGA | 734 |
| 1501 | GCUGCUG CUGAUGAGGCCGAAAGGCCGAA AACUCGG | 735 |
| 1502 | AGCUGCU CUGAUGAGGCCGAAAGGCCGAA AAACUCG | 736 |
| 1525 | CCACAGG CUGAUGAGGCCGAAAGGCCGAA AUGCCCU | 737 |
| 1566 | CUCAGGG CUGAUGAGGCCGAAAGGCCGAA ACUCCAU | 738 |
| 1577 | CGAGUUA CUGAGAGGCCGAAAGGCCGAA AGCCUCA | 739 |
| 1579 | GGCGAGU CUGAUGAGGCCGAAAGGCCGAA AUAGCCU | 740 |
| 1583 | ACCAGGC CUGAUGAGGCCGAAAGGCCGAA AGUUAUA | 741 |
| 1588 | CUGUCAC CUGAUGAGGCCGAAAGGCCGAA AGGCGAG | 742 |
| 1622 | GGAGCAG CUGAUGAGGCCGAAAGGCCGAA AGCUGGG | 743 |
| 1628 | CCCAGUG CUGAUGAGGCCGAAAGGCCGAA AGCAGGA | 744 |
| 1648 | CAUUGGG CUGAUGAGGCCGAAAGGCCGAA AGCCCCG | 745 |
| 1660 | CUGAAAG CUGAUGAGGCCGAAAGGCCGAA AGGCCAU | 746 |
| 1663 | CUCCUGA CUGAUGAGGCCGAAAGGCCGAA AGGAGGC | 747 |
| 1664 | UCUCCUG CUGAUGAGGCCGAAAGGCCGAA AAGGAGG | 748 |
| 1665 | AUCUCCU CUGAUGAGGCCGAAAGGCCGAA AAAGGAG | 749 |

TABLE V-continued

Human rel A HH Ribozyme Sequences

| nt. Sequence | HH Ribozyme Sequence | SEQ ID NO. |
|---|---|---|
| 1680 | GGAGGAG CUGAUGAGGCCGAAAGGCCGAA AGUCUUC | 750 |
| 1661 | UGGAGGA CUGAUGAGGCCGAAAGGCCGAA AAGUCUU | 751 |
| 1683 | AAUGGAG CUGAUGAGGCCGAAAGGCCGAA AGAAGUC | 752 |
| 1686 | CGCAAUG CUGAUGAGGCCGAAAGGCCGAA AGGAGAA | 753 |
| 1690 | UGUCCGC CUGAUGAGGCCGAAAGGCCGAA AUGGAGG | 754 |
| 1704 | GGCUGAG CUGAUGAGGCCGAAAGGCCGAA AGUCCAU | 755 |
| 1705 | GGGCUGA CUGAUGAGGCCGAAAGGCCGAA AAGUCCA | 756 |
| 1707 | CAGGGCU CUGAUGAGGCCGAAAGGCCGAA AGAAGUC | 757 |
| 1721 | CUGAUCU CUGAUGAGGCCGAAAGGCCGAA ACUCAGC | 758 |
| 1726 | AGGAGCU CUGAUGAGGCCGAAAGGCCGAA AUCUGAC | 759 |
| 1731 | CCCUUAG CUGAUGAGGCCGAAAGGCCGAA AGCUGAU | 760 |
| 1734 | ACCCCCU CUGAUGAGGCCGAAAGGCCGAA AGGAGCU | 761 |
| 1754 | CUCUGGG CUGAUGAGGCCGAAAGGCCGAA AGGGCAG | 762 |

TABLE VI

Human rel A Hairpin Ribozyme/Target Sequences

| nt. Position | Hairpin Ribozyme sequence | Seq ID No. | Substrate | Seq ID No. |
|---|---|---|---|---|
| 90 | UGAGGGGG AGAA GUUC ACCAGAGAAACACACGUUGUGGUACAUUACCUGGUA | 763 | GAACU GUU CCCCCUCA | 778 |
| 156 | GCUGCUUG AGAA GCUC ACCAGAGAAACACACGUUGUGGUACAUUACCUGGUA | 764 | GAGCA GCC CAAGCAGC | 779 |
| 362 | GCCAUCCC AGAA GUCC ACCAGAGAAACACACGUUGUGGUACAUUACCUGGUA | 765 | GGACU GCC GGGAUGGC | 780 |
| 413 | GUUCUGGA AGAA GUGG ACCAGAGAAACACACGUUGUGGUACAUUACCUGGUA | 766 | CCACA GUU UCCAGAAC | 781 |
| 606 | GAAGGACA AGAA GCAG ACCAGAGAAACACACGUUGUGGUACAUUACCUGGUA | 767 | CUGCC GCC UGUCCUUC | 782 |
| 652 | UUGAGCUC AGAA GUGU ACCAGAGAAACACACGUUGUGGUACAUUACCUGGUA | 768 | ACACU GCC GAGCUCAA | 783 |
| 695 | CCCACCGA AGAA GCUG ACCAGAGAAACACACGUUGUGGUACAUUACCUGGUA | 769 | CAGCU GCC UCGGUGGG | 784 |
| 853 | AGGCUGGG AGAA GCGU ACCAGAGAAACACACGUUGUGGUACAUUACCUGGUA | 770 | ACGCA GAC CCCAGCCU | 785 |
| 900 | GGUCGGAA AGAA GCAG ACCAGAGAAACACACGUUGUGGUACAUUACCUGGUA | 771 | CGGCG GCC UUCCGACC | 786 |
| 955 | UGACGAUC AGAA GUAU ACCAGAGAAACACACGUUGUGGUACAUUACCUGGUA | 772 | AUACA GAC GAUCGUCA | 787 |
| 1037 | GUCGGUGG AGAA GCUG ACCAGAGAAACACACGUUGUGGUACAUUACCUGGUA | 773 | CAGCG GAC CCACCGAC | 788 |
| 1045 | GGCCGGGG AGAA GUGG ACCAGAGAAACACACGUUGUGGUACAUUACCUGGUA | 774 | CCACC GAC CCCCGGCC | 789 |
| 1410 | CAUCAUCA AGAA GCAG ACCAGAGAAACACACGUUGUGGUACAUUACCUGGUA | 775 | CUGCA GUU UGAUGAUG | 790 |
| 1453 | ACAGCUGG AGAA GUGC ACCAGAGAAACACACGUUGUGGUACAUUACCUGGUA | 776 | GCACA GAC CCAGCUGU | 791 |
| 1471 | GAUGCCAG AGAA GUGA ACCAGAGAAACACACGUUGUGGUACAUUACCUGGUA | 777 | UCACA GAC CUGGCAUC | 792 |

TABLE VII

Mouse rel A Hairpin Ribozyme/Target Sequences

| nt. Position | Hairpin Ribozyme sequence | Seq. ID No. | Substrate | Seq. ID No. |
|---|---|---|---|---|
| 137 | GUUGCUUC AGAA GUUC ACCAGAGAAACACACGUUGUGGUACAUUACCUGGUA | 793 | GAACA GCC GAAGCAAC | 812 |
| 273 | GAGAUUCG AGAA GUUC ACCAGAGAAACACACGUUGUGGUACAUUACCUGGUA | 794 | GAACA GUU CGAAUCUC | 813 |
| 343 | GCCAUCCC AGAA GUCC ACCAGAGAAACACACGUUGUGGUACAUUACCUGGUA | 795 | GGACU GCC GGGAUGGC | 814 |
| 366 | GGGCAGAG AGAA GCCU ACCAGAGAAACACACGUUGUGGUACAUUACCUGGUA | 796 | AGGCU GAC CUCUGCCC | 815 |
| 633 | UUGAGCUC AGAA GUGU ACCAGAGAAACACACGUUGUGGUACAUUACCUGGUA | 797 | ACACU GCC GAGCUCAA | 816 |
| 676 | CCCACCGA AGAA GCUC ACCAGAGAAACACACGUUGUGGUACAUUACCUGGUA | 798 | GAGCU GCC UCGGUGGG | 817 |
| 834 | AGGCUGGG AGAA GCGU ACCAGAGAAACACACGUUGUGGUACAUUACCUGGUA | 799 | ACGCC GAC CCCAGCCU | 818 |
| 881 | GAUCAGAA AGAA GCCG ACCAGAGAAACACACGUUGUGGUACAUUACCUGGUA | 800 | CGGCG GCC UUCUGAUC | 819 |
| 1100 | AGGUGUAG AGAA GCGG ACCAGAGAAACACACGUUGUGGUACAUUACCUGGUA | 801 | CCGCA GCC CUACACCU | 820 |
| 1205 | GGGCAGAG AGAA GUGC ACCAGAGAAACACACGUUGUGGUACAUUACCUGGUA | 802 | GCACC GUC CUCUGCCC | 821 |
| 1361 | GGGCUUCC AGAA GCGU ACCAGAGAAACACACGUUGUGGUACAUUACCUGGUA | 803 | ACGCU GUC GGAAGCCC | 822 |
| 1385 | CAGCAUCA AGAA GCAG ACCAGAGAAACACACGUUGUGGUACAUUACCUGGUA | 804 | CUGCA GUU UGAUGCUG | 823 |
| 1431 | ACUCCUGG AGAA GUGC ACCAGAGAAACACACGUUGUGGUACAUUACCUGGUA | 805 | GCACA GAC CCAGGAGU | 824 |
| 1449 | GAUGCCAG AGAA GUGA ACCAGAGAAACACACGUUGUGGUACAUUACCUGGUA | 806 | UCACA GAC CUGGCAUC | 825 |
| 1802 | AAGUCGGG AGAA GCUG ACCAGAGAAACACACGUUGUGGUACAUUACCUGGUA | 807 | CAGCU GCC CCCGACUU | 826 |
| 2009 | UGGCUCCA AGAA GUCC ACCAGAGAAACACACGUUGUGGUACAUUACCUGGUA | 808 | GGACA GAC UGGAGCCA | 827 |
| 2124 | UGGUGUCG AGAA GCAC ACCAGAGAAACACACGUUGUGGUACAUUACCUGGUA | 809 | GUGCU GCC CGACACCA | 828 |
| 2233 | AUUCUGAA AGAA GCCA ACCAGAGAAACACACGUUGUGGUACAUUACCUGGUA | 810 | UGGCC GCC UUCAGAAU | 829 |
| 2354 | UCAGUAAA AGAA GUCU ACCAGAGAAACACACGUUGUGGUACAUUACCUGGUA | 811 | AGACA GCC UUUACUGA | 830 |

What is claimed is:

1. A method for specifically cleaving RNA encoding a Rel-A subunit of NF-k B protein using an enzymatic RNA molecule, comprising the step of contacting said RNA with said enzymatic RNA molecule under conditions suitable for said cleaving.

2. The method of claim 1, wherein said enzymatic RNA molecule is in a motif selected from the group consisting of Hammerhead, Hairpin, Hepatitis Delta Virus, Group I Intron, RNAse P RNA and VSRNA.

3. A method of claim 1, wherein said enzymatic RNA molecule comprises between 12 and 100 nucleotides complementary to said RNA encoding the Rel-A subunit of the NF-kB protein.

4. A method of claim 1, wherein said enzymatic RNA molecule comprises between 14 and 24 nucleotides complementary to said RNA encoding the Rel-A subunit of the NF-kB protein.

* * * * *

SEQUENCE LISTING (1) GENERAL INFORMATION:

(iii) NUMBER OF SEQUENCES: 830

(2) INFORMATION FOR SEQ ID NO: 1:

(i) SEQUENCE CHARACTERISTICS:
       (A) LENGTH: 11
       (B) TYPE: nucleic acid
       (C) STRANDEDNESS: single
       (D) TOPOLOGY: linear (ix) FEATURE:
       (D) OTHER INFORMATION:  The letter "N" stands for
           any base.  "H" represents
           nucleotide C, A, or U.

(xi) SEQUENCE DESCRIPTION: SEQ ID NO: 1:

NNNNUHNNNN N                                                            11

(2) INFORMATION FOR SEQ ID NO: 2:

(i) SEQUENCE CHARACTERISTICS:
       (A) LENGTH: 32
       (B) TYPE: nucleic acid
       (C) STRANDEDNESS: single
       (D) TOPOLOGY: linear (ix) FEATURE:
       (D) OTHER INFORMATION:  The letter "N" stands for
           any base.

(xi) SEQUENCE DESCRIPTION: SEQ ID NO: 2:

NNNNNCUGAN GAGNNNNNNN NNNCGAAANN NN                                     32

(2) INFORMATION FOR SEQ ID NO: 3:

(i) SEQUENCE CHARACTERISTICS:
       (A) LENGTH: 14
       (B) TYPE: nucleic acid
       (C) STRANDEDNESS: single
       (D) TOPOLOGY: linear (ix) FEATURE:
       (D) OTHER INFORMATION:  The letter "N" stands for
           any base.

(xi) SEQUENCE DESCRIPTION: SEQ ID NO: 3:

NNNNNGUCNN NNNN                                                         14

(2) INFORMATION FOR SEQ ID NO: 4:

(i) SEQUENCE CHARACTERISTICS:
       (A) LENGTH: 50
       (B) TYPE: nucleic acid
       (C) STRANDEDNESS: single
       (D) TOPOLOGY: linear (ix) FEATURE:
       (D) OTHER INFORMATION:  The letter "N" stands for
           any base.

(xi) SEQUENCE DESCRIPTION: SEQ ID NO: 4:

NNNNNNAGAA NNNNACCAGA GAAACACACG UUGUGGUAUA UUACCUGGUA                   50

(2) INFORMATION FOR SEQ ID NO: 5:

(i) SEQUENCE CHARACTERISTICS:
    (A) LENGTH: 85
    (B) TYPE: nucleic acid
    (C) STRANDEDNESS: single
    (D) TOPOLOGY: linear (xi) SEQUENCE DESCRIPTION: SEQ ID NO: 5:

```
UGGCCGGCAU GGUCCCAGCC UCCUCGCUGG CGCCGGCUGG GCAACAUUCC GAGGGGACCG    60

UCCCCUCGGU AAUGGCGAAU GGGAC                                          85
```

(2) INFORMATION FOR SEQ ID NO: 6:

(i) SEQUENCE CHARACTERISTICS:
        (A) LENGTH: 176
        (B) TYPE: nucleic acid
        (C) STRANDEDNESS: single
        (D) TOPOLOGY: linear (xi) SEQUENCE DESCRIPTION: SEQ ID NO: 6:

```
GGGAAAGCUU GCGAAGGGCG UCGUCGCCCC GAGCGGUAGU AAGCAGGGAA CUCACCUCCA    60

AUUUCAGUAC UGAAAUUGUC GUAGCAGUUG ACUACUGUUA UGUGAUUGGU AGAGGCUAAG   120

UGACGGUAUU GGCGUAAGUC AGUAUUGCAG CACAGCACAA GCCCGCUUGC GAGAAU       176
```

(2) INFORMATION FOR SEQ ID NO: 7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 7:

```
AAUGGCUACA CAGGA                                                     15
```

(2) INFORMATION FOR SEQ ID NO: 8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 8:

```
AGCUCCUACG UGGUG                                                     15
```

(2) INFORMATION FOR SEQ ID NO: 9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 9:

```
CCUCCAUUGC GGACA                                                     15
```

(2) INFORMATION FOR SEQ ID NO: 10:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 10:

GAUCUGUUUC CCCUC          15

(2) INFORMATION FOR SEQ ID NO: 11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 11:

AUCUGUUUCC CCUCA          15

(2) INFORMATION FOR SEQ ID NO: 12:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 12:

UUCCCCUCAU CUUUC          15

(2) INFORMATION FOR SEQ ID NO: 13:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 13:

CCCUCAUCUU UCCCU          15

(2) INFORMATION FOR SEQ ID NO: 14:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 14:

CUCAUCUUUC CCUCA          15

(2) INFORMATION FOR SEQ ID NO: 15:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 15:

UCAUCUUUCC CUCAG          15

(2) INFORMATION FOR SEQ ID NO: 16:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 16:

CAGGCUUCUG GGCCU          15

(2) INFORMATION FOR SEQ ID NO: 17:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 17:

GGGCCUUAUG UGGAG                                          15

(2) INFORMATION FOR SEQ ID NO: 18:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 18:

UGGAGAUCAU CGAAC                                          15

(2) INFORMATION FOR SEQ ID NO: 19:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 19:

AGAUCAUCGA ACAGC                                          15

(2) INFORMATION FOR SEQ ID NO: 20:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 20:

AUGCGAUUCC GCUAU                                          15

(2) INFORMATION FOR SEQ ID NO: 21:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 21:

UGCGAUUCCG CUAUA                                          15

(2) INFORMATION FOR SEQ ID NO: 22:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 22:

UUCCGCUAUA AAUGC                                          15

(2) INFORMATION FOR SEQ ID NO: 23:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 23:

GGGCGCUCAG CGGGC                                     15

(2) INFORMATION FOR SEQ ID NO: 24:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 24:

GCAGUAUUCC UGGCG                                     15

(2) INFORMATION FOR SEQ ID NO: 25:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 25:

CACAGAUACC ACCAA                                     15

(2) INFORMATION FOR SEQ ID NO: 26:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 26:

CCACCAUCAA GAUCA                                     15

(2) INFORMATION FOR SEQ ID NO: 27:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 27:

UCAAGAUCAA UGGCU                                     15

(2) INFORMATION FOR SEQ ID NO: 28:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 28:

AAUGGCUACA CAGGA                                     15

(2) INFORMATION FOR SEQ ID NO: 29:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 29:

UUCGAAUCUC CCUGG                                                    15

(2) INFORMATION FOR SEQ ID NO: 30:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 30:

CGAAUCUCCC UGGUC                                                    15

(2) INFORMATION FOR SEQ ID NO: 31:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 31:

CCCUGGUCAC CAAGG                                                    15

(2) INFORMATION FOR SEQ ID NO: 32:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 32:

GGCCCCUCCU CCUGA                                                    15

(2) INFORMATION FOR SEQ ID NO: 33:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 33:

UCCACCUCAC CGGCC                                                    15

(2) INFORMATION FOR SEQ ID NO: 34:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 34:

CCGGCCUCAU CCACA                                                    15

(2) INFORMATION FOR SEQ ID NO: 35:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 35:

AUGAACUUGU GGGGA                                           15

(2) INFORMATION FOR SEQ ID NO: 36:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 36:

AGAUCAUCGA ACAGC                                           15

(2) INFORMATION FOR SEQ ID NO: 37:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 37:

GAUGGCUACU AUGAG                                           15

(2) INFORMATION FOR SEQ ID NO: 38:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 38:

AUGGUCUCUC CGGAG                                           15

(2) INFORMATION FOR SEQ ID NO: 39:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 39:

GGCUACUAUG AGGCU                                           15

(2) INFORMATION FOR SEQ ID NO: 40:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 40:

CUGACCUCUG CCCAG                                           15

(2) INFORMATION FOR SEQ ID NO: 41:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 41:

GCAGUAUCCA UAGCU                                                15

(2) INFORMATION FOR SEQ ID NO: 42:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 42:

CCGCAGUAUC CAUAG                                                15

(2) INFORMATION FOR SEQ ID NO: 43:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 43:

CAUAGCUUCC AGAAC                                                15

(2) INFORMATION FOR SEQ ID NO: 44:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 44:

AUAGCUUCCA GAACC                                                15

(2) INFORMATION FOR SEQ ID NO: 45:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 45:

UGGGGAUCCA GUGUG                                                15

(2) INFORMATION FOR SEQ ID NO: 46:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 46:

GGCUCCUUUU CUCAA                                                15

(2) INFORMATION FOR SEQ ID NO: 47:

(i) SEQUENCE CHARACTERISTICS:

(A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 47:

GCUCCUUUUC UCAAG                                                        15

(2) INFORMATION FOR SEQ ID NO: 48:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 48:

CUCCUUUUCU CAAGC                                                        15

(2) INFORMATION FOR SEQ ID NO: 49:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 49:

UCCUUUUCUC AAGCU                                                        15

(2) INFORMATION FOR SEQ ID NO: 50:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 50:

UGGCCAUUGU GUUCC                                                        15

(2) INFORMATION FOR SEQ ID NO: 51:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 51:

AUUGUGUUCC GGACU                                                        15

(2) INFORMATION FOR SEQ ID NO: 52:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 52:

UUGUGUUCCG GACUC                                                        15

(2) INFORMATION FOR SEQ ID NO: 53:

(i) SEQUENCE CHARACTERISTICS:
        (A) LENGTH: 15 base pairs (B) TYPE: nucleic acid
        (C) STRANDEDNESS: single
        (D) TOPOLOGY: linear (xi) SEQUENCE DESCRIPTION: SEQ ID NO: 53:

GACUCCUCCG UACGC                                          15

(2) INFORMATION FOR SEQ ID NO: 54:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 54:

CCUCCGUACG CCGAC                                          15

(2) INFORMATION FOR SEQ ID NO: 55:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 55:

CCAGGCUCCU GUUCG                                          15

(2) INFORMATION FOR SEQ ID NO: 56:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 56:

UUCGAGUCUC CAUGC                                          15

(2) INFORMATION FOR SEQ ID NO: 57:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 57:

CGAGUCUCCA UGCAG                                          15

(2) INFORMATION FOR SEQ ID NO: 58:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 58:

GCGGCCUUCU GAUCG                                          15

(2) INFORMATION FOR SEQ ID NO: 59:

(i) SEQUENCE CHARACTERISTICS:
        (A) LENGTH: 15 base pairs
        (B) TYPE: nucleic acid (C) STRANDEDNESS: single
            (D) TOPOLOGY: linear (xi) SEQUENCE DESCRIPTION: SEQ ID NO: 59:

CGGCCUUCUG AUCGC                                                            15

(2) INFORMATION FOR SEQ ID NO: 60:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 60:

GCGAGCUCAG UGAGC                                                            15

(2) INFORMATION FOR SEQ ID NO: 61:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 61:

AUGGAGUUCC AGUAC                                                            15

(2) INFORMATION FOR SEQ ID NO: 62:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 62:

UGGAGUUCCA GUACU                                                            15

(2) INFORMATION FOR SEQ ID NO: 63:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 63:

UUCCAGUACU UGCCA                                                            15

(2) INFORMATION FOR SEQ ID NO: 64:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 64:

GCCUCAUCCA CAUGA                                                            15

(2) INFORMATION FOR SEQ ID NO: 65:

(i) SEQUENCE CHARACTERISTICS:
            (A) LENGTH: 15 base pairs
            (B) TYPE: nucleic acid
            (C) STRANDEDNESS: single (D) TOPOLOGY: linear (xi) SEQUENCE DESCRIPTION: SEQ ID NO: 65:

AGAUGAUCGC CACCG                                                    15

(2) INFORMATION FOR SEQ ID NO: 66:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 66:

CAGUACUUGC CAGAC                                                    15

(2) INFORMATION FOR SEQ ID NO: 67:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 67:

ACCGGAUUGA AGAGA                                                    15

(2) INFORMATION FOR SEQ ID NO: 68:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 68:

GAGACCUUCA AGAGU                                                    15

(2) INFORMATION FOR SEQ ID NO: 69:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 69:

AGGACCUAUG AGACC                                                    15

(2) INFORMATION FOR SEQ ID NO: 70:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 70:

GAGACCUUCA AGAGU                                                    15

(2) INFORMATION FOR SEQ ID NO: 71:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 71:

AGACCUUCAA GAGUA                                                              15

(2) INFORMATION FOR SEQ ID NO: 72:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 72:

AGAGUAUCAU GAAGA                                                              15

(2) INFORMATION FOR SEQ ID NO: 73:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 73:

GAAGAGUCCU UUCAA                                                              15

(2) INFORMATION FOR SEQ ID NO: 74:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 74:

GAGUCCUUUC AAUGG                                                              15

(2) INFORMATION FOR SEQ ID NO: 75:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 75:

AGUCCUUUCA AUGGA                                                              15

(2) INFORMATION FOR SEQ ID NO: 76:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 76:

GUCCUUUCAA UGGAC                                                              15

(2) INFORMATION FOR SEQ ID NO: 77:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 77:

CCGGCCUCCA ACCCG                                                15

(2) INFORMATION FOR SEQ ID NO: 78:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 78:

UACACCUUGA UCCAA                                                15

(2) INFORMATION FOR SEQ ID NO: 79:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 79:

GGCGUAUUGC UGUGC                                                15

(2) INFORMATION FOR SEQ ID NO: 80:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 80:

UGUGCCUACC CGAAA                                                15

(2) INFORMATION FOR SEQ ID NO: 81:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 81:

AAGCCUUCCC GAAGU                                                15

(2) INFORMATION FOR SEQ ID NO: 82:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 82:

CGAAACUCAA CUUCU                                                15

(2) INFORMATION FOR SEQ ID NO: 83:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 83:

CUCAACUUCU GUCCC                                                    15

(2) INFORMATION FOR SEQ ID NO: 84:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 84:

UCAACUUCUG UCCCC                                                    15

(2) INFORMATION FOR SEQ ID NO: 85:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 85:

CUUCUGUCCC CAAGC                                                    15

(2) INFORMATION FOR SEQ ID NO: 86:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 86:

CAGCCCUACA CCUUC                                                    15

(2) INFORMATION FOR SEQ ID NO: 87:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 87:

GCCAUAUAGC CUUAC                                                    15

(2) INFORMATION FOR SEQ ID NO: 88:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 88:

CAUCCCUCAG CACCA                                                    15

(2) INFORMATION FOR SEQ ID NO: 89:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 89:

ACACCUUCCC AGCAU                    15

(2) INFORMATION FOR SEQ ID NO: 90:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 90:

UCCAUCUCCA GCUUC                    15

(2) INFORMATION FOR SEQ ID NO: 91:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 91:

UUUACUUUAG CGCGC                    15

(2) INFORMATION FOR SEQ ID NO: 92:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 92:

CCAGCAUCCC UCAGC                    15

(2) INFORMATION FOR SEQ ID NO: 93:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 93:

GCACCAUCAA CUUUG                    15

(2) INFORMATION FOR SEQ ID NO: 94:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 94:

AUCAACUUUG AUGAG                    15

(2) INFORMATION FOR SEQ ID NO: 95:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 95:

GAAGACUUCU CCUCC                    15

(2) INFORMATION FOR SEQ ID NO: 96:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 96:

AAGACUUCUC CUCCA                                15

(2) INFORMATION FOR SEQ ID NO: 97:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 97:

GACUUCUCCU CCAUU                                15

(2) INFORMATION FOR SEQ ID NO: 98:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 98:

UUCUCCUCCA UUGCG                                15

(2) INFORMATION FOR SEQ ID NO: 99:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 99:

CCUCCAUUGC GGACA                                15

(2) INFORMATION FOR SEQ ID NO: 100:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 100:

AUGGACUUCU CUGCU                                15

(2) INFORMATION FOR SEQ ID NO: 101:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 101:

UGGACUUCUC UGCUC                                15

(2) INFORMATION FOR SEQ ID NO: 102:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 102:

GACUUCUCUG CUCUU                                      15

(2) INFORMATION FOR SEQ ID NO: 103:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 103:

UUUGAGUCAG AUCAG                                      15

(2) INFORMATION FOR SEQ ID NO: 104:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 104:

GUCAGAUCAG CUCCU                                      15

(2) INFORMATION FOR SEQ ID NO: 105:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 105:

AUCAGCUCCU AAGGU                                      15

(2) INFORMATION FOR SEQ ID NO: 106:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 106:

AGCUCCUAAG GUGCU                                      15

(2) INFORMATION FOR SEQ ID NO: 107:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 107:

CAGUGCUCCC AAGAG                                      15

(2) INFORMATION FOR SEQ ID NO: 108:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 108:

CCAGGCUCCU GUUCG         15

(2) INFORMATION FOR SEQ ID NO: 109:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 109:

AAGCCAUUAG CCAGC         15

(2) INFORMATION FOR SEQ ID NO: 110:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 110:

UUUGAGUCAG AUCAG         15

(2) INFORMATION FOR SEQ ID NO: 111:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 111:

AGCGAAUCCA GACCA         15

(2) INFORMATION FOR SEQ ID NO: 112:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 112:

AACCCCUUUC ACGUU         15

(2) INFORMATION FOR SEQ ID NO: 113:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 113:

ACCCCUUUCA CGUUC         15

(2) INFORMATION FOR SEQ ID NO: 114:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 114:

UUCACGUUCC UAUAG                                                            15

(2) INFORMATION FOR SEQ ID NO: 115:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 115:

UCACGUUCCU AUAGA                                                            15

(2) INFORMATION FOR SEQ ID NO: 116:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 116:

CGUUCCUAUA GAGGA                                                            15

(2) INFORMATION FOR SEQ ID NO: 117:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 117:

UUCCUAUAGA GGAGC                                                            15

(2) INFORMATION FOR SEQ ID NO: 118:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 118:

GGGGACUAUG ACUUG                                                            15

(2) INFORMATION FOR SEQ ID NO: 119:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 119:

UGCGCCUCUG CUUCC                                                            15

(2) INFORMATION FOR SEQ ID NO: 120:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 120:

CUCUGCUUCC AGGUG                                          15

(2) INFORMATION FOR SEQ ID NO: 121:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 121:

UCUGCUUCCA GGUGA                                          15

(2) INFORMATION FOR SEQ ID NO: 122:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 122:

AAGCCAUUAG CCAGC                                          15

(2) INFORMATION FOR SEQ ID NO: 123:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 123:

GGCCCCUCCU CCUGA                                          15

(2) INFORMATION FOR SEQ ID NO: 124:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 124:

CCCCUGUCCU CUCAC                                          15

(2) INFORMATION FOR SEQ ID NO: 125:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 125:

CUGUCCUCUC ACAUC                                          15

(2) INFORMATION FOR SEQ ID NO: 126:

(i) SEQUENCE CHARACTERISTICS:

```
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 126:

GUCCCUUCCU CAGCC                                                15

(2) INFORMATION FOR SEQ ID NO: 127:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 127:

CCUUCCUCAG CCAUG                                                15

(2) INFORMATION FOR SEQ ID NO: 128:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 128:

UCCUGCUUCC AUCUC                                                15

(2) INFORMATION FOR SEQ ID NO: 129:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 129:

AUCCGAUUUU UGAUA                                                15

(2) INFORMATION FOR SEQ ID NO: 130:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 130:

CCGAUUUUUG AUAAC                                                15

(2) INFORMATION FOR SEQ ID NO: 131:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 131:

CGAUUUUUGA UAACC                                                15

(2) INFORMATION FOR SEQ ID NO: 132:

(i) SEQUENCE CHARACTERISTICS:
        (A) LENGTH: 15 base pairs
```

(B) TYPE: nucleic acid
(C) STRANDEDNESS: single
(D) TOPOLOGY: linear (xi) SEQUENCE DESCRIPTION: SEQ ID NO: 132:

UGGCCAUUGU GUUCC                                       15

(2) INFORMATION FOR SEQ ID NO: 133:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 133:

CCGAGCUCAA GAUCU                                       15

(2) INFORMATION FOR SEQ ID NO: 134:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 134:

UCAAGAUCUG CCGAG                                       15

(2) INFORMATION FOR SEQ ID NO: 135:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 135:

CGGAACUCUG GGAGC                                       15

(2) INFORMATION FOR SEQ ID NO: 136:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 136:

GCUGCCUCGG UGGGG                                       15

(2) INFORMATION FOR SEQ ID NO: 137:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 137:

AUGAGAUCUU CUUGC                                       15

(2) INFORMATION FOR SEQ ID NO: 138:

(i) SEQUENCE CHARACTERISTICS:
        (A) LENGTH: 15 base pairs
        (B) TYPE: nucleic acid (C) STRANDEDNESS: single
            (D) TOPOLOGY: linear (xi) SEQUENCE DESCRIPTION: SEQ ID NO: 138:

GAGAUCUUCU UGCUG                                                          15

(2) INFORMATION FOR SEQ ID NO: 139:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 139:

AGAUCUUCUU GCUGU                                                          15

(2) INFORMATION FOR SEQ ID NO: 140:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 140:

UUCUCCUCCA UUGCG                                                          15

(2) INFORMATION FOR SEQ ID NO: 141:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 141:

AAGACAUUGA GGUGU                                                          15

(2) INFORMATION FOR SEQ ID NO: 142:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 142:

GAGGUGUAUU UCACG                                                          15

(2) INFORMATION FOR SEQ ID NO: 143:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 143:

GGUGUAUUUC ACGGG                                                          15

(2) INFORMATION FOR SEQ ID NO: 144:

(i) SEQUENCE CHARACTERISTICS:
            (A) LENGTH: 15 base pairs
            (B) TYPE: nucleic acid
            (C) STRANDEDNESS: single (D) TOPOLOGY: linear (xi) SEQUENCE DESCRIPTION: SEQ ID NO: 144:

GUGUAUUUCA CGGGA                                                        15

(2) INFORMATION FOR SEQ ID NO: 145:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 145:

UGUAUUUCAC GGGAC                                                        15

(2) INFORMATION FOR SEQ ID NO: 146:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 146:

CGAGGCUCCU UUUCU                                                        15

(2) INFORMATION FOR SEQ ID NO: 147:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 147:

GAUGAGUUUU CCCCC                                                        15

(2) INFORMATION FOR SEQ ID NO: 148:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 148:

AUGAGUUUUC CCCCA                                                        15

(2) INFORMATION FOR SEQ ID NO: 149:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 149:

UGAGUUUUCC CCCAU                                                        15

(2) INFORMATION FOR SEQ ID NO: 150:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 150:

AUGCUGUUAC CAUCA                                            15

(2) INFORMATION FOR SEQ ID NO: 151:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 151:

UGCUGUUACC AUCAG                                            15

(2) INFORMATION FOR SEQ ID NO: 152:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 152:

GGCCCCUCCU CCUGA                                            15

(2) INFORMATION FOR SEQ ID NO: 153:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 153:

GUCCCUUCCU CAGCC                                            15

(2) INFORMATION FOR SEQ ID NO: 154:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 154:

UUACCAUCAG GGCAG                                            15

(2) INFORMATION FOR SEQ ID NO: 155:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 155:

GGGAGUUUAG UCUGA                                            15

(2) INFORMATION FOR SEQ ID NO: 156:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 156:

CAGCCCUACA CCUUC                                                15

(2) INFORMATION FOR SEQ ID NO: 157:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 157:

CUGGCCUUAG CACCG                                                15

(2) INFORMATION FOR SEQ ID NO: 158:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 158:

GGUCCCUUCC UCAGC                                                15

(2) INFORMATION FOR SEQ ID NO: 159:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 159:

CCCAGCUCCU GCCCC                                                15

(2) INFORMATION FOR SEQ ID NO: 160:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 160:

CCAGCCUCCA GGCUC                                                15

(2) INFORMATION FOR SEQ ID NO: 161:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 161:

CCCAGCUCCU GCCCC                                                15

(2) INFORMATION FOR SEQ ID NO: 162:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 162:

CCAUGGUCCC UUCCU                                                                15

(2) INFORMATION FOR SEQ ID NO: 163:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 163:

GUGGGCUCAG CUGCG                                                                15

(2) INFORMATION FOR SEQ ID NO: 164:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 164:

AUGAGUUUUC CCCCA                                                                15

(2) INFORMATION FOR SEQ ID NO: 165:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 165:

CUCCUGUUCG AGUCU                                                                15

(2) INFORMATION FOR SEQ ID NO: 166:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 166:

CCCCAGUUCU AACCC                                                                15

(2) INFORMATION FOR SEQ ID NO: 167:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 167:

CAGUUCUAAC CCCGG                                                                15

(2) INFORMATION FOR SEQ ID NO: 168:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 168:

```
GGGUCCUCCC CAGUC                                                15
```

(2) INFORMATION FOR SEQ ID NO: 169:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 169:

```
CUUUUCUCAA GCUGA                                                15
```

(2) INFORMATION FOR SEQ ID NO: 170:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 170:

```
ACGCUGUCGG AAGCC                                                15
```

(2) INFORMATION FOR SEQ ID NO: 171:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 171:

```
CUGCAGUUUG AUGCU                                                15
```

(2) INFORMATION FOR SEQ ID NO: 172:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 172:

```
UGCAGUUUGA UGCUG                                                15
```

(2) INFORMATION FOR SEQ ID NO: 173:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 173:

```
GGGGCCUUGC UUGGC                                                15
```

(2) INFORMATION FOR SEQ ID NO: 174:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 174:

```
CCUUGCUUGG CAACA                                                15
```

(2) INFORMATION FOR SEQ ID NO: 175:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 175:

GGAGUGUUCA CAGAC                                        15

(2) INFORMATION FOR SEQ ID NO: 176:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 176:

GAGUGUUCAC AGACC                                        15

(2) INFORMATION FOR SEQ ID NO: 177:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 177:

CUGGCAUCUG UGGAC                                        15

(2) INFORMATION FOR SEQ ID NO: 178:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 178:

CUUCGGUAGG GAACU                                        15

(2) INFORMATION FOR SEQ ID NO: 179:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 179:

GACAACUCAG AGUUU                                        15

(2) INFORMATION FOR SEQ ID NO: 180:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 180:

UCAGAGUUUC AGCAG                                        15

(2) INFORMATION FOR SEQ ID NO: 181:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 181:

CAGAGUUUCA GCAGC                                            15

(2) INFORMATION FOR SEQ ID NO: 182:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 182:

AGAGUUUCAG CAGCU                                            15

(2) INFORMATION FOR SEQ ID NO: 183:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 183:

GGUGCAUCCC UGUGU                                            15

(2) INFORMATION FOR SEQ ID NO: 184:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 184:

AUGGAGUACC CUGAA                                            15

(2) INFORMATION FOR SEQ ID NO: 185:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 185:

UGAAGCUAUA ACUCG                                            15

(2) INFORMATION FOR SEQ ID NO: 186:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 186:

AAGCUAUAAC UCGCC                                            15

(2) INFORMATION FOR SEQ ID NO: 187:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 187:

UAUAACUCGC CUGGU                                                           15

(2) INFORMATION FOR SEQ ID NO: 188:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 188:

CUCUCCUAGA GAGGG                                                           15

(2) INFORMATION FOR SEQ ID NO: 189:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 189:

CCCAGCUCCU GCCCC                                                           15

(2) INFORMATION FOR SEQ ID NO: 190:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 190:

UCCUGCUUCG GUAGG                                                           15

(2) INFORMATION FOR SEQ ID NO: 191:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 191:

CGGGGCUUCC CAAUG                                                           15

(2) INFORMATION FOR SEQ ID NO: 192:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 192:

CUGACCUCUG CCCAG                                                           15

(2) INFORMATION FOR SEQ ID NO: 193:

```
        (i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 193:

CUCUGCUUCC AGGUG                                                       15

(2) INFORMATION FOR SEQ ID NO: 194:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 194:

UCUGCUUCCA GGUGA                                                       15

(2) INFORMATION FOR SEQ ID NO: 195:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 195:

CUCGCUUUCG GAGGU                                                       15

(2) INFORMATION FOR SEQ ID NO: 196:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 196:

AAUGGCUCGU CUGUA                                                       15

(2) INFORMATION FOR SEQ ID NO: 197:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 197:

GGCUCGUCUG UAGUG                                                       15

(2) INFORMATION FOR SEQ ID NO: 198:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 198:

CGUCUGUAGU GCACG                                                       15

(2) INFORMATION FOR SEQ ID NO: 199:
```

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 199:

GAACUGUUCC CCCUC                                                        15

(2) INFORMATION FOR SEQ ID NO: 200:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 200:

AACUGUUCCC CCUCA                                                        15

(2) INFORMATION FOR SEQ ID NO: 201:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 201:

UCCCCCUCAU CUUCC                                                        15

(2) INFORMATION FOR SEQ ID NO: 202:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 202:

CCCUCAUCUU CCCGG                                                        15

(2) INFORMATION FOR SEQ ID NO: 203:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 203:

CUCAUCUUCC CGGCA                                                        15

(2) INFORMATION FOR SEQ ID NO: 204:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 204:

UCAUCUUCCC GGCAG                                                        15

(2) INFORMATION FOR SEQ ID NO: 205:

(i) SEQUENCE CHARACTERISTICS:

(A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 205:

CAGGCCUCUG GCCCC                                                        15

(2) INFORMATION FOR SEQ ID NO: 206:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 206:

GGCCCCUAUG UGGAG                                                        15

(2) INFORMATION FOR SEQ ID NO: 207:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 207:

UGGAGAUCAU UGAGC                                                        15

(2) INFORMATION FOR SEQ ID NO: 208:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 208:

AGAUCAUUGA GCAGC                                                        15

(2) INFORMATION FOR SEQ ID NO: 209:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 209:

AUGCGCUUCC GCUAC                                                        15

(2) INFORMATION FOR SEQ ID NO: 210:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 210:

UGCGCUUCCG CUACA                                                        15

(2) INFORMATION FOR SEQ ID NO: 211:

(i) SEQUENCE CHARACTERISTICS:
        (A) LENGTH: 15 base pairs

```
        (B) TYPE: nucleic acid
        (C) STRANDEDNESS: single
        (D) TOPOLOGY: linear (xi) SEQUENCE DESCRIPTION: SEQ ID NO: 211:

UUCCGCUACA AGUGC                                                    15

(2) INFORMATION FOR SEQ ID NO: 212:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 212:

GGGCGCUCCG CGGGC                                                    15

(2) INFORMATION FOR SEQ ID NO: 213:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 213:

GCAGCAUCCC AGGCG                                                    15

(2) INFORMATION FOR SEQ ID NO: 214:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 214:

CACAGAUACC ACCAA                                                    15

(2) INFORMATION FOR SEQ ID NO: 215:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 215:

CCACCAUCAA GAUCA                                                    15

(2) INFORMATION FOR SEQ ID NO: 216:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 216:

UCAAGAUCAA UGGCU                                                    15

(2) INFORMATION FOR SEQ ID NO: 217:

(i) SEQUENCE CHARACTERISTICS:
        (A) LENGTH: 15 base pairs
        (B) TYPE: nucleic acid
```

(C) STRANDEDNESS: single
        (D) TOPOLOGY: linear (xi) SEQUENCE DESCRIPTION: SEQ ID NO: 217:

AAUGGCUACA CAGGA                                                            15

(2) INFORMATION FOR SEQ ID NO: 218:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 218:

UGCGCAUCUC CCUGG                                                            15

(2) INFORMATION FOR SEQ ID NO: 219:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 219:

CGCAUCUCCC UGGUC                                                            15

(2) INFORMATION FOR SEQ ID NO: 220:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 220:

CCCUGGUCAC CAAGG                                                            15

(2) INFORMATION FOR SEQ ID NO: 221:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 221:

GGACCCUCCU CACCG                                                            15

(2) INFORMATION FOR SEQ ID NO: 222:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 222:

CCCUCCUCAC CGGCC                                                            15

(2) INFORMATION FOR SEQ ID NO: 223:

(i) SEQUENCE CHARACTERISTICS:
        (A) LENGTH: 15 base pairs
        (B) TYPE: nucleic acid
        (C) STRANDEDNESS: single (D) TOPOLOGY: linear (xi) SEQUENCE DESCRIPTION: SEQ ID NO: 223:

CCGGCCUCAC CCCCA                                                    15

(2) INFORMATION FOR SEQ ID NO: 224:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 224:

ACGAGCUUGU AGGAA                                                    15

(2) INFORMATION FOR SEQ ID NO: 225:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 225:

AGCUUGUAGG AAAGG                                                    15

(2) INFORMATION FOR SEQ ID NO: 226:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 226:

GAUGGCUUCU AUGAG                                                    15

(2) INFORMATION FOR SEQ ID NO: 227:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 227:

AUGGCUUCUA UGAGG                                                    15

(2) INFORMATION FOR SEQ ID NO: 228:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 228:

GGCUUCUAUG AGGCU                                                    15

(2) INFORMATION FOR SEQ ID NO: 229:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 229:

CUGAGCUCUG CCCGG                                                        15

(2) INFORMATION FOR SEQ ID NO: 230:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 230:

GCUGCAUCCA CAGUU                                                        15

(2) INFORMATION FOR SEQ ID NO: 231:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 231:

CCACAGUUUC CAGAA                                                        15

(2) INFORMATION FOR SEQ ID NO: 232:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 232:

CACAGUUUCC AGAAC                                                        15

(2) INFORMATION FOR SEQ ID NO: 233:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 233:

ACAGUUUCCA GAACC                                                        15

(2) INFORMATION FOR SEQ ID NO: 234:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 234:

UGGGAAUCCA GUGUG                                                        15

(2) INFORMATION FOR SEQ ID NO: 235:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 235:

GGCUCCUUUU CGCAA                                                    15

(2) INFORMATION FOR SEQ ID NO: 236:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 236:

GCUCCUUUUC GCAAG                                                    15

(2) INFORMATION FOR SEQ ID NO: 237:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 237:

CUCCUUUUCG CAAGC                                                    15

(2) INFORMATION FOR SEQ ID NO: 238:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 238:

UCCUUUUCGC AAGCU                                                    15

(2) INFORMATION FOR SEQ ID NO: 239:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 239:

UGGCCAUUGU GUUCC                                                    15

(2) INFORMATION FOR SEQ ID NO: 240:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 240:

AUUGUGUUCC GGACC                                                    15

(2) INFORMATION FOR SEQ ID NO: 241:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 241:

UUGUGUUCCG GACCC                                                   15

(2) INFORMATION FOR SEQ ID NO: 242:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 242:

GACCCCUCCC UACGC                                                   15

(2) INFORMATION FOR SEQ ID NO: 243:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 243:

CCUCCCUACG CAGAC                                                   15

(2) INFORMATION FOR SEQ ID NO: 244:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 244:

GCAGGCUCCU GUGCG                                                   15

(2) INFORMATION FOR SEQ ID NO: 245:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 245:

UGCGUGUCUC CAUGC                                                   15

(2) INFORMATION FOR SEQ ID NO: 246:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 246:

CGUGUCUCCA UGCAG                                                   15

(2) INFORMATION FOR SEQ ID NO: 247:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 247:

```
GCGGCCUUCC GACCG                                                          15

(2) INFORMATION FOR SEQ ID NO: 248:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 248:

CGGCCUUCCG ACCGG                                                          15

(2) INFORMATION FOR SEQ ID NO: 249:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 249:

GGGAGCUCAG UGAGC                                                          15

(2) INFORMATION FOR SEQ ID NO: 250:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 250:

AUGGAAUUCC AGUAC                                                          15

(2) INFORMATION FOR SEQ ID NO: 251:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 251:

UGGAAUUCCA GUACC                                                          15

(2) INFORMATION FOR SEQ ID NO: 252:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 252:

UUCCAGUACC UGCCA                                                          15

(2) INFORMATION FOR SEQ ID NO: 253:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 253:

GCCAGAUACA GACGA                                                          15
```

(2) INFORMATION FOR SEQ ID NO: 254:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 254:

AGACGAUCGU CACCG        15

(2) INFORMATION FOR SEQ ID NO: 255:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 255:

CGAUCGUCAC CGGAU        15

(2) INFORMATION FOR SEQ ID NO: 256:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 256:

ACCGGAUUGA GGAGA        15

(2) INFORMATION FOR SEQ ID NO: 257:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 257:

GAAACGUAAA AGGAC        15

(2) INFORMATION FOR SEQ ID NO: 258:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 258:

AGGACAUAUG AGACC        15

(2) INFORMATION FOR SEQ ID NO: 259:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 259:

GAGACCUUCA AGAGC        15

(2) INFORMATION FOR SEQ ID NO: 260:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 260:

AGACCUUCAA GAGCA                        15

(2) INFORMATION FOR SEQ ID NO: 261:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 261:

AGAGCAUCAU GAAGA                        15

(2) INFORMATION FOR SEQ ID NO: 262:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 262:

GAAGAGUCCU UUCAG                        15

(2) INFORMATION FOR SEQ ID NO: 263:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 263:

GAGUCCUUUC AGCGG                        15

(2) INFORMATION FOR SEQ ID NO: 264:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 264:

AGUCCUUUCA GCGGA                        15

(2) INFORMATION FOR SEQ ID NO: 265:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 265:

GUCCUUUCAG CGGAC                        15

(2) INFORMATION FOR SEQ ID NO: 266:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 266:

CCGGCCUCCA CCUCG                                                        15

(2) INFORMATION FOR SEQ ID NO: 267:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 267:

UCCACCUCGA CGCAU                                                        15

(2) INFORMATION FOR SEQ ID NO: 268:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 268:

GACGCAUUGC UGUGC                                                        15

(2) INFORMATION FOR SEQ ID NO: 269:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 269:

UGUGCCUUCC CGCAG                                                        15

(2) INFORMATION FOR SEQ ID NO: 270:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 270:

GUGCCUUCCC GCAGC                                                        15

(2) INFORMATION FOR SEQ ID NO: 271:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 271:

CGCAGCUCAG CUUCU                                                        15

(2) INFORMATION FOR SEQ ID NO: 272:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO: 272:

CUCAGCUUCU GUCCC                                                        15

(2) INFORMATION FOR SEQ ID NO: 273:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 273:

UCAGCUUCUG UCCCC                                                        15

(2) INFORMATION FOR SEQ ID NO: 274:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 274:

CUUCUGUCCC CAAGC                                                        15

(2) INFORMATION FOR SEQ ID NO: 275:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 275:

CAGCCCUAUC CCUUU                                                        15

(2) INFORMATION FOR SEQ ID NO: 276:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 276:

GCCCUAUCCC UUUAC                                                        15

(2) INFORMATION FOR SEQ ID NO: 277:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 277:

UAUCCCUUUA CGUCA                                                        15

(2) INFORMATION FOR SEQ ID NO: 278:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 278:

AUCCCUUUAC GUCAU                                                        15

(2) INFORMATION FOR SEQ ID NO: 279:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 279:

UCCCUUUACG UCAUC                                                        15

(2) INFORMATION FOR SEQ ID NO: 280:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 280:

UUUACGUCAU CCCUG                                                        15

(2) INFORMATION FOR SEQ ID NO: 281:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 281:

ACGUCAUCCC UGAGC                                                        15

(2) INFORMATION FOR SEQ ID NO: 282:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 282:

GCACCAUCAA CUAUG                                                        15

(2) INFORMATION FOR SEQ ID NO: 283:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 283:

AUCAACUAUG AUGAG                                                        15

(2) INFORMATION FOR SEQ ID NO: 284:

(i) SEQUENCE CHARACTERISTICS:

(A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 284:

GAAGACUUCU CCUCC                                                              15

(2) INFORMATION FOR SEQ ID NO: 285:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 285:

AAGACUUCUC CUCCA                                                              15

(2) INFORMATION FOR SEQ ID NO: 286:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 286:

GACUUCUCCU CCAUU                                                              15

(2) INFORMATION FOR SEQ ID NO: 287:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 287:

UUCUCCUCCA UUGCG                                                              15

(2) INFORMATION FOR SEQ ID NO: 288:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 288:

CCUCCAUUGC GGACA                                                              15

(2) INFORMATION FOR SEQ ID NO: 289:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 289:

AUGGACUUCU CAGCC                                                              15

(2) INFORMATION FOR SEQ ID NO: 290:

(i) SEQUENCE CHARACTERISTICS:
        (A) LENGTH: 15 base pairs (B) TYPE: nucleic acid
            (C) STRANDEDNESS: single
            (D) TOPOLOGY: linear (xi) SEQUENCE DESCRIPTION: SEQ ID NO: 290:

UGGACUUCUC AGCCC                                                        15

(2) INFORMATION FOR SEQ ID NO: 291:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 291:

GACUUCUCAG CCCUG                                                        15

(2) INFORMATION FOR SEQ ID NO: 292:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 292:

GCUGAGUCAG AUCAG                                                        15

(2) INFORMATION FOR SEQ ID NO: 293:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 293:

GUCAGAUCAG CUCCU                                                        15

(2) INFORMATION FOR SEQ ID NO: 294:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 294:

AUCAGCUCCU AAGGG                                                        15

(2) INFORMATION FOR SEQ ID NO: 295:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 295:

AGCUCCUAAG GGGGU                                                        15

(2) INFORMATION FOR SEQ ID NO: 296:

(i) SEQUENCE CHARACTERISTICS:
            (A) LENGTH: 15 base pairs
            (B) TYPE: nucleic acid (C) STRANDEDNESS: single
                (D) TOPOLOGY: linear (xi) SEQUENCE DESCRIPTION: SEQ ID NO: 296:

CUGCCCUCCC CAGAG                                                    15

(2) INFORMATION FOR SEQ ID NO: 297:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 297:

GCAGGCUAUC AGUCA                                                    15

(2) INFORMATION FOR SEQ ID NO: 298:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 298:

AGGCUAUCAG UCAGC                                                    15

(2) INFORMATION FOR SEQ ID NO: 299:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 299:

UAUCAGUCAG CGCAU                                                    15

(2) INFORMATION FOR SEQ ID NO: 300:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 300:

AGCGCAUCCA GACCA                                                    15

(2) INFORMATION FOR SEQ ID NO: 301:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO: 301:

AACCCCUUCC AAGUU                                                    15

(2) INFORMATION FOR SEQ ID NO: 302:

(i) SEQUENCE CHARACTERISTICS:
                (A) LENGTH: 15 base pairs
                (B) TYPE: nucleic acid
                (C) STRANDEDNESS: single (D) TOPOLOGY: linear (xi) SEQUENCE DESCRIPTION: SEQ ID NO: 302:

ACCCCUUCCA AGUUC                                                    15

(2) INFORMATION FOR SEQ ID NO: 303:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 303:

UCCAAGUUCC UAUAG                                                    15

(2) INFORMATION FOR SEQ ID NO: 304:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 304:

CCAAGUUCCU AUAGA                                                    15

(2) INFORMATION FOR SEQ ID NO: 305:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 305:

AGUUCCUAUA GAAGA                                                    15

(2) INFORMATION FOR SEQ ID NO: 306:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 306:

UUCCUAUAGA AGAGC                                                    15

(2) INFORMATION FOR SEQ ID NO: 307:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 307:

GGGGACUACG ACCUG                                                    15

(2) INFORMATION FOR SEQ ID NO: 308:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 308:

UGCGGCUCUG CUUCC                                                                 15

(2) INFORMATION FOR SEQ ID NO: 309:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 309:

CUCUGCUUCC AGGUG                                                                 15

(2) INFORMATION FOR SEQ ID NO: 310:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 310:

UCUGCUUCCA GGUGA                                                                 15

(2) INFORMATION FOR SEQ ID NO: 311:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 311:

GACCCAUCAG GCAGG                                                                 15

(2) INFORMATION FOR SEQ ID NO: 312:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 312:

GGCCCCUCCG CCUGC                                                                 15

(2) INFORMATION FOR SEQ ID NO: 313:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 313:

CGCCUGUCCU UCCUC                                                                 15

(2) INFORMATION FOR SEQ ID NO: 314:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 314:

CUGUCCUUCC UCAUC                    15

(2) INFORMATION FOR SEQ ID NO: 315:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 315:

UGUCCUUCCU CAUCC                    15

(2) INFORMATION FOR SEQ ID NO: 316:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 316:

CCUUCCUCAU CCCAU                    15

(2) INFORMATION FOR SEQ ID NO: 317:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 317:

UCCUCAUCCC AUCUU                    15

(2) INFORMATION FOR SEQ ID NO: 318:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 318:

AUCCCAUCUU UGACA                    15

(2) INFORMATION FOR SEQ ID NO: 319:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 319:

CCCAUCUUUG ACAAU                    15

(2) INFORMATION FOR SEQ ID NO: 320:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 320:

CCAUCUUUGA CAAUC                                                    15

(2) INFORMATION FOR SEQ ID NO: 321:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 321:

UGACAAUCGU GCCCC                                                    15

(2) INFORMATION FOR SEQ ID NO: 322:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 322:

CCGAGCUCAA GAUCU                                                    15

(2) INFORMATION FOR SEQ ID NO: 323:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 323:

UCAAGAUCUG CCGAG                                                    15

(2) INFORMATION FOR SEQ ID NO: 324:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 324:

CGAAACUCUG GCAGC                                                    15

(2) INFORMATION FOR SEQ ID NO: 325:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 325:

GCUGCCUCGG UGGGG                                                    15

(2) INFORMATION FOR SEQ ID NO: 326:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 326:

```
AUGAGAUCUU CCUAC                                                  15

(2) INFORMATION FOR SEQ ID NO: 327:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 327:

GAGAUCUUCC UACUG                                                  15

(2) INFORMATION FOR SEQ ID NO: 328:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 328:

AGAUCUUCCU ACUGU                                                  15

(2) INFORMATION FOR SEQ ID NO: 329:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 329:

UCUUCCUACU GUGUG                                                  15

(2) INFORMATION FOR SEQ ID NO: 330:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 330:

AGGACAUUGA GGUGU                                                  15

(2) INFORMATION FOR SEQ ID NO: 331:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 331:

GAGGUGUAUU UCACG                                                  15

(2) INFORMATION FOR SEQ ID NO: 332:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 332:

GGUGUAUUUC ACGGG                                                  15
```

(2) INFORMATION FOR SEQ ID NO: 333:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 333:

GUGUAUUUCA CGGGA                                15

(2) INFORMATION FOR SEQ ID NO: 334:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 334:

UGUAUUUCAC GGGAC                                15

(2) INFORMATION FOR SEQ ID NO: 335:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 335:

CGAGGCUCCU UUUCG                                15

(2) INFORMATION FOR SEQ ID NO: 336:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 336:

GAUGAGUUUC CCACC                                15

(2) INFORMATION FOR SEQ ID NO: 337:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 337:

AUGAGUUUCC CACCA                                15

(2) INFORMATION FOR SEQ ID NO: 338:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 338:

UGAGUUUCCC ACCAU                                15

(2) INFORMATION FOR SEQ ID NO: 339:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 339:

AUGGUGUUUC CUUCU                                                    15

(2) INFORMATION FOR SEQ ID NO: 340:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 340:

UGGUGUUUCC UUCUG                                                    15

(2) INFORMATION FOR SEQ ID NO: 341:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 341:

GGUGUUUCCU UCUGG                                                    15

(2) INFORMATION FOR SEQ ID NO: 342:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 342:

GUUUCCUUCU GGGCA                                                    15

(2) INFORMATION FOR SEQ ID NO: 343:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 343:

UUUCCUUCUG GGCAG                                                    15

(2) INFORMATION FOR SEQ ID NO: 344:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 344:

GGCAGAUCAG CCAGG                                                    15

(2) INFORMATION FOR SEQ ID NO: 345:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 345:

CAGGCCUCGG CCUUG                                                  15

(2) INFORMATION FOR SEQ ID NO: 346:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 346:

UCGGCCUUGG CCCCG                                                  15

(2) INFORMATION FOR SEQ ID NO: 347:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 347:

GGCCCCUCCC CAAGU                                                  15

(2) INFORMATION FOR SEQ ID NO: 348:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 348:

CCCAAGUCCU GCCCC                                                  15

(2) INFORMATION FOR SEQ ID NO: 349:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 349:

CCAGGCUCCA GCCCC                                                  15

(2) INFORMATION FOR SEQ ID NO: 350:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 350:

CCCUGCUCCA GCCAU                                                  15

(2) INFORMATION FOR SEQ ID NO: 351:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 351:

CCAUGGUAUC AGCUC                                                          15

(2) INFORMATION FOR SEQ ID NO: 352:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 352:

AUGGUAUCAG CUCUG                                                          15

(2) INFORMATION FOR SEQ ID NO: 353:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 353:

AUCAGCUCUG GCCCA                                                          15

(2) INFORMATION FOR SEQ ID NO: 354:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 354:

CCCCUGUCCC AGUCC                                                          15

(2) INFORMATION FOR SEQ ID NO: 355:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 355:

UCCCAGUCCU AGCCC                                                          15

(2) INFORMATION FOR SEQ ID NO: 356:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 356:

CAGUCCUAGC CCCAG                                                          15

(2) INFORMATION FOR SEQ ID NO: 357:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 357:

AGGCCCUCCU CAGGC                                                            15

(2) INFORMATION FOR SEQ ID NO: 358:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 358:

CCCUCCUCAG GCUGU                                                            15

(2) INFORMATION FOR SEQ ID NO: 359:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 359:

ACGCUGUCAG AGGCC                                                            15

(2) INFORMATION FOR SEQ ID NO: 360:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 360:

CUGCAGUUUG AUGAU                                                            15

(2) INFORMATION FOR SEQ ID NO: 361:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 361:

UGCAGUUUGA UGAUG                                                            15

(2) INFORMATION FOR SEQ ID NO: 362:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 362:

GGGGCCUUGC UUGGC                                                            15

(2) INFORMATION FOR SEQ ID NO: 363:

(i) SEQUENCE CHARACTERISTICS:

```
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 363:

CCUUGCUUGG CAACA                                                          15

(2) INFORMATION FOR SEQ ID NO: 364:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 364:

GCUGUGUUCA CAGAC                                                          15

(2) INFORMATION FOR SEQ ID NO: 365:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 365:

CUGUGUUCAC AGACC                                                          15

(2) INFORMATION FOR SEQ ID NO: 366:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 366:

CUGGCAUCCG UCGAC                                                          15

(2) INFORMATION FOR SEQ ID NO: 367:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 367:

CAUCCGUCGA CAACU                                                          15

(2) INFORMATION FOR SEQ ID NO: 368:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 368:

GACAACUCCG AGUUU                                                          15

(2) INFORMATION FOR SEQ ID NO: 369:

(i) SEQUENCE CHARACTERISTICS:
        (A) LENGTH: 15 base pairs
```

(B) TYPE: nucleic acid
            (C) STRANDEDNESS: single
            (D) TOPOLOGY: linear (xi) SEQUENCE DESCRIPTION: SEQ ID NO: 369:

UCCGAGUUUC AGCAG                                                15

(2) INFORMATION FOR SEQ ID NO: 370:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 370:

CCGAGUUUCA GCAGC                                                15

(2) INFORMATION FOR SEQ ID NO: 371:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 371:

CGAGUUUCAG CAGCU                                                15

(2) INFORMATION FOR SEQ ID NO: 372:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 372:

AGGGCAUACC UGUGG                                                15

(2) INFORMATION FOR SEQ ID NO: 373:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 373:

AUGGAGUACC CUGAG                                                15

(2) INFORMATION FOR SEQ ID NO: 374:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 374:

UGAGGCUAUA ACUCG                                                15

(2) INFORMATION FOR SEQ ID NO: 375:

(i) SEQUENCE CHARACTERISTICS:
            (A) LENGTH: 15 base pairs
            (B) TYPE: nucleic acid

```
          (C) STRANDEDNESS: single
          (D) TOPOLOGY: linear (xi) SEQUENCE DESCRIPTION: SEQ ID NO: 375:

AGGCUAUAAC UCGCC                                                    15

(2) INFORMATION FOR SEQ ID NO: 376:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (xi) SEQUENCE DESCRIPTION: SEQ ID NO: 376:

UAUAACUCGC CUAGU                                                    15

(2) INFORMATION FOR SEQ ID NO: 377:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (xi) SEQUENCE DESCRIPTION: SEQ ID NO: 377:

CUCGCCUAGU GACAG                                                    15

(2) INFORMATION FOR SEQ ID NO: 378:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (xi) SEQUENCE DESCRIPTION: SEQ ID NO: 378:

CCCAGCUCCU GCUCC                                                    15

(2) INFORMATION FOR SEQ ID NO: 379:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (xi) SEQUENCE DESCRIPTION: SEQ ID NO: 379:

UCCUGCUCCA CUGGG                                                    15

(2) INFORMATION FOR SEQ ID NO: 380:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (xi) SEQUENCE DESCRIPTION: SEQ ID NO: 380:

CGGGGCUCCC CAAUG                                                    15

(2) INFORMATION FOR SEQ ID NO: 381:

(i) SEQUENCE CHARACTERISTICS:
          (A) LENGTH: 15 base pairs
          (B) TYPE: nucleic acid
          (C) STRANDEDNESS: single
```

(D) TOPOLOGY: linear (xi) SEQUENCE DESCRIPTION: SEQ ID NO: 381:

AUGGCCUCCU UUCAG                                                    15

(2) INFORMATION FOR SEQ ID NO: 382:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 382:

GCCUCCUUUC AGGAG                                                    15

(2) INFORMATION FOR SEQ ID NO: 383:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 383:

CCUCCUUUCA GGAGA                                                    15

(2) INFORMATION FOR SEQ ID NO: 384:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO: 384:

CUCCUUUCAG GAGAU                                                    15

(2) INFORMATION FOR SEQ ID NO: 385:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 385:

UCCUGUGCUG AUGAGGCCGA AAGGCCGAAA GCCAUU                              36

(2) INFORMATION FOR SEQ ID NO: 386:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 386:

CACCACGCUG AUGAGGCCGA AAGGCCGAAA GGAGCU                              36

(2) INFORMATION FOR SEQ ID NO: 387:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 387:

UGUCCGCCUG AUGAGGCCGA AAGGCCGAAA UGGAGG                     36

(2) INFORMATION FOR SEQ ID NO: 388:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 388:

GAGGGACUG AUGAGGCCGA AAGGCCGAAA CAGAUC                      36

(2) INFORMATION FOR SEQ ID NO: 389:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 389:

UGAGGGCUG AUGAGGCCGA AAGGCCGAAA ACAGAU                      36

(2) INFORMATION FOR SEQ ID NO: 390:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 390:

GAAAGAUCUG AUGAGGCCGA AAGGCCGAAA GGGGAA                     36

(2) INFORMATION FOR SEQ ID NO: 391:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 391:

AGGGAAACUG AUGAGGCCGA AAGGCCGAAA UGAGGG                     36

(2) INFORMATION FOR SEQ ID NO: 392:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 392:

UGAGGGACUG AUGAGGCCGA AAGGCCGAAA GAUGAG                     36

(2) INFORMATION FOR SEQ ID NO: 393:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 393:

CUGAGGGCUG AUGAGGCCGA AAGGCCGAAA AGAUGA        36

(2) INFORMATION FOR SEQ ID NO: 394:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 394:

AGGCCCACUG AUGAGGCCGA AAGGCCGAAA AGCCUG        36

(2) INFORMATION FOR SEQ ID NO: 395:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 395:

CUCCACACUG AUGAGGCCGA AAGGCCGAAA AGGCCC        36

(2) INFORMATION FOR SEQ ID NO: 396:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 396:

GUUCGAUCUG AUGAGGCCGA AAGGCCGAAA UCUCCA        36

(2) INFORMATION FOR SEQ ID NO: 397:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 397:

GCUGUUCCUG AUGAGGCCGA AAGGCCGAAA UGAUCU        36

(2) INFORMATION FOR SEQ ID NO: 398:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 398:

AUAGCGGCUG AUGAGGCCGA AAGGCCGAAA UCGCAU        36

(2) INFORMATION FOR SEQ ID NO: 399:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 399:

UAUAGCGCUG AUGAGGCCGA AAGGCCGAAA AUCGCA 36

(2) INFORMATION FOR SEQ ID NO: 400:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO: 400:

GCAUUUACUG AUGAGGCCGA AAGGCCGAAA GCGGAA 36

(2) INFORMATION FOR SEQ ID NO: 401:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO: 401:

GCCCGCUCUG AUGAGGCCGA AAGGCCGAAA GCGCCC 36

(2) INFORMATION FOR SEQ ID NO: 402:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO: 402:

CGCCAGGCUG AUGAGGCCGA AAGGCCGAAA UACUGC 36

(2) INFORMATION FOR SEQ ID NO: 403:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO: 403:

UUGGUGGCUG AUGAGGCCGA AAGGCCGAAA UCUGUG 36

(2) INFORMATION FOR SEQ ID NO: 404:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO: 404:

UGAUCUUCUG AUGAGGCCGA AAGGCCGAAA UGGUGG 36

(2) INFORMATION FOR SEQ ID NO: 405:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO: 405:

```
AGCCAUUCUG AUGAGGCCGA AAGGCCGAAA UCUUGA                                    36

(2) INFORMATION FOR SEQ ID NO: 406:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 406:

UCCUGUGCUG AUGAGGCCGA AAGGCCGAAA GCCAUU                                    36

(2) INFORMATION FOR SEQ ID NO: 407:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 407:

CCAGGGACUG AUGAGGCCGA AAGGCCGAAA UUCGAA                                    36

(2) INFORMATION FOR SEQ ID NO: 408:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 408:

GACCAGGCUG AUGAGGCCGA AAGGCCGAAA GAUUCG                                    36

(2) INFORMATION FOR SEQ ID NO: 409:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 409:

CCUUGGUCUG AUGAGGCCGA AAGGCCGAAA CCAGGG                                    36

(2) INFORMATION FOR SEQ ID NO: 410:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 410:

UCAGGAGCUG AUGAGGCCGA AAGGCCGAAA GGGGCC                                    36

(2) INFORMATION FOR SEQ ID NO: 411:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 411:

GGCCGGUCUG AUGAGGCCGA AAGGCCGAAA GGUGGA                                    36
```

(2) INFORMATION FOR SEQ ID NO: 412:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 412:

UGUGGAUCUG AUGAGGCCGA AAGGCCGAAA GGCCGG        36

(2) INFORMATION FOR SEQ ID NO: 413:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 413:

UCCCCACCUG AUGAGGCCGA AAGGCCGAAA GUUCAU        36

(2) INFORMATION FOR SEQ ID NO: 414:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 414:

GCUGUUCCUG AUGAGGCCGA AAGGCCGAAA UGAUCU        36

(2) INFORMATION FOR SEQ ID NO: 415:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 415:

CUCAUAGCUG AUGAGGCCGA AAGGCCGAAA GCCAUC        36

(2) INFORMATION FOR SEQ ID NO: 416:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 416:

CUCCGGACUG AUGAGGCCGA AAGGCCGAAA GACCAU        36

(2) INFORMATION FOR SEQ ID NO: 417:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 417:

AGCCUCACUG AUGAGGCCGA AAGGCCGAAA GUAGCC        36

(2) INFORMATION FOR SEQ ID NO: 418:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 418:

CUGGGCACUG AUGAGGCCGA AAGGCCGAAA GGUCAG                      36

(2) INFORMATION FOR SEQ ID NO: 419:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 419:

AGCUAUGCUG AUGAGGCCGA AAGGCCGAAA UACUGC                      36

(2) INFORMATION FOR SEQ ID NO: 420:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 420:

CUAUGGACUG AUGAGGCCGA AAGGCCGAAA CUGCGG                      36

(2) INFORMATION FOR SEQ ID NO: 421:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 421:

GUUCUGGCUG AUGAGGCCGA AAGGCCGAAA GCUAUG                      36

(2) INFORMATION FOR SEQ ID NO: 422:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 422:

GGUUCUGCUG AUGAGGCCGA AAGGCCGAAA AGCUAU                      36

(2) INFORMATION FOR SEQ ID NO: 423:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 423:

CACACUGCUG AUGAGGCCGA AAGGCCGAAA UCCCCA                      36

(2) INFORMATION FOR SEQ ID NO: 424:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 424:

CGAACAGCUG AUGAGGCCGA AAGGCCGAAA GCCUGG    36

(2) INFORMATION FOR SEQ ID NO: 425:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 425:

GCUGGCUCUG AUGAGGCCGA AAGGCCGAAA UGGCUU    36

(2) INFORMATION FOR SEQ ID NO: 426:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 426:

CUGAUCUCUG AUGAGGCCGA AAGGCCGAAA CUCAAA    36

(2) INFORMATION FOR SEQ ID NO: 427:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 427:

UGGUCUGCUG AUGAGGCCGA AAGGCCGAAA UUCGCU    36

(2) INFORMATION FOR SEQ ID NO: 428:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 428:

AACGUGACUG AUGAGGCCGA AAGGCCGAAA GGGGUU    36

(2) INFORMATION FOR SEQ ID NO: 429:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 429:

GAACGUGCUG AUGAGGCCGA AAGGCCGAAA AGGGGU    36

(2) INFORMATION FOR SEQ ID NO: 430:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 430:

CUAUAGGCUG AUGAGGCCGA AAGGCCGAAA CGUGAA                                    36

(2) INFORMATION FOR SEQ ID NO: 431:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 431:

UCUAUAGCUG AUGAGGCCGA AAGGCCGAAA ACGUGA                                    36

(2) INFORMATION FOR SEQ ID NO: 432:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 432:

UCCUCUACUG AUGAGGCCGA AAGGCCGAAA GGAACG                                    36

(2) INFORMATION FOR SEQ ID NO: 433:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 433:

GCUCCUCCUG AUGAGGCCGA AAGGCCGAAA UAGGAA                                    36

(2) INFORMATION FOR SEQ ID NO: 434:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 434:

CAAGUCACUG AUGAGGCCGA AAGGCCGAAA GUCCCC                                    36

(2) INFORMATION FOR SEQ ID NO: 435:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 435:

GGAAGCACUG AUGAGGCCGA AAGGCCGAAA GGCGCA                                    36

(2) INFORMATION FOR SEQ ID NO: 436:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 436:

CACCUGGCUG AUGAGGCCGA AAGGCCGAAA GCAGAG                                  36

(2) INFORMATION FOR SEQ ID NO: 437:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 437:

UCACCUGCUG AUGAGGCCGA AAGGCCGAAA AGCAGA                                  36

(2) INFORMATION FOR SEQ ID NO: 438:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 438:

GCUGGCUCUG AUGAGGCCGA AAGGCCGAAA UGGCUU                                  36

(2) INFORMATION FOR SEQ ID NO: 439:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 439:

UCAGGAGCUG AUGAGGCCGA AAGGCCGAAA GGGGCC                                  36

(2) INFORMATION FOR SEQ ID NO: 440:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 440:

GUGAGAGCUG AUGAGGCCGA AAGGCCGAAA CAGGGG                                  36

(2) INFORMATION FOR SEQ ID NO: 441:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 441:

GAUGUGACUG AUGAGGCCGA AAGGCCGAAA GGACAG                                  36

(2) INFORMATION FOR SEQ ID NO: 442:

(i) SEQUENCE CHARACTERISTICS:

(A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 442:

GGCUGAGCUG AUGAGGCCGA AAGGCCGAAA AGGGAC          36

(2) INFORMATION FOR SEQ ID NO: 443:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 443:

CAUGGCUCUG AUGAGGCCGA AAGGCCGAAA GGAAGG          36

(2) INFORMATION FOR SEQ ID NO: 444:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 444:

GAGAUGGCUG AUGAGGCCGA AAGGCCGAAA GCAGGA          36

(2) INFORMATION FOR SEQ ID NO: 445:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 445:

UAUCAAACUG AUGAGGCCGA AAGGCCGAAA UCGGAU          36

(2) INFORMATION FOR SEQ ID NO: 446:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 446:

GUUAUCACUG AUGAGGCCGA AAGGCCGAAA AAUCGG          36

(2) INFORMATION FOR SEQ ID NO: 447:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 447:

GGUUAUCCUG AUGAGGCCGA AAGGCCGAAA AAAUCG          36

(2) INFORMATION FOR SEQ ID NO: 448:

(i) SEQUENCE CHARACTERISTICS:
        (A) LENGTH: 36 base pairs (B) TYPE: nucleic acid
        (C) STRANDEDNESS: single
        (D) TOPOLOGY: linear (xi) SEQUENCE DESCRIPTION: SEQ ID NO: 448:

GGAACACCUG AUGAGGCCGA AAGGCCGAAA UGGCCA                         36

(2) INFORMATION FOR SEQ ID NO: 449:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 449:

AGAUCUUCUG AUGAGGCCGA AAGGCCGAAA GCUCGG                         36

(2) INFORMATION FOR SEQ ID NO: 450:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 450:

CUCGGCACUG AUGAGGCCGA AAGGCCGAAA UCUUGA                         36

(2) INFORMATION FOR SEQ ID NO: 451:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 451:

GCUCCCACUG AUGAGGCCGA AAGGCCGAAA GUUCCG                         36

(2) INFORMATION FOR SEQ ID NO: 452:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 452:

CCCCACCCUG AUGAGGCCGA AAGGCCGAAA GGCAGC                         36

(2) INFORMATION FOR SEQ ID NO: 453:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 453:

GCAAGAACUG AUGAGGCCGA AAGGCCGAAA UCUCAU                         36

(2) INFORMATION FOR SEQ ID NO: 454:

(i) SEQUENCE CHARACTERISTICS:
        (A) LENGTH: 36 base pairs
        (B) TYPE: nucleic acid (C) STRANDEDNESS: single
        (D) TOPOLOGY: linear (xi) SEQUENCE DESCRIPTION: SEQ ID NO: 454:

CAGCAAGCUG AUGAGGCCGA AAGGCCGAAA GAUCUC                                      36

(2) INFORMATION FOR SEQ ID NO: 455:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 455:

ACAGCAACUG AUGAGGCCGA AAGGCCGAAA AGAUCU                                      36

(2) INFORMATION FOR SEQ ID NO: 456:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 456:

CGCAAUGCUG AUGAGGCCGA AAGGCCGAAA GGAGAA                                      36

(2) INFORMATION FOR SEQ ID NO: 457:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 457:

ACACCUCCUG AUGAGGCCGA AAGGCCGAAA UGUCUU                                      36

(2) INFORMATION FOR SEQ ID NO: 458:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 458:

CGUGAAACUG AUGAGGCCGA AAGGCCGAAA CACCUC                                      36

(2) INFORMATION FOR SEQ ID NO: 459:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 459:

CCCGUGACUG AUGAGGCCGA AAGGCCGAAA UACACC                                      36

(2) INFORMATION FOR SEQ ID NO: 460:

(i) SEQUENCE CHARACTERISTICS:
        (A) LENGTH: 36 base pairs
        (B) TYPE: nucleic acid
        (C) STRANDEDNESS: single (D) TOPOLOGY: linear (xi) SEQUENCE DESCRIPTION: SEQ ID NO: 460:

UCCCGUGCUG AUGAGGCCGA AAGGCCGAAA AUACAC                         36

(2) INFORMATION FOR SEQ ID NO: 461:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 461:

GUCCCGUCUG AUGAGGCCGA AAGGCCGAAA AAUACA                         36

(2) INFORMATION FOR SEQ ID NO: 462:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 462:

AGAAAAGCUG AUGAGGCCGA AAGGCCGAAA GCCUCG                         36

(2) INFORMATION FOR SEQ ID NO: 463:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 463:

UUGAGAACUG AUGAGGCCGA AAGGCCGAAA GGAGCC                         36

(2) INFORMATION FOR SEQ ID NO: 464:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 464:

CUUGAGACUG AUGAGGCCGA AAGGCCGAAA AGGAGC                         36

(2) INFORMATION FOR SEQ ID NO: 465:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 465:

GCUUGAGCUG AUGAGGCCGA AAGGCCGAAA AAGGAG                         36

(2) INFORMATION FOR SEQ ID NO: 466:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 466:

AGCUUGACUG AUGAGGCCGA AAGGCCGAAA AAAGGA                                    36

(2) INFORMATION FOR SEQ ID NO: 467:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 467:

GGAACACCUG AUGAGGCCGA AAGGCCGAAA UGGCCA                                    36

(2) INFORMATION FOR SEQ ID NO: 468:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 468:

AGUCCGGCUG AUGAGGCCGA AAGGCCGAAA CACAAU                                    36

(2) INFORMATION FOR SEQ ID NO: 469:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 469:

GAGUCCGCUG AUGAGGCCGA AAGGCCGAAA ACACAA                                    36

(2) INFORMATION FOR SEQ ID NO: 470:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 470:

GCGUACGCUG AUGAGGCCGA AAGGCCGAAA GGAGUC                                    36

(2) INFORMATION FOR SEQ ID NO: 471:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 471:

GUCGGCGCUG AUGAGGCCGA AAGGCCGAAA CGGAGG                                    36

(2) INFORMATION FOR SEQ ID NO: 472:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 472:

CGAACAGCUG AUGAGGCCGA AAGGCCGAAA GCCUGG                              36

(2) INFORMATION FOR SEQ ID NO: 473:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 473:

GCAUGGACUG AUGAGGCCGA AAGGCCGAAA CUCGAA                              36

(2) INFORMATION FOR SEQ ID NO: 474:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 474:

CUGCAUGCUG AUGAGGCCGA AAGGCCGAAA GACUCG                              36

(2) INFORMATION FOR SEQ ID NO: 475:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 475:

CGAUCAGCUG AUGAGGCCGA AAGGCCGAAA GGCCGC                              36

(2) INFORMATION FOR SEQ ID NO: 476:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 476:

GCGAUCACUG AUGAGGCCGA AAGGCCGAAA AGGCCG                              36

(2) INFORMATION FOR SEQ ID NO: 477:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 477:

GCUCACUCUG AUGAGGCCGA AAGGCCGAAA GCUCGC                              36

(2) INFORMATION FOR SEQ ID NO: 478:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 478:

GUACUGGCUG AUGAGGCCGA AAGGCCGAAA CUCCAU        36

(2) INFORMATION FOR SEQ ID NO: 479:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 479:

AGUACUGCUG AUGAGGCCGA AAGGCCGAAA ACUCCA        36

(2) INFORMATION FOR SEQ ID NO: 480:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 480:

UGGCAAGCUG AUGAGGCCGA AAGGCCGAAA CUGGAA        36

(2) INFORMATION FOR SEQ ID NO: 481:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 481:

UCAUGUGCUG AUGAGGCCGA AAGGCCGAAA UGAGGC        36

(2) INFORMATION FOR SEQ ID NO: 482:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 482:

CGGUGGCCUG AUGAGGCCGA AAGGCCGAAA UCAUCU        36

(2) INFORMATION FOR SEQ ID NO: 483:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 483:

GUCUGGCCUG AUGAGGCCGA AAGGCCGAAA GUACUG        36

(2) INFORMATION FOR SEQ ID NO: 484:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 484:

```
UCUCUUCCUG AUGAGGCCGA AAGGCCGAAA UCCGGU                                   36
```

(2) INFORMATION FOR SEQ ID NO: 485:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 485:

```
ACUCUUGCUG AUGAGGCCGA AAGGCCGAAA GGUCUC                                   36
```

(2) INFORMATION FOR SEQ ID NO: 486:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 486:

```
GGUCUCACUG AUGAGGCCGA AAGGCCGAAA GGUCCU                                   36
```

(2) INFORMATION FOR SEQ ID NO: 487:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 487:

```
ACUCUUGCUG AUGAGGCCGA AAGGCCGAAA GGUCUC                                   36
```

(2) INFORMATION FOR SEQ ID NO: 488:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 488:

```
UACUCUUCUG AUGAGGCCGA AAGGCCGAAA AGGUCU                                   36
```

(2) INFORMATION FOR SEQ ID NO: 489:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 489:

```
UCUUCAUCUG AUGAGGCCGA AAGGCCGAAA UACUCU                                   36
```

(2) INFORMATION FOR SEQ ID NO: 490:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 490:

```
UUGAAAGCUG AUGAGGCCGA AAGGCCGAAA CUCUUC                                   36
```

(2) INFORMATION FOR SEQ ID NO: 491:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 491:

CCAUUGACUG AUGAGGCCGA AAGGCCGAAA GGACUC                                36

(2) INFORMATION FOR SEQ ID NO: 492:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 492:

UCCAUUGCUG AUGAGGCCGA AAGGCCGAAA AGGACU                                36

(2) INFORMATION FOR SEQ ID NO: 493:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 493:

GUCCAUUCUG AUGAGGCCGA AAGGCCGAAA AAGGAC                                36

(2) INFORMATION FOR SEQ ID NO: 494:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 494:

CGGGUUGCUG AUGAGGCCGA AAGGCCGAAA GGCCGG                                36

(2) INFORMATION FOR SEQ ID NO: 495:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 495:

UUGGAUCCUG AUGAGGCCGA AAGGCCGAAA GGUGUA                                36

(2) INFORMATION FOR SEQ ID NO: 496:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 496:

GCACAGCCUG AUGAGGCCGA AAGGCCGAAA UACGCC                                36

(2) INFORMATION FOR SEQ ID NO: 497:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 497:

UUUCGGGCUG AUGAGGCCGA AAGGCCGAAA GGCACA                    36

(2) INFORMATION FOR SEQ ID NO: 498:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 498:

ACUUCGGCUG AUGAGGCCGA AAGGCCGAAA AGGCUU                    36

(2) INFORMATION FOR SEQ ID NO: 499:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 499:

AGAAGUUCUG AUGAGGCCGA AAGGCCGAAA GUUUCG                    36

(2) INFORMATION FOR SEQ ID NO: 500:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 500:

GGGACAGCUG AUGAGGCCGA AAGGCCGAAA GUUGAG                    36

(2) INFORMATION FOR SEQ ID NO: 501:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 501:

GGGGACACUG AUGAGGCCGA AAGGCCGAAA AGUUGA                    36

(2) INFORMATION FOR SEQ ID NO: 502:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 502:

GCUUGGGCUG AUGAGGCCGA AAGGCCGAAA CAGAAG                    36

(2) INFORMATION FOR SEQ ID NO: 503:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 503:

GAAGGUGCUG AUGAGGCCGA AAGGCCGAAA GGGCUG                          36

(2) INFORMATION FOR SEQ ID NO: 504:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 504:

GUAAGGCCUG AUGAGGCCGA AAGGCCGAAA UAUGGC                          36

(2) INFORMATION FOR SEQ ID NO: 505:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 505:

UGGUGCUCUG AUGAGGCCGA AAGGCCGAAA GGGAUG                          36

(2) INFORMATION FOR SEQ ID NO: 506:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 506:

AUGCUGGCUG AUGAGGCCGA AAGGCCGAAA AGGUGU                          36

(2) INFORMATION FOR SEQ ID NO: 507:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 507:

GAAGCUGCUG AUGAGGCCGA AAGGCCGAAA GAUGGA                          36

(2) INFORMATION FOR SEQ ID NO: 508:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 508:

GCGCGCUCUG AUGAGGCCGA AAGGCCGAAA AGUAAA                          36

(2) INFORMATION FOR SEQ ID NO: 509:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 509:

GCUGAGGCUG AUGAGGCCGA AAGGCCGAAA UGCUGG                                      36

(2) INFORMATION FOR SEQ ID NO: 510:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 510:

CAAAGUUCUG AUGAGGCCGA AAGGCCGAAA UGGUGC                                      36

(2) INFORMATION FOR SEQ ID NO: 511:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 511:

CUCAUCACUG AUGAGGCCGA AAGGCCGAAA GUUGAU                                      36

(2) INFORMATION FOR SEQ ID NO: 512:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 512:

GGGGGAACUG AUGAGGCCGA AAGGCCGAAA CUCAUC                                      36

(2) INFORMATION FOR SEQ ID NO: 513:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 513:

UGGGGGACUG AUGAGGCCGA AAGGCCGAAA ACUCAU                                      36

(2) INFORMATION FOR SEQ ID NO: 514:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO: 514:

AUGGGGGCUG AUGAGGCCGA AAGGCCGAAA AACUCA                                      36

(2) INFORMATION FOR SEQ ID NO: 515:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 515:

UGAUGGUCUG AUGAGGCCGA AAGGCCGAAA CAGCAU                36

(2) INFORMATION FOR SEQ ID NO: 516:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 516:

CUGAUGGCUG AUGAGGCCGA AAGGCCGAAA ACAGCA                36

(2) INFORMATION FOR SEQ ID NO: 517:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 517:

UCAGGAGCUG AUGAGGCCGA AAGGCCGAAA GGGGCC                36

(2) INFORMATION FOR SEQ ID NO: 518:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 518:

GGCUGAGCUG AUGAGGCCGA AAGGCCGAAA AGGGAC                36

(2) INFORMATION FOR SEQ ID NO: 519:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 519:

CUGCCCUCUG AUGAGGCCGA AAGGCCGAAA UGGUAA                36

(2) INFORMATION FOR SEQ ID NO: 520:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 520:

UCAGACUCUG AUGAGGCCGA AAGGCCGAAA ACUCCC                36

(2) INFORMATION FOR SEQ ID NO: 521:

(i) SEQUENCE CHARACTERISTICS:

(A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 521:

GAAGGUGCUG AUGAGGCCGA AAGGCCGAAA GGGCUG                    36

(2) INFORMATION FOR SEQ ID NO: 522:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 522:

CGGUGCUCUG AUGAGGCCGA AAGGCCGAAA GGCCAG                    36

(2) INFORMATION FOR SEQ ID NO: 523:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 523:

GCUGAGGCUG AUGAGGCCGA AAGGCCGAAA GGGACC                    36

(2) INFORMATION FOR SEQ ID NO: 524:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 524:

GGGGCAGCUG AUGAGGCCGA AAGGCCGAAA GCUGGG                    36

(2) INFORMATION FOR SEQ ID NO: 525:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 525:

GAGCCUGCUG AUGAGGCCGA AAGGCCGAAA GGCUGG                    36

(2) INFORMATION FOR SEQ ID NO: 526:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 526:

GGGGCAGCUG AUGAGGCCGA AAGGCCGAAA GCUGGG                    36

(2) INFORMATION FOR SEQ ID NO: 527:

(i) SEQUENCE CHARACTERISTICS:
        (A) LENGTH: 36 base pairs (B) TYPE: nucleic acid
        (C) STRANDEDNESS: single
        (D) TOPOLOGY: linear (xi) SEQUENCE DESCRIPTION: SEQ ID NO: 527:

AGGAAGGCUG AUGAGGCCGA AAGGCCGAAA CCAUGG                              36

(2) INFORMATION FOR SEQ ID NO: 528:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 528:

CGCAGCUCUG AUGAGGCCGA AAGGCCGAAA GCCCAC                              36

(2) INFORMATION FOR SEQ ID NO: 529:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 529:

UGGGGGACUG AUGAGGCCGA AAGGCCGAAA ACUCAU                              36

(2) INFORMATION FOR SEQ ID NO: 530:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 530:

AGACUCGCUG AUGAGGCCGA AAGGCCGAAA CAGGAG                              36

(2) INFORMATION FOR SEQ ID NO: 531:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 531:

GGGUUAGCUG AUGAGGCCGA AAGGCCGAAA CUGGGG                              36

(2) INFORMATION FOR SEQ ID NO: 532:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 532:

CCGGGGUCUG AUGAGGCCGA AAGGCCGAAA GAACUG                              36

(2) INFORMATION FOR SEQ ID NO: 533:

(i) SEQUENCE CHARACTERISTICS:
        (A) LENGTH: 36 base pairs
        (B) TYPE: nucleic acid

```
        (C) STRANDEDNESS: single
        (D) TOPOLOGY: linear (xi) SEQUENCE DESCRIPTION: SEQ ID NO: 533:

GACUGGGCUG AUGAGGCCGA AAGGCCGAAA GGACCC                                    36

(2) INFORMATION FOR SEQ ID NO: 534:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 534:

UCAGCUUCUG AUGAGGCCGA AAGGCCGAAA GAAAAG                                    36

(2) INFORMATION FOR SEQ ID NO: 535:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 535:

GGCUUCCCUG AUGAGGCCGA AAGGCCGAAA CAGCGU                                    36

(2) INFORMATION FOR SEQ ID NO: 536:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 536:

AGCAUCACUG AUGAGGCCGA AAGGCCGAAA CUGCAG                                    36

(2) INFORMATION FOR SEQ ID NO: 537:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 537:

CAGCAUCCUG AUGAGGCCGA AAGGCCGAAA ACUGCA                                    36

(2) INFORMATION FOR SEQ ID NO: 538:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 538:

GCCAAGCCUG AUGAGGCCGA AAGGCCGAAA GGCCCC                                    36

(2) INFORMATION FOR SEQ ID NO: 539:

(i) SEQUENCE CHARACTERISTICS:
        (A) LENGTH: 36 base pairs
        (B) TYPE: nucleic acid
        (C) STRANDEDNESS: single
```

(D) TOPOLOGY: linear (xi) SEQUENCE DESCRIPTION: SEQ ID NO: 539:

UGUUGCCCUG AUGAGGCCGA AAGGCCGAAA GCAAGG                              36

(2) INFORMATION FOR SEQ ID NO: 540:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 540:

GUCUGUGCUG AUGAGGCCGA AAGGCCGAAA CACUCC                              36

(2) INFORMATION FOR SEQ ID NO: 541:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 541:

GGUCUGUCUG AUGAGGCCGA AAGGCCGAAA ACACUC                              36

(2) INFORMATION FOR SEQ ID NO: 542:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 542:

GUCCACACUG AUGAGGCCGA AAGGCCGAAA UGCCAG                              36

(2) INFORMATION FOR SEQ ID NO: 543:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 543:

AGUUCCCCUG AUGAGGCCGA AAGGCCGAAA CCGAAG                              36

(2) INFORMATION FOR SEQ ID NO: 544:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 544:

AAACUCUCUG AUGAGGCCGA AAGGCCGAAA GUUGUC                              36

(2) INFORMATION FOR SEQ ID NO: 545:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 545:

CUGCUGACUG AUGAGGCCGA AAGGCCGAAA CUCUGA                36

(2) INFORMATION FOR SEQ ID NO: 546:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 546:

GCUGCUGCUG AUGAGGCCGA AAGGCCGAAA ACUCUG                36

(2) INFORMATION FOR SEQ ID NO: 547:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 547:

AGCUGCUCUG AUGAGGCCGA AAGGCCGAAA AACUCU                36

(2) INFORMATION FOR SEQ ID NO: 548:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 548:

ACACAGGCUG AUGAGGCCGA AAGGCCGAAA UGCACC                36

(2) INFORMATION FOR SEQ ID NO: 549:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 549:

UUCAGGGCUG AUGAGGCCGA AAGGCCGAAA CUCCAU                36

(2) INFORMATION FOR SEQ ID NO: 550:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 550:

CGAGUUACUG AUGAGGCCGA AAGGCCGAAA GCUUCA                36

(2) INFORMATION FOR SEQ ID NO: 551:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 551:

GGCGAGUCUG AUGAGGCCGA AAGGCCGAAA UAGCUU        36

(2) INFORMATION FOR SEQ ID NO: 552:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 552:

ACCAGGCCUG AUGAGGCCGA AAGGCCGAAA GUUAUA        36

(2) INFORMATION FOR SEQ ID NO: 553:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 553:

CCCUCUCCUG AUGAGGCCGA AAGGCCGAAA GGAGAG        36

(2) INFORMATION FOR SEQ ID NO: 554:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 554:

GGGGCAGCUG AUGAGGCCGA AAGGCCGAAA GCUGGG        36

(2) INFORMATION FOR SEQ ID NO: 555:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 555:

CCUACCGCUG AUGAGGCCGA AAGGCCGAAA GCAGGA        36

(2) INFORMATION FOR SEQ ID NO: 556:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 556:

CAUUGGGCUG AUGAGGCCGA AAGGCCGAAA GCCCCG        36

(2) INFORMATION FOR SEQ ID NO: 557:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 557:

CUGGGCACUG AUGAGGCCGA AAGGCCGAAA GGUCAG 36

(2) INFORMATION FOR SEQ ID NO: 558:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 558:

CACCUGGCUG AUGAGGCCGA AAGGCCGAAA GCAGAG 36

(2) INFORMATION FOR SEQ ID NO: 559:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 559:

UCACCUGCUG AUGAGGCCGA AAGGCCGAAA AGCAGA 36

(2) INFORMATION FOR SEQ ID NO: 560:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 560:

ACCUCCGCUG AUGAGGCCGA AAGGCCGAAA AGCGAG 36

(2) INFORMATION FOR SEQ ID NO: 561:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 561:

GGAGGAGCUG AUGAGGCCGA AAGGCCGAAA GUCUUC 36

(2) INFORMATION FOR SEQ ID NO: 562:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 562:

UGGAGGACUG AUGAGGCCGA AAGGCCGAAA AGUCUU 36

(2) INFORMATION FOR SEQ ID NO: 563:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 563:

AAUGGAGCUG AUGAGGCCGA AAGGCCGAAA GAAGUC                36

(2) INFORMATION FOR SEQ ID NO: 564:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 564:

CGCAAUGCUG AUGAGGCCGA AAGGCCGAAA GGAGAA                36

(2) INFORMATION FOR SEQ ID NO: 565:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 565:

UGUCCGCCUG AUGAGGCCGA AAGGCCGAAA UGGAGG                36

(2) INFORMATION FOR SEQ ID NO: 566:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 566:

AGCAGAGCUG AUGAGGCCGA AAGGCCGAAA GUCCAU                36

(2) INFORMATION FOR SEQ ID NO: 567:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 567:

GAGCAGACUG AUGAGGCCGA AAGGCCGAAA AGUCCA                36

(2) INFORMATION FOR SEQ ID NO: 568:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 568:

AAGAGCACUG AUGAGGCCGA AAGGCCGAAA GAAGUC                36

(2) INFORMATION FOR SEQ ID NO: 569:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 569:

CUGAUCUCUG AUGAGGCCGA AAGGCCGAAA CUCAAA                36

(2) INFORMATION FOR SEQ ID NO: 570:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 570:

AGGAGCUCUG AUGAGGCCGA AAGGCCGAAA UCUGAC                       36

(2) INFORMATION FOR SEQ ID NO: 571:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 571:

ACCUUAGCUG AUGAGGCCGA AAGGCCGAAA GCUGAU                       36

(2) INFORMATION FOR SEQ ID NO: 572:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 572:

AGCACCUCUG AUGAGGCCGA AAGGCCGAAA GGAGCU                       36

(2) INFORMATION FOR SEQ ID NO: 573:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 573:

CUCUUGGCUG AUGAGGCCGA AAGGCCGAAA GCACUG                       36

(2) INFORMATION FOR SEQ ID NO: 574:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 574:

UACAGACCUG AUGAGGCCGA AAGGCCGAAA GCCAUU                       36

(2) INFORMATION FOR SEQ ID NO: 575:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 575:

CACUACACUG AUGAGGCCGA AAGGCCGAAA CGAGCC                       36

(2) INFORMATION FOR SEQ ID NO: 576:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 576:

CGUGCACCUG AUGAGGCCGA AAGGCCGAAA CAGACG                                36

(2) INFORMATION FOR SEQ ID NO: 577:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 577:

GAGGGGCUG AUGAGGCCGA AAGGCCGAAA CAGUUC                                 36

(2) INFORMATION FOR SEQ ID NO: 578:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 578:

UGAGGGGCUG AUGAGGCCGA AAGGCCGAAA ACAGUU                                36

(2) INFORMATION FOR SEQ ID NO: 579:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 579:

GGAAGAUCUG AUGAGGCCGA AAGGCCGAAA GGGGGA                                36

(2) INFORMATION FOR SEQ ID NO: 580:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 580:

CCGGGAACUG AUGAGGCCGA AAGGCCGAAA UGAGGG                                36

(2) INFORMATION FOR SEQ ID NO: 581:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 581:

UGCCGGGCUG AUGAGGCCGA AAGGCCGAAA GAUGAG                                36

(2) INFORMATION FOR SEQ ID NO: 582:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 582:

CUGCCGGCUG AUGAGGCCGA AAGGCCGAAA AGAUGA                          36

(2) INFORMATION FOR SEQ ID NO: 583:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 583:

GGGGCCACUG AUGAGGCCGA AAGGCCGAAA GGCCUG                          36

(2) INFORMATION FOR SEQ ID NO: 584:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 584:

CUCCACACUG AUGAGGCCGA AAGGCCGAAA GGGGCC                          36

(2) INFORMATION FOR SEQ ID NO: 585:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 585:

GCUCAAUCUG AUGAGGCCGA AAGGCCGAAA UCUCCA                          36

(2) INFORMATION FOR SEQ ID NO: 586:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 586:

GCUGCUCCUG AUGAGGCCGA AAGGCCGAAA UGAUCU                          36

(2) INFORMATION FOR SEQ ID NO: 587:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 587:

GUAGCGGCUG AUGAGGCCGA AAGGCCGAAA GCGCAU                          36

(2) INFORMATION FOR SEQ ID NO: 588:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO: 588:

UGUAGCGCUG AUGAGGCCGA AAGGCCGAAA AGCGCA                        36

(2) INFORMATION FOR SEQ ID NO: 589:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 589:

GCACUUGCUG AUGAGGCCGA AAGGCCGAAA GCGGAA                        36

(2) INFORMATION FOR SEQ ID NO: 590:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 590:

GCCCGCGCUG AUGAGGCCGA AAGGCCGAAA GCGCCC                        36

(2) INFORMATION FOR SEQ ID NO: 591:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 591:

CGCCUGGCUG AUGAGGCCGA AAGGCCGAAA UGCUGC                        36

(2) INFORMATION FOR SEQ ID NO: 592:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 592:

UUGGUGGCUG AUGAGGCCGA AAGGCCGAAA UCUGUG                        36

(2) INFORMATION FOR SEQ ID NO: 593:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 593:

UGAUCUUCUG AUGAGGCCGA AAGGCCGAAA UGGUGG                        36

(2) INFORMATION FOR SEQ ID NO: 594:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO: 594:

AGCCAUUCUG AUGAGGCCGA AAGGCCGAAA UCUUGA                              36

(2) INFORMATION FOR SEQ ID NO: 595:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO: 595:

UCCUGUGCUG AUGAGGCCGA AAGGCCGAAA GCCAUU                              36

(2) INFORMATION FOR SEQ ID NO: 596:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO: 596:

CCAGGGACUG AUGAGGCCGA AAGGCCGAAA UGCGCA                              36

(2) INFORMATION FOR SEQ ID NO: 597:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO: 597:

GACCAGGCUG AUGAGGCCGA AAGGCCGAAA GAUGCG                              36

(2) INFORMATION FOR SEQ ID NO: 598:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO: 598:

CCUUGGUCUG AUGAGGCCGA AAGGCCGAAA CCAGGG                              36

(2) INFORMATION FOR SEQ ID NO: 599:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO: 599:

CGGUGAGCUG AUGAGGCCGA AAGGCCGAAA GGGUCC                              36

(2) INFORMATION FOR SEQ ID NO: 600:

(i) SEQUENCE CHARACTERISTICS:

(A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 600:

GGCCGGUCUG AUGAGGCCGA AAGGCCGAAA GGAGGG                    36

(2) INFORMATION FOR SEQ ID NO: 601:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 601:

UGGGGGUCUG AUGAGGCCGA AAGGCCGAAA GGCCGG                    36

(2) INFORMATION FOR SEQ ID NO: 602:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 602:

UUCCUACCUG AUGAGGCCGA AAGGCCGAAA GCUCGU                    36

(2) INFORMATION FOR SEQ ID NO: 603:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 603:

CCUUUCCCUG AUGAGGCCGA AAGGCCGAAA CAAGCU                    36

(2) INFORMATION FOR SEQ ID NO: 604:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 604:

CUCAUAGCUG AUGAGGCCGA AAGGCCGAAA GCCAUC                    36

(2) INFORMATION FOR SEQ ID NO: 605:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 605:

CCUCAUACUG AUGAGGCCGA AAGGCCGAAA AGCCAU                    36

(2) INFORMATION FOR SEQ ID NO: 606:

(i) SEQUENCE CHARACTERISTICS:
        (A) LENGTH: 36 base pairs (B) TYPE: nucleic acid
        (C) STRANDEDNESS: single
        (D) TOPOLOGY: linear (xi) SEQUENCE DESCRIPTION: SEQ ID NO: 606:

AGCCUCACUG AUGAGGCCGA AAGGCCGAAA GAAGCC                                  36

(2) INFORMATION FOR SEQ ID NO: 607:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 607:

CCGGGCACUG AUGAGGCCGA AAGGCCGAAA GCUCAG                                  36

(2) INFORMATION FOR SEQ ID NO: 608:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 608:

AACUGUGCUG AUGAGGCCGA AAGGCCGAAA UGCAGC                                  36

(2) INFORMATION FOR SEQ ID NO: 609:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 609:

UUCUGGACUG AUGAGGCCGA AAGGCCGAAA CUGUGG                                  36

(2) INFORMATION FOR SEQ ID NO: 610:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 610:

GUUCUGGCUG AUGAGGCCGA AAGGCCGAAA ACUGUG                                  36

(2) INFORMATION FOR SEQ ID NO: 611:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 611:

GGUUCUGCUG AUGAGGCCGA AAGGCCGAAA AACUGU                                  36

(2) INFORMATION FOR SEQ ID NO: 612:

(i) SEQUENCE CHARACTERISTICS:
        (A) LENGTH: 36 base pairs
        (B) TYPE: nucleic acid

```
        (C) STRANDEDNESS: single
        (D) TOPOLOGY: linear (xi) SEQUENCE DESCRIPTION: SEQ ID NO: 612:

CACACUGCUG AUGAGGCCGA AAGGCCGAAA UUCCCA                              36

(2) INFORMATION FOR SEQ ID NO: 613:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 613:

UGACUGACUG AUGAGGCCGA AAGGCCGAAA GCCUGC                              36

(2) INFORMATION FOR SEQ ID NO: 614:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 614:

GCUGACUCUG AUGAGGCCGA AAGGCCGAAA UAGCCU                              36

(2) INFORMATION FOR SEQ ID NO: 615:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 615:

AUGCGCUCUG AUGAGGCCGA AAGGCCGAAA CUGAUA                              36

(2) INFORMATION FOR SEQ ID NO: 616:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 616:

UGGUCUGCUG AUGAGGCCGA AAGGCCGAAA UGCGCU                              36

(2) INFORMATION FOR SEQ ID NO: 617:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 617:

AACUUGGCUG AUGAGGCCGA AAGGCCGAAA GGGGUU                              36

(2) INFORMATION FOR SEQ ID NO: 618:

(i) SEQUENCE CHARACTERISTICS:
        (A) LENGTH: 36 base pairs
        (B) TYPE: nucleic acid
        (C) STRANDEDNESS: single
```

(D) TOPOLOGY: linear (xi) SEQUENCE DESCRIPTION: SEQ ID NO: 618:

GAACUUGCUG AUGAGGCCGA AAGGCCGAAA AGGGGU                       36

(2) INFORMATION FOR SEQ ID NO: 619:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 619:

CUAUAGGCUG AUGAGGCCGA AAGGCCGAAA CUUGGA                       36

(2) INFORMATION FOR SEQ ID NO: 620:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 620:

UCUAUAGCUG AUGAGGCCGA AAGGCCGAAA ACUUGG                       36

(2) INFORMATION FOR SEQ ID NO: 621:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 621:

UCUUCUACUG AUGAGGCCGA AAGGCCGAAA GGAACU                       36

(2) INFORMATION FOR SEQ ID NO: 622:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 622:

GCUCUUCCUG AUGAGGCCGA AAGGCCGAAA UAGGAA                       36

(2) INFORMATION FOR SEQ ID NO: 623:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 623:

CAGGUCGCUG AUGAGGCCGA AAGGCCGAAA GUCCCC                       36

(2) INFORMATION FOR SEQ ID NO: 624:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 624:

GGAAGCACUG AUGAGGCCGA AAGGCCGAAA GCCGCA                          36

(2) INFORMATION FOR SEQ ID NO: 625:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 625:

CACCUGGCUG AUGAGGCCGA AAGGCCGAAA GCAGAG                          36

(2) INFORMATION FOR SEQ ID NO: 626:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 626:

UCACCUGCUG AUGAGGCCGA AAGGCCGAAA AGCAGA                          36

(2) INFORMATION FOR SEQ ID NO: 627:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 627:

CCUGCCUCUG AUGAGGCCGA AAGGCCGAAA UGGGUC                          36

(2) INFORMATION FOR SEQ ID NO: 628:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 628:

GCAGGCGCUG AUGAGGCCGA AAGGCCGAAA GGGGCC                          36

(2) INFORMATION FOR SEQ ID NO: 629:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 629:

GAGGAAGCUG AUGAGGCCGA AAGGCCGAAA CAGGCG                          36

(2) INFORMATION FOR SEQ ID NO: 630:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 630:

GAUGAGGCUG AUGAGGCCGA AAGGCCGAAA GGACAG                                           36

(2) INFORMATION FOR SEQ ID NO: 631:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 631:

GGAUGAGCUG AUGAGGCCGA AAGGCCGAAA AGGACA                                           36

(2) INFORMATION FOR SEQ ID NO: 632:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 632:

AUGGGAUCUG AUGAGGCCGA AAGGCCGAAA GGAAGG                                           36

(2) INFORMATION FOR SEQ ID NO: 633:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 633:

AAGAUGGCUG AUGAGGCCGA AAGGCCGAAA UGAGGA                                           36

(2) INFORMATION FOR SEQ ID NO: 634:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 634:

UGUCAAACUG AUGAGGCCGA AAGGCCGAAA UGGGAU                                           36

(2) INFORMATION FOR SEQ ID NO: 635:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 635:

AUUGUCACUG AUGAGGCCGA AAGGCCGAAA GAUGGG                                           36

(2) INFORMATION FOR SEQ ID NO: 636:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 636:

GAUUGUCCUG AUGAGGCCGA AAGGCCGAAA AGAUGG                36

(2) INFORMATION FOR SEQ ID NO: 637:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 637:

GGGGCACCUG AUGAGGCCGA AAGGCCGAAA UUGUCA                36

(2) INFORMATION FOR SEQ ID NO: 638:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 638:

AGAUCUUCUG AUGAGGCCGA AAGGCCGAAA GCUCGG                36

(2) INFORMATION FOR SEQ ID NO: 639:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 639:

CUCGGCACUG AUGAGGCCGA AAGGCCGAAA UCUUGA                36

(2) INFORMATION FOR SEQ ID NO: 640:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 640:

GCUGCCACUG AUGAGGCCGA AAGGCCGAAA GUUUCG                36

(2) INFORMATION FOR SEQ ID NO: 641:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 641:

CCCCACCCUG AUGAGGCCGA AAGGCCGAAA GGCAGC                36

(2) INFORMATION FOR SEQ ID NO: 642:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 642:

GUAGGAACUG AUGAGGCCGA AAGGCCGAAA UCUCAU                              36

(2) INFORMATION FOR SEQ ID NO: 643:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 643:

CAGUAGGCUG AUGAGGCCGA AAGGCCGAAA GAUCUC                              36

(2) INFORMATION FOR SEQ ID NO: 644:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 644:

ACAGUAGCUG AUGAGGCCGA AAGGCCGAAA AGAUCU                              36

(2) INFORMATION FOR SEQ ID NO: 645:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 645:

CACACAGCUG AUGAGGCCGA AAGGCCGAAA GGAAGA                              36

(2) INFORMATION FOR SEQ ID NO: 646:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 646:

ACACCUCCUG AUGAGGCCGA AAGGCCGAAA UGUCCU                              36

(2) INFORMATION FOR SEQ ID NO: 647:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 647:

CGUGAAACUG AUGAGGCCGA AAGGCCGAAA CACCUC                              36

(2) INFORMATION FOR SEQ ID NO: 648:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 648:

CCCGUGACUG AUGAGGCCGA AAGGCCGAAA UACACC                              36

(2) INFORMATION FOR SEQ ID NO: 649:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 649:

UCCCGUGCUG AUGAGGCCGA AAGGCCGAAA AUACAC                        36

(2) INFORMATION FOR SEQ ID NO: 650:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 650:

GUCCCGUCUG AUGAGGCCGA AAGGCCGAAA AAUACA                        36

(2) INFORMATION FOR SEQ ID NO: 651:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 651:

CGAAAAGCUG AUGAGGCCGA AAGGCCGAAA GCCUCG                        36

(2) INFORMATION FOR SEQ ID NO: 652:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 652:

UUGCGAACUG AUGAGGCCGA AAGGCCGAAA GGAGCC                        36

(2) INFORMATION FOR SEQ ID NO: 653:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 653:

CUUGCGACUG AUGAGGCCGA AAGGCCGAAA AGGAGC                        36

(2) INFORMATION FOR SEQ ID NO: 654:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 654:

GCUUGCGCUG AUGAGGCCGA AAGGCCGAAA AAGGAG                        36

(2) INFORMATION FOR SEQ ID NO: 655:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 655:

AGCUUGCCUG AUGAGGCCGA AAGGCCGAAA AAAGGA                              36

(2) INFORMATION FOR SEQ ID NO: 656:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 656:

GGAACACCUG AUGAGGCCGA AAGGCCGAAA UGGCCA                              36

(2) INFORMATION FOR SEQ ID NO: 657:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 657:

GGUCCGGCUG AUGAGGCCGA AAGGCCGAAA CACAAU                              36

(2) INFORMATION FOR SEQ ID NO: 658:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 658:

GGGUCCGCUG AUGAGGCCGA AAGGCCGAAA ACACAA                              36

(2) INFORMATION FOR SEQ ID NO: 659:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 659:

GCGUAGGCUG AUGAGGCCGA AAGGCCGAAA GGGGUC                              36

(2) INFORMATION FOR SEQ ID NO: 660:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 660:

GUCUGCGCUG AUGAGGCCGA AAGGCCGAAA GGGAGG                              36

-continued (2) INFORMATION FOR SEQ ID NO: 661:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 661:

CGCACAGCUG AUGAGGCCGA AAGGCCGAAA GCCUGC                    36

(2) INFORMATION FOR SEQ ID NO: 662:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 662:

GCAUGGACUG AUGAGGCCGA AAGGCCGAAA CACGCA                    36

(2) INFORMATION FOR SEQ ID NO: 663:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 663:

CUGCAUGCUG AUGAGGCCGA AAGGCCGAAA GACACG                    36

(2) INFORMATION FOR SEQ ID NO: 664:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 664:

CGGUCGGCUG AUGAGGCCGA AAGGCCGAAA GGCCGC                    36

(2) INFORMATION FOR SEQ ID NO: 665:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 665:

CCGGUCGCUG AUGAGGCCGA AAGGCCGAAA AGGCCG                    36

(2) INFORMATION FOR SEQ ID NO: 666:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 666:

GCUCACUCUG AUGAGGCCGA AAGGCCGAAA GCUCCC                    36

(2) INFORMATION FOR SEQ ID NO: 667:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 667:

GUACUGGCUG AUGAGGCCGA AAGGCCGAAA UUCCAU                             36

(2) INFORMATION FOR SEQ ID NO: 668:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 668:

GGUACUGCUG AUGAGGCCGA AAGGCCGAAA AUUCCA                             36

(2) INFORMATION FOR SEQ ID NO: 669:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 669:

UGGCAGGCUG AUGAGGCCGA AAGGCCGAAA CUGGAA                             36

(2) INFORMATION FOR SEQ ID NO: 670:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 670:

UCGUCUGCUG AUGAGGCCGA AAGGCCGAAA UCUGGC                             36

(2) INFORMATION FOR SEQ ID NO: 671:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 671:

CGGUGACCUG AUGAGGCCGA AAGGCCGAAA UCGUCU                             36

(2) INFORMATION FOR SEQ ID NO: 672:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 672:

AUCCGGUCUG AUGAGGCCGA AAGGCCGAAA CGAUCG                             36

(2) INFORMATION FOR SEQ ID NO: 673:

(i) SEQUENCE CHARACTERISTICS:
           (A) LENGTH: 36 base pairs
           (B) TYPE: nucleic acid
           (C) STRANDEDNESS: single
           (D) TOPOLOGY: linear (xi) SEQUENCE DESCRIPTION: SEQ ID NO: 673:

UCUCCUCCUG AUGAGGCCGA AAGGCCGAAA UCCGGU                         36

(2) INFORMATION FOR SEQ ID NO: 674:

(i) SEQUENCE CHARACTERISTICS:
           (A) LENGTH: 36 base pairs
           (B) TYPE: nucleic acid
           (C) STRANDEDNESS: single
           (D) TOPOLOGY: linear (xi) SEQUENCE DESCRIPTION: SEQ ID NO: 674:

GUCCUUUCUG AUGAGGCCGA AAGGCCGAAA CGUUUC                         36

(2) INFORMATION FOR SEQ ID NO: 675:

(i) SEQUENCE CHARACTERISTICS:
           (A) LENGTH: 36 base pairs
           (B) TYPE: nucleic acid
           (C) STRANDEDNESS: single
           (D) TOPOLOGY: linear (xi) SEQUENCE DESCRIPTION: SEQ ID NO: 675:

GGUCUCACUG AUGAGGCCGA AAGGCCGAAA UGUCCU                         36

(2) INFORMATION FOR SEQ ID NO: 676:

(i) SEQUENCE CHARACTERISTICS:
           (A) LENGTH: 36 base pairs
           (B) TYPE: nucleic acid
           (C) STRANDEDNESS: single
           (D) TOPOLOGY: linear (xi) SEQUENCE DESCRIPTION: SEQ ID NO: 676:

GCUCUUGCUG AUGAGGCCGA AAGGCCGAAA GGUCUC                         36

(2) INFORMATION FOR SEQ ID NO: 677:

(i) SEQUENCE CHARACTERISTICS:
           (A) LENGTH: 36 base pairs
           (B) TYPE: nucleic acid
           (C) STRANDEDNESS: single
           (D) TOPOLOGY: linear (xi) SEQUENCE DESCRIPTION: SEQ ID NO: 677:

UGCUCUUCUG AUGAGGCCGA AAGGCCGAAA AGGUCU                         36

(2) INFORMATION FOR SEQ ID NO: 678:

(i) SEQUENCE CHARACTERISTICS:
           (A) LENGTH: 36 base pairs
           (B) TYPE: nucleic acid
           (C) STRANDEDNESS: single
           (D) TOPOLOGY: linear (xi) SEQUENCE DESCRIPTION: SEQ ID NO: 678:

UCUUCAUCUG AUGAGGCCGA AAGGCCGAAA UGCUCU                         36

(2) INFORMATION FOR SEQ ID NO: 679:

(i) SEQUENCE CHARACTERISTICS:

(A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 679:

CUGAAAGCUG AUGAGGCCGA AAGGCCGAAA CUCUUC                                      36

(2) INFORMATION FOR SEQ ID NO: 680:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 680:

CCGCUGACUG AUGAGGCCGA AAGGCCGAAA GGACUC                                      36

(2) INFORMATION FOR SEQ ID NO: 681:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 681:

UCCGCUGCUG AUGAGGCCGA AAGGCCGAAA AGGACU                                      36

(2) INFORMATION FOR SEQ ID NO: 682:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 682:

GUCCGCUCUG AUGAGGCCGA AAGGCCGAAA AAGGAC                                      36

(2) INFORMATION FOR SEQ ID NO: 683:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 683:

CGAGGUGCUG AUGAGGCCGA AAGGCCGAAA GGCCGG                                      36

(2) INFORMATION FOR SEQ ID NO: 684:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 684:

AUGCGUCCUG AUGAGGCCGA AAGGCCGAAA GGUGGA                                      36

(2) INFORMATION FOR SEQ ID NO: 685:

(i) SEQUENCE CHARACTERISTICS:
        (A) LENGTH: 36 base pairs

```
        (B) TYPE: nucleic acid
        (C) STRANDEDNESS: single
        (D) TOPOLOGY: linear (xi) SEQUENCE DESCRIPTION: SEQ ID NO: 685:

GCACAGCCUG AUGAGGCCGA AAGGCCGAAA UGCGUC                          36

(2) INFORMATION FOR SEQ ID NO: 686:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 686:

CUGCGGGCUG AUGAGGCCGA AAGGCCGAAA GGCACA                          36

(2) INFORMATION FOR SEQ ID NO: 687:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 687:

GCUGCGGCUG AUGAGGCCGA AAGGCCGAAA AGGCAC                          36

(2) INFORMATION FOR SEQ ID NO: 688:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 688:

AGAAGCUCUG AUGAGGCCGA AAGGCCGAAA GCUGCG                          36

(2) INFORMATION FOR SEQ ID NO: 689:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 689:

GGGACAGCUG AUGAGGCCGA AAGGCCGAAA GCUGAG                          36

(2) INFORMATION FOR SEQ ID NO: 690:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 690:

GGGGACACUG AUGAGGCCGA AAGGCCGAAA AGCUGA                          36

(2) INFORMATION FOR SEQ ID NO: 691:

(i) SEQUENCE CHARACTERISTICS:
        (A) LENGTH: 36 base pairs
        (B) TYPE: nucleic acid
```

(C) STRANDEDNESS: single
        (D) TOPOLOGY: linear (xi) SEQUENCE DESCRIPTION: SEQ ID NO: 691:

GCUUGGGCUG AUGAGGCCGA AAGGCCGAAA CAGAAG					36

(2) INFORMATION FOR SEQ ID NO: 692:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 692:

AAAGGGACUG AUGAGGCCGA AAGGCCGAAA GGGCUG					36

(2) INFORMATION FOR SEQ ID NO: 693:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 693:

GUAAAGGCUG AUGAGGCCGA AAGGCCGAAA UAGGGC					36

(2) INFORMATION FOR SEQ ID NO: 694:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 694:

UGACGUACUG AUGAGGCCGA AAGGCCGAAA GGGAUA					36

(2) INFORMATION FOR SEQ ID NO: 695:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 695:

AUGACGUCUG AUGAGGCCGA AAGGCCGAAA AGGGAU					36

(2) INFORMATION FOR SEQ ID NO: 696:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 696:

GAUGACGCUG AUGAGGCCGA AAGGCCGAAA AAGGGA					36

(2) INFORMATION FOR SEQ ID NO: 697:

(i) SEQUENCE CHARACTERISTICS:
        (A) LENGTH: 36 base pairs
        (B) TYPE: nucleic acid
        (C) STRANDEDNESS: single (D) TOPOLOGY: linear (xi) SEQUENCE DESCRIPTION: SEQ ID NO: 697:

CAGGGAUCUG AUGAGGCCGA AAGGCCGAAA CGUAAA                                36

(2) INFORMATION FOR SEQ ID NO: 698:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (xi) SEQUENCE DESCRIPTION: SEQ ID NO: 698:

GCUCAGGCUG AUGAGGCCGA AAGGCCGAAA UGACGU                                36

(2) INFORMATION FOR SEQ ID NO: 699:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (xi) SEQUENCE DESCRIPTION: SEQ ID NO: 699:

CAUAGUUCUG AUGAGGCCGA AAGGCCGAAA UGGUGC                                36

(2) INFORMATION FOR SEQ ID NO: 700:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (xi) SEQUENCE DESCRIPTION: SEQ ID NO: 700:

CUCAUCACUG AUGAGGCCGA AAGGCCGAAA GUUGAU                                36

(2) INFORMATION FOR SEQ ID NO: 701:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (xi) SEQUENCE DESCRIPTION: SEQ ID NO: 701:

GGUGGGACUG AUGAGGCCGA AAGGCCGAAA CUCAUC                                36

(2) INFORMATION FOR SEQ ID NO: 702:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (xi) SEQUENCE DESCRIPTION: SEQ ID NO: 702:

UGGUGGGCUG AUGAGGCCGA AAGGCCGAAA ACUCAU                                36

(2) INFORMATION FOR SEQ ID NO: 703:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (xi) SEQUENCE DESCRIPTION: SEQ ID NO: 703:

AUGGUGGCUG AUGAGGCCGA AAGGCCGAAA AACUCA                          36

(2) INFORMATION FOR SEQ ID NO: 704:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 704:

AGAAGGACUG AUGAGGCCGA AAGGCCGAAA CACCAU                          36

(2) INFORMATION FOR SEQ ID NO: 705:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 705:

CAGAAGGCUG AUGAGGCCGA AAGGCCGAAA ACACCA                          36

(2) INFORMATION FOR SEQ ID NO: 706:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 706:

CCAGAAGCUG AUGAGGCCGA AAGGCCGAAA AACACC                          36

(2) INFORMATION FOR SEQ ID NO: 707:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 707:

UGCCCAGCUG AUGAGGCCGA AAGGCCGAAA GGAAAC                          36

(2) INFORMATION FOR SEQ ID NO: 708:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 708:

CUGCCCACUG AUGAGGCCGA AAGGCCGAAA AGGAAA                          36

(2) INFORMATION FOR SEQ ID NO: 709:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 709:

CCUGGCUCUG AUGAGGCCGA AAGGCCGAAA UCUGCC         36

(2) INFORMATION FOR SEQ ID NO: 710:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 710:

CAAGGCCCUG AUGAGGCCGA AAGGCCGAAA GGCCUG         36

(2) INFORMATION FOR SEQ ID NO: 711:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 711:

CGGGGCCCUG AUGAGGCCGA AAGGCCGAAA GGCCGA         36

(2) INFORMATION FOR SEQ ID NO: 712:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 712:

ACUUGGGCUG AUGAGGCCGA AAGGCCGAAA GGGGCC         36

(2) INFORMATION FOR SEQ ID NO: 713:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 713:

GGGGCAGCUG AUGAGGCCGA AAGGCCGAAA CUUGGG         36

(2) INFORMATION FOR SEQ ID NO: 714:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 714:

GGGGCUGCUG AUGAGGCCGA AAGGCCGAAA GCCUGG         36

(2) INFORMATION FOR SEQ ID NO: 715:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 715:

```
AUGGCUGCUG AUGAGGCCGA AAGGCCGAAA GCAGGG                    36
```

(2) INFORMATION FOR SEQ ID NO: 716:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 716:

```
GAGCUGACUG AUGAGGCCGA AAGGCCGAAA CCAUGG                    36
```

(2) INFORMATION FOR SEQ ID NO: 717:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 717:

```
CAGAGCUCUG AUGAGGCCGA AAGGCCGAAA UACCAU                    36
```

(2) INFORMATION FOR SEQ ID NO: 718:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 718:

```
UGGGCCACUG AUGAGGCCGA AAGGCCGAAA GCUGAU                    36
```

(2) INFORMATION FOR SEQ ID NO: 719:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 719:

```
GGACUGGCUG AUGAGGCCGA AAGGCCGAAA CAGGGG                    36
```

(2) INFORMATION FOR SEQ ID NO: 720:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 720:

```
GGGCUAGCUG AUGAGGCCGA AAGGCCGAAA CUGGGA                    36
```

(2) INFORMATION FOR SEQ ID NO: 721:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 721:

```
CUGGGGCCUG AUGAGGCCGA AAGGCCGAAA GGACUG                                      36
```

(2) INFORMATION FOR SEQ ID NO: 722:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 722:

```
GCCUGAGCUG AUGAGGCCGA AAGGCCGAAA GGGCCU                                      36
```

(2) INFORMATION FOR SEQ ID NO: 723:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 723:

```
ACAGCCUCUG AUGAGGCCGA AAGGCCGAAA GGAGGG                                      36
```

(2) INFORMATION FOR SEQ ID NO: 724:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 724:

```
GGCCUCUCUG AUGAGGCCGA AAGGCCGAAA CAGCGU                                      36
```

(2) INFORMATION FOR SEQ ID NO: 725:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 725:

```
AUCAUCACUG AUGAGGCCGA AAGGCCGAAA CUGCAG                                      36
```

(2) INFORMATION FOR SEQ ID NO: 726:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 726:

```
CAUCAUCCUG AUGAGGCCGA AAGGCCGAAA ACUGCA                                      36
```

(2) INFORMATION FOR SEQ ID NO: 727:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 727:

```
GCCAAGCCUG AUGAGGCCGA AAGGCCGAAA GGCCCC                                      36
```

(2) INFORMATION FOR SEQ ID NO: 728:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 728:

UGUUGCCCUG AUGAGGCCGA AAGGCCGAAA GCAAGG      36

(2) INFORMATION FOR SEQ ID NO: 729:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 729:

GUCUGUGCUG AUGAGGCCGA AAGGCCGAAA CACAGC      36

(2) INFORMATION FOR SEQ ID NO: 730:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 730:

GGUCUGUCUG AUGAGGCCGA AAGGCCGAAA ACACAG      36

(2) INFORMATION FOR SEQ ID NO: 731:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 731:

GUCGACGCUG AUGAGGCCGA AAGGCCGAAA UGCCAG      36

(2) INFORMATION FOR SEQ ID NO: 732:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 732:

AGUUGUCCUG AUGAGGCCGA AAGGCCGAAA CGGAUG      36

(2) INFORMATION FOR SEQ ID NO: 733:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 733:

AAACUCGCUG AUGAGGCCGA AAGGCCGAAA GUUGUC      36

(2) INFORMATION FOR SEQ ID NO: 734:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 734:

CUGCUGACUG AUGAGGCCGA AAGGCCGAAA CUCGGA                    36

(2) INFORMATION FOR SEQ ID NO: 735:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 735:

GCUGCUGCUG AUGAGGCCGA AAGGCCGAAA ACUCGG                    36

(2) INFORMATION FOR SEQ ID NO: 736:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 736:

AGCUGCUCUG AUGAGGCCGA AAGGCCGAAA AACUCG                    36

(2) INFORMATION FOR SEQ ID NO: 737:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 737:

CCACAGGCUG AUGAGGCCGA AAGGCCGAAA UGCCCU                    36

(2) INFORMATION FOR SEQ ID NO: 738:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 738:

CUCAGGGCUG AUGAGGCCGA AAGGCCGAAA CUCCAU                    36

(2) INFORMATION FOR SEQ ID NO: 739:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 739:

CGAGUUACUG AUGAGGCCGA AAGGCCGAAA GCCUCA                    36

(2) INFORMATION FOR SEQ ID NO: 740:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 740:

GGCGAGUCUG AUGAGGCCGA AAGGCCGAAA UAGCCU                    36

(2) INFORMATION FOR SEQ ID NO: 741:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 741:

ACUAGGCCUG AUGAGGCCGA AAGGCCGAAA GUUAUA                    36

(2) INFORMATION FOR SEQ ID NO: 742:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 742:

CUGUCACCUG AUGAGGCCGA AAGGCCGAAA GGCGAG                    36

(2) INFORMATION FOR SEQ ID NO: 743:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 743:

GGAGCAGCUG AUGAGGCCGA AAGGCCGAAA GCUGGG                    36

(2) INFORMATION FOR SEQ ID NO: 744:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 744:

CCCAGUGCUG AUGAGGCCGA AAGGCCGAAA GCAGGA                    36

(2) INFORMATION FOR SEQ ID NO: 745:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 745:

CAUUGGGCUG AUGAGGCCGA AAGGCCGAAA GCCCCG                    36

(2) INFORMATION FOR SEQ ID NO: 746:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO: 746:

CUGAAAGCUG AUGAGGCCGA AAGGCCGAAA GGCCAU                        36

(2) INFORMATION FOR SEQ ID NO: 747:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 747:

CUCCUGACUG AUGAGGCCGA AAGGCCGAAA GGAGGC                        36

(2) INFORMATION FOR SEQ ID NO: 748:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 748:

UCUCCUGCUG AUGAGGCCGA AAGGCCGAAA AGGAGG                        36

(2) INFORMATION FOR SEQ ID NO: 749:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 749:

AUCUCCUCUG AUGAGGCCGA AAGGCCGAAA AAGGAG                        36

(2) INFORMATION FOR SEQ ID NO: 750:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 750:

GGAGGAGCUG AUGAGGCCGA AAGGCCGAAA GUCUUC                        36

(2) INFORMATION FOR SEQ ID NO: 751:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 751:

UGGAGGACUG AUGAGGCCGA AAGGCCGAAA AGUCUU                        36

(2) INFORMATION FOR SEQ ID NO: 752:

```
    (i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 752:

AAUGGAGCUG AUGAGGCCGA AAGGCCGAAA GAAGUC                             36

(2) INFORMATION FOR SEQ ID NO: 753:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 753:

CGCAAUGCUG AUGAGGCCGA AAGGCCGAAA GGAGAA                             36

(2) INFORMATION FOR SEQ ID NO: 754:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 754:

UGUCCGCCUG AUGAGGCCGA AAGGCCGAAA UGGAGG                             36

(2) INFORMATION FOR SEQ ID NO: 755:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 755:

GGCUGAGCUG AUGAGGCCGA AAGGCCGAAA GUCCAU                             36

(2) INFORMATION FOR SEQ ID NO: 756:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 756:

GGGCUGACUG AUGAGGCCGA AAGGCCGAAA AGUCCA                             36

(2) INFORMATION FOR SEQ ID NO: 757:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 757:

CAGGGCUCUG AUGAGGCCGA AAGGCCGAAA GAAGUC                             36

(2) INFORMATION FOR SEQ ID NO: 758:

(i) SEQUENCE CHARACTERISTICS:
```

(A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 758:

CUGAUCUCUG AUGAGGCCGA AAGGCCGAAA CUCAGC        36

(2) INFORMATION FOR SEQ ID NO: 759:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 759:

AGGAGCUCUG AUGAGGCCGA AAGGCCGAAA UCUGAC        36

(2) INFORMATION FOR SEQ ID NO: 760:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 760:

CCCUUAGCUG AUGAGGCCGA AAGGCCGAAA GCUGAU        36

(2) INFORMATION FOR SEQ ID NO: 761:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 761:

ACCCCCUCUG AUGAGGCCGA AAGGCCGAAA GGAGCU        36

(2) INFORMATION FOR SEQ ID NO: 762:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 762:

CUCUGGGCUG AUGAGGCCGA AAGGCCGAAA GGGCAG        36

(2) INFORMATION FOR SEQ ID NO: 763:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 763:

UGAGGGGAG AAGUUCACCA GAGAAACACA CGUUGUGGUA CAUUACCUGG UA        52

(2) INFORMATION FOR SEQ ID NO: 764:

(i) SEQUENCE CHARACTERISTICS:
        (A) LENGTH: 52 base pairs (B) TYPE: nucleic acid
        (C) STRANDEDNESS: single
        (D) TOPOLOGY: linear (xi) SEQUENCE DESCRIPTION: SEQ ID NO: 764:

GCUGCUUGAG AAGCUCACCA GAGAAACACA CGUUGUGGUA CAUUACCUGG UA          52

(2) INFORMATION FOR SEQ ID NO: 765:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 765:

GCCAUCCCAG AAGUCCACCA GAGAAACACA CGUUGUGGUA CAUUACCUGG UA          52

(2) INFORMATION FOR SEQ ID NO: 766:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 766:

GUUCUGGAAG AAGUGGACCA GAGAAACACA CGUUGUGGUA CAUUACCUGG UA          52

(2) INFORMATION FOR SEQ ID NO: 767:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 767:

GAAGGACAAG AAGCAGACCA GAGAAACACA CGUUGUGGUA CAUUACCUGG UA          52

(2) INFORMATION FOR SEQ ID NO: 768:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 768:

UUGAGCUCAG AAGUGUACCA GAGAAACACA CGUUGUGGUA CAUUACCUGG UA          52

(2) INFORMATION FOR SEQ ID NO: 769:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 769:

CCCACCGAAG AAGCUGACCA GAGAAACACA CGUUGUGGUA CAUUACCUGG UA          52

(2) INFORMATION FOR SEQ ID NO: 770:

(i) SEQUENCE CHARACTERISTICS:
        (A) LENGTH: 52 base pairs
        (B) TYPE: nucleic acid (C) STRANDEDNESS: single
            (D) TOPOLOGY: linear (xi) SEQUENCE DESCRIPTION: SEQ ID NO: 770:

AGGCUGGGAG AAGCGUACCA GAGAAACACA CGUUGUGGUA CAUUACCUGG UA            52

(2) INFORMATION FOR SEQ ID NO: 771:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (xi) SEQUENCE DESCRIPTION: SEQ ID NO: 771:

GGUCGGAAAG AAGCCGACCA GAGAAACACA CGUUGUGGUA CAUUACCUGG UA            52

(2) INFORMATION FOR SEQ ID NO: 772:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (xi) SEQUENCE DESCRIPTION: SEQ ID NO: 772:

UGACGAUCAG AAGUAUACCA GAGAAACACA CGUUGUGGUA CAUUACCUGG UA            52

(2) INFORMATION FOR SEQ ID NO: 773:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (xi) SEQUENCE DESCRIPTION: SEQ ID NO: 773:

GUCGGUGGAG AAGCUGACCA GAGAAACACA CGUUGUGGUA CAUUACCUGG UA            52

(2) INFORMATION FOR SEQ ID NO: 774:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (xi) SEQUENCE DESCRIPTION: SEQ ID NO: 774:

GGCCGGGGAG AAGUGGACCA GAGAAACACA CGUUGUGGUA CAUUACCUGG UA            52

(2) INFORMATION FOR SEQ ID NO: 775:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (xi) SEQUENCE DESCRIPTION: SEQ ID NO: 775:

CAUCAUCAAG AAGCAGACCA GAGAAACACA CGUUGUGGUA CAUUACCUGG UA            52

(2) INFORMATION FOR SEQ ID NO: 776:

(i) SEQUENCE CHARACTERISTICS:
            (A) LENGTH: 52 base pairs
            (B) TYPE: nucleic acid
            (C) STRANDEDNESS: single (D) TOPOLOGY: linear (xi) SEQUENCE DESCRIPTION: SEQ ID NO: 776:

ACAGCUGGAG AAGUGCACCA GAGAAACACA CGUUGUGGUA CAUUACCUGG UA            52

(2) INFORMATION FOR SEQ ID NO: 777:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 777:

GAUGCCAGAG AAGUGAACCA GAGAAACACA CGUUGUGGUA CAUUACCUGG UA            52

(2) INFORMATION FOR SEQ ID NO: 778:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 778:

GAACUGUUCC CCCUCA                                                    16

(2) INFORMATION FOR SEQ ID NO: 779:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 779:

GAGCAGCCCA AGCAGC                                                    16

(2) INFORMATION FOR SEQ ID NO: 780:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 780:

GGACUGCCGG GAUGGC                                                    16

(2) INFORMATION FOR SEQ ID NO: 781:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 781:

CCACAGUUUC CAGAAC                                                    16

(2) INFORMATION FOR SEQ ID NO: 782:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 782:

CUGCCGCCUG UCCUUC                                                        16

(2) INFORMATION FOR SEQ ID NO: 783:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 783:

ACACUGCCGA GCUCAA                                                        16

(2) INFORMATION FOR SEQ ID NO: 784:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 784:

CAGCUGCCUC GGUGGG                                                        16

(2) INFORMATION FOR SEQ ID NO: 785:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 785:

ACGCAGACCC CAGCCU                                                        16

(2) INFORMATION FOR SEQ ID NO: 786:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 786:

CGGCGGCCUU CCGACC                                                        16

(2) INFORMATION FOR SEQ ID NO: 787:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 787:

AUACAGACGA UCGUCA                                                        16

(2) INFORMATION FOR SEQ ID NO: 788:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 788:

CAGCGGACCC ACCGAC                                                    16

(2) INFORMATION FOR SEQ ID NO: 789:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 789:

CCACCGACCC CCGGCC                                                    16

(2) INFORMATION FOR SEQ ID NO: 790:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 790:

CUGCAGUUUG AUGAUG                                                    16

(2) INFORMATION FOR SEQ ID NO: 791:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 791:

GCACAGACCC AGCUGU                                                    16

(2) INFORMATION FOR SEQ ID NO: 792:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 792:

UCACAGACCU GGCAUC                                                    16

(2) INFORMATION FOR SEQ ID NO: 793:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 793:

GUUGCUUCAG AAGUUCACCA GAGAAACACA CGUUGUGGUA CAUUACCUGG UA            52

(2) INFORMATION FOR SEQ ID NO: 794:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 794:

GAGAUUCGAG AAGUUCACCA GAGAAACACA CGUUGUGGUA CAUUACCUGG UA        52

(2) INFORMATION FOR SEQ ID NO: 795:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 795:

GCCAUCCCAG AAGUCCACCA GAGAAACACA CGUUGUGGUA CAUUACCUGG UA        52

(2) INFORMATION FOR SEQ ID NO: 796:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 796:

GGGCAGAGAG AAGCCUACCA GAGAAACACA CGUUGUGGUA CAUUACCUGG UA        52

(2) INFORMATION FOR SEQ ID NO: 797:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 797:

UUGAGCUCAG AAGUGUACCA GAGAAACACA CGUUGUGGUA CAUUACCUGG UA        52

(2) INFORMATION FOR SEQ ID NO: 798:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 798:

CCCACCGAAG AAGCUCACCA GAGAAACACA CGUUGUGGUA CAUUACCUGG UA        52

(2) INFORMATION FOR SEQ ID NO: 799:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 799:

AGGCUGGGAG AAGCGUACCA GAGAAACACA CGUUGUGGUA CAUUACCUGG UA        52

(2) INFORMATION FOR SEQ ID NO: 800:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 800:

-continued

GAUCAGAAAG AAGCCGACCA GAGAAACACA CGUUGUGGUA CAUUACCUGG UA    52

(2) INFORMATION FOR SEQ ID NO: 801:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 801:

AGGUGUAGAG AAGCGGACCA GAGAAACACA CGUUGUGGUA CAUUACCUGG UA    52

(2) INFORMATION FOR SEQ ID NO: 802:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 802:

GGGCAGAGAG AAGUGCACCA GAGAAACACA CGUUGUGGUA CAUUACCUGG UA    52

(2) INFORMATION FOR SEQ ID NO: 803:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 803:

GGGCUUCCAG AAGCGUACCA GAGAAACACA CGUUGUGGUA CAUUACCUGG UA    52

(2) INFORMATION FOR SEQ ID NO: 804:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 804:

CAGCAUCAAG AAGCAGACCA GAGAAACACA CGUUGUGGUA CAUUACCUGG UA    52

(2) INFORMATION FOR SEQ ID NO: 805:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 805:

ACUCCUGGAG AAGUGCACCA GAGAAACACA CGUUGUGGUA CAUUACCUGG UA    52

(2) INFORMATION FOR SEQ ID NO: 806:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 806:

GAUGCCAGAG AAGUGAACCA GAGAAACACA CGUUGUGGUA CAUUACCUGG UA    52

(2) INFORMATION FOR SEQ ID NO: 807:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 807:

AAGUCGGGAG AAGCUGACCA GAGAAACACA CGUUGUGGUA CAUUACCUGG UA            52

(2) INFORMATION FOR SEQ ID NO: 808:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 808:

UGGCUCCAAG AAGUCCACCA GAGAAACACA CGUUGUGGUA CAUUACCUGG UA            52

(2) INFORMATION FOR SEQ ID NO: 809:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 809:

UGGUGUCGAG AAGCACACCA GAGAAACACA CGUUGUGGUA CAUUACCUGG UA            52

(2) INFORMATION FOR SEQ ID NO: 810:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 810:

AUUCUGAAAG AAGCCAACCA GAGAAACACA CGUUGUGGUA CAUUACCUGG UA            52

(2) INFORMATION FOR SEQ ID NO: 811:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 811:

UCAGUAAAAG AAGUCUACCA GAGAAACACA CGUUGUGGUA CAUUACCUGG UA            52

(2) INFORMATION FOR SEQ ID NO: 812:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 812:

GAACAGCCGA AGCAAC                                                    16

(2) INFORMATION FOR SEQ ID NO: 813:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 813:

GAACAGUUCG AAUCUC                                              16

(2) INFORMATION FOR SEQ ID NO: 814:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 814:

GGACUGCCGG GAUGGC                                              16

(2) INFORMATION FOR SEQ ID NO: 815:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 815:

AGGCUGACCU CUGCCC                                              16

(2) INFORMATION FOR SEQ ID NO: 816:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 816:

ACACUGCCGA GCUCAA                                              16

(2) INFORMATION FOR SEQ ID NO: 817:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 817:

GAGCUGCCUC GGUGGG                                              16

(2) INFORMATION FOR SEQ ID NO: 818:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 818:

ACGCCGACCC CAGCCU                                              16

(2) INFORMATION FOR SEQ ID NO: 819:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 819:

CGGCGGCCUU CUGAUC                                                              16

(2) INFORMATION FOR SEQ ID NO: 820:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 820:

CCGCAGCCCU ACACCU                                                              16

(2) INFORMATION FOR SEQ ID NO: 821:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 821:

GCACCGUCCU CUGCCC                                                              16

(2) INFORMATION FOR SEQ ID NO: 822:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 822:

ACGCUGUCGG AAGCCC                                                              16

(2) INFORMATION FOR SEQ ID NO: 823:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 823:

CUGCAGUUUG AUGCUG                                                              16

(2) INFORMATION FOR SEQ ID NO: 824:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 824:

GCACAGACCC AGGAGU                                                              16

(2) INFORMATION FOR SEQ ID NO: 825:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 825:

UCACAGACCU GGCAUC                                          16

(2) INFORMATION FOR SEQ ID NO: 826:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 826:

CAGCUGCCCC CGACUU                                          16

(2) INFORMATION FOR SEQ ID NO: 827:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 827:

GGACAGACUG GAGCCA                                          16

(2) INFORMATION FOR SEQ ID NO: 828:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 828:

GUGCUGCCCG ACACCA                                          16

(2) INFORMATION FOR SEQ ID NO: 829:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 829:

UGGCCGCCUU CAGAAU                                          16

(2) INFORMATION FOR SEQ ID NO: 830:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 830:

AGACAGCCUU UACUGA                                          16